United States Patent
Miesenböck et al.

(12) 
(10) Patent No.: US 6,670,449 B1
(45) Date of Patent: Dec. 30, 2003

(54) HYBRID MOLECULES AND THEIR USE FOR OPTICALLY DETECTING CHANGES IN CELLULAR MICROENVIRONMENTS

(75) Inventors: Gero Miesenböck, New York, NY (US); Dino De Angelis, New York, NY (US); James E. Rothman, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 09/023,946

(22) Filed: Feb. 13, 1998

Related U.S. Application Data

(60) Provisional application No. 60/038,179, filed on Feb. 13, 1997, and provisional application No. 60/036,805, filed on Feb. 14, 1997.

(51) Int. Cl.$^7$ .............................................. A61K 38/00
(52) U.S. Cl. ...................................................... 530/350
(58) Field of Search ................................ 530/350, 300; 514/2; 800/2

(56) References Cited

U.S. PATENT DOCUMENTS

| | | | |
|---|---|---|---|
| 4,603,209 A | 7/1986 | Tsien et al. | 548/236 |
| 5,049,673 A | 9/1991 | Tsien et al. | 546/107 |
| 5,134,232 A | 7/1992 | Tsien et al. | 540/467 |
| 5,196,524 A | 3/1993 | Gustafson et al. | 536/23.2 |
| 5,292,658 A | 3/1994 | Cormier et al. | 435/252.33 |
| 5,360,728 A | 11/1994 | Prasher | 435/189 |
| 5,418,155 A | 5/1995 | Cormier et al. | 435/189 |
| 5,422,266 A | 6/1995 | Cormier et al. | 435/252.3 |
| 5,486,455 A | 1/1996 | Stults | 435/6 |
| 5,491,084 A | 2/1996 | Chalfie | 435/189 |
| 5,541,309 A | 7/1996 | Prasher | 536/23.2 |
| 5,583,024 A | 12/1996 | McElroy et al. | 135/189 |
| 5,625,048 A | 4/1997 | Tsien et al. | 536/23.4 |
| 6,124,128 A | 9/2000 | Tsien et al. | 435/252.33 |

FOREIGN PATENT DOCUMENTS

| | | |
|---|---|---|
| WO | WO 96/23810 | 8/1996 |
| WO | WO 96/23898 | 8/1996 |
| WO | WO 97/26333 | 7/1997 |
| WO | WO 97/42320 | 11/1997 |
| WO | WO 98/21355 | 5/1998 |

OTHER PUBLICATIONS

Prasher et al., Gene, vol. 111, pp. 229–233, 1992.*
Yang et al., Gene, vol. 173, pp. 19–23, 1996.*
Lisa A. Elferink, et al., 1989, *The Journal of Biological Chemistry*, 264:11061–11064.
Mark S. Perin, et al., 1990, *Nature*, 345:260–263.
Roger Heim, et al., 1994, *Proc. Natl. Acad. Sci. USA*, 91:12501–12504.
John Marshall, et al., 1995, *Neuron*, 14:211–215.
Tim Stearns, 1995, *Current Biology*, 5:262–264.
Torsten Ehrig, et al., 1995, *FEBS Letters*, 367:163–166.
Christoph Kaether, et al., 1995, *FEBS Letters*, 369:267–271.
Andrew B. Cubitt, et al., 1995, *TIBS* 20:448–455.
Roger Heim, et al., 1996, *Current Biology*, 6:178–182.
Koki Moriyoshi, et al., 1996, *Neuron*, 16:255–260.
Pieter A. Doevendans, et al., 1996, *Biochem. Biophys. Res. Commun.*, 222:352–358.
Frank Hanakam, et al., 1996, *The EMBO Journal*, 15:2935–2943.
Hans–Hermann Gerdes, et al., 1996, *FEBS Letters*, 389:44–47.
Fan Yang, et al., 1996, *Nature Biotechnology*, 14:1246–1251.
Hiroko Yokoe, et al., 1996, *Nature Biology*, 14:1252–1256.
Mats Ormö, et al., 1996, *Science*, 27:1392–1395.
Gero Miesenböck, et al., 1996, *Proc. Natl. Acad. Sci., USA*, 94:3402–3407.
Christoph Kaether, et al., 1997, *European Journal of Cell Biology*, 74:133–142.
Malea Kneen, et al., 1998, *Biophysical Journal*, 74:1591–1599.
Juan Llopis, et al., 1998, *Cell Biology*, 95:6803–6808.
R. Brooks Robey, et al., 1998, *Biochemistry*, 37:9894–9901.
Thomas C. Südhof, et al., 1989, *Neuron*, 2: 1475–1481.
Gottfried. J. Palm, 1997, *Nature Struct. Biol.*, 4:361–365.
William W. Ward, et al., 1982, "Spectral Perturbations Of The Aequorea Green–Fluorescent Protein", *Photochem. Photobiol.*, 35:803–808.
William W. Ward, et al., 1982, "Reversible Denaturation of Aequorea Green–Fluorescent Protein: Physical Separation and Characterization of the Renatured Protein", *Biochemistry*, 21:4535–4540.
William W. Ward, et al., 1980, "Spectrophotometric Identity Of The Energy Transfer Chromophores In Renilla and Aequorea Green–Fluorescent Proteins", *Photochemistry and Photobiology*, 31:611–615.
Stephen H. Bokman and William W. Ward, 1981, "Renaturation Of Aequorea Green–Fluorescent Protein", *Biochemical And Biophysical Research Communications*, 101: 1372–1380.

(List continued on next page.)

*Primary Examiner*—Karen Cochrane Carlson
*Assistant Examiner*—Sheridan Snedden
(74) *Attorney, Agent, or Firm*—Morgan & Finnegan, LLP

(57) ABSTRACT

The invention relates to methods and compositions which utilize the emission of light to monitor changes in microenvironments involving cells. The invention is especially useful for monitoring exocytotic activity such as detecting quantal release of synaptic vesicles. Fusion proteins of Cypridina luciferase and synaptotagmin-I or VAMP/synaptobrevin-2 were targeted to synaptic vesicles and, upon exocytosis, formed light-emitting complexes with luciferin present in the extracellular medium. Photon emissions in the presence of a depolarizing stimulus can be observed with these systems. pH-sensitive mutants of green fluorescent protein are also provided, which are useful for visualizing exocytosis and for imaging and measuring the pH of intracellular compartments.

32 Claims, 55 Drawing Sheets

OTHER PUBLICATIONS

George H. Patterson, et al., 1997, "Use Of The Green Fluorescent Protein And its Mutants In Quantitative Fluorescence Microscopy", *Biophysical Journal*, 73: 2782–2790.

Rebekka M. Wachter, et al., 1997, "Crystal Structure And Photodynamic Behavior Of The Blue Emission Variant Y66H/Y Of Green Fluorescent Protein", *Biochemistry*, 36:9759–9765.

* cited by examiner

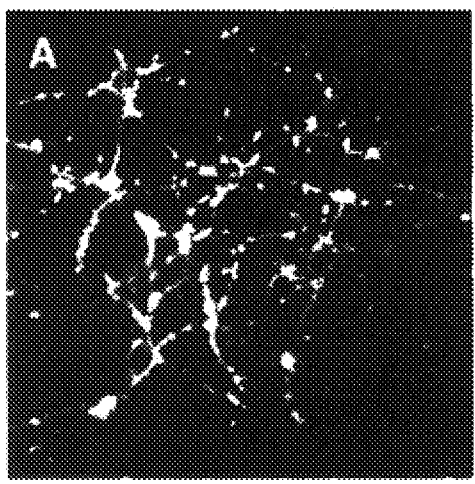
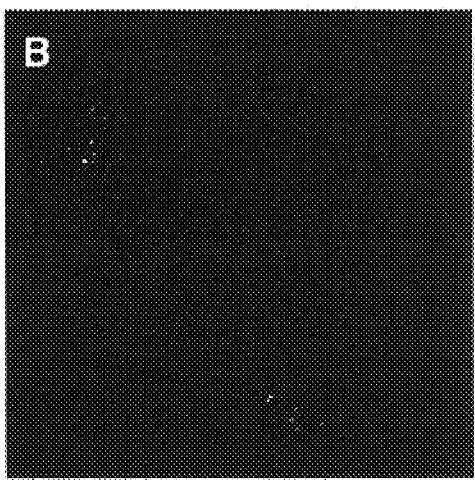
FIG. 2A FIG. 2B
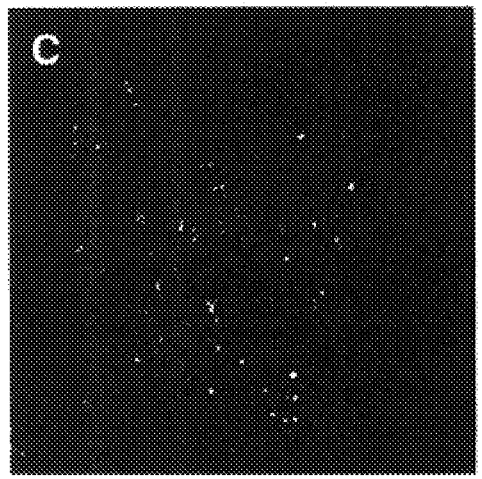
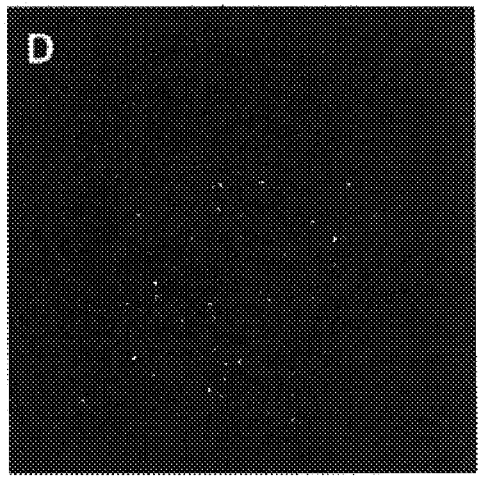
FIG. 2C FIG. 2D
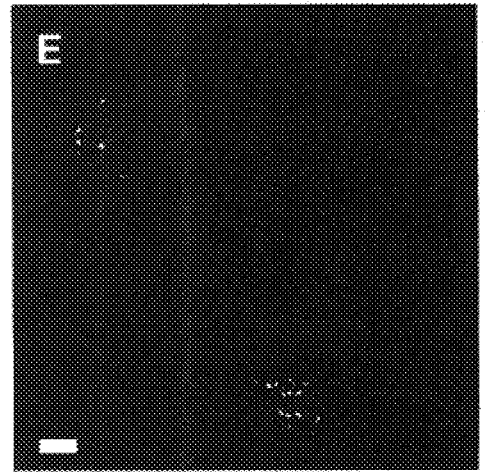
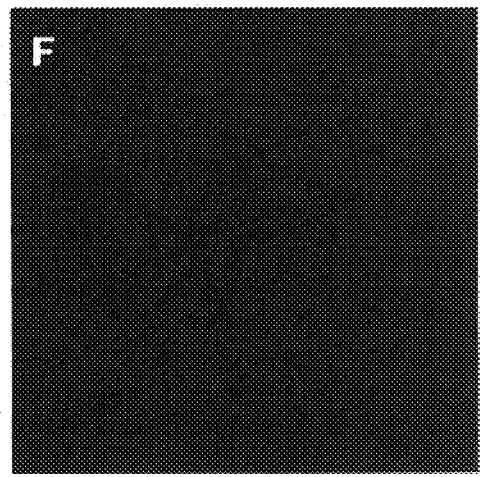
FIG. 2E FIG. 2F GFP protein MGKGEELFTG VVPILVELDG DVNGHKFSVS GEGEGDATYG KLTLKFICTT GKLPVPWPTL VTTFSYGVQC
FSRYPDHMKR HDFFKSAMPE GYVQERTIFF KDDGNYKTRA EVKFEGDTLV NRIELKGIDF KEDGNILGHK
LEYNYNSHNV YIMADKQKNG TKVNFKIRHN IEDGSVQLAD HYQQNTPIGD GPVLLPDNHY LSTQSALSKD
PNEKRDHMVL LEFVTAAGIT HGMDELYKSG SR.

FIGURE 5 wild-type GFP

ATGGGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACTC ACACAATGTA TACATCATGG CAGACAAACA AAAGAATGGA ACCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGTCCACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAGTCCGGA TCTAGATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACGA TCACCAGGTG TACATCATGG CAGACAAACA AAAGAATGGA ATCAAAGCTA
ACTTCAAAAT TAGACACAAC ATTGAAGATG GAGGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATTG AGTTAAAAGG TATTGATTTT AAAGAAGATG GAAACATTCT TGGACACAAA
TTGGAGTACA ACTATAACGA TCACGATGTG TACATCATGG CAGACAAACA AAAGAATGGT ACCAAAGCTA
ACTTTCAAGT TCGCCACAAC ATTGAAGATG GAGGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

FIGURE 7B

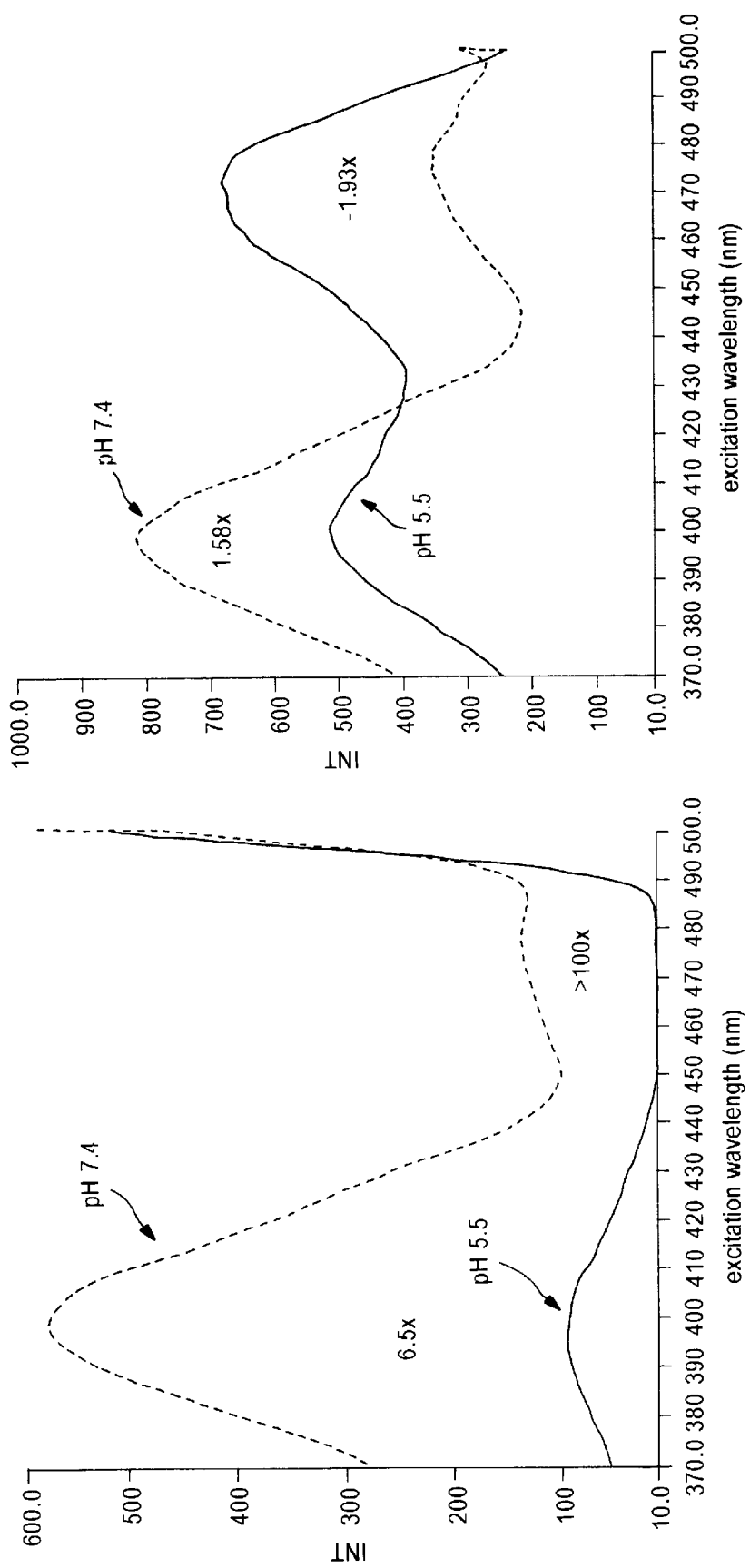

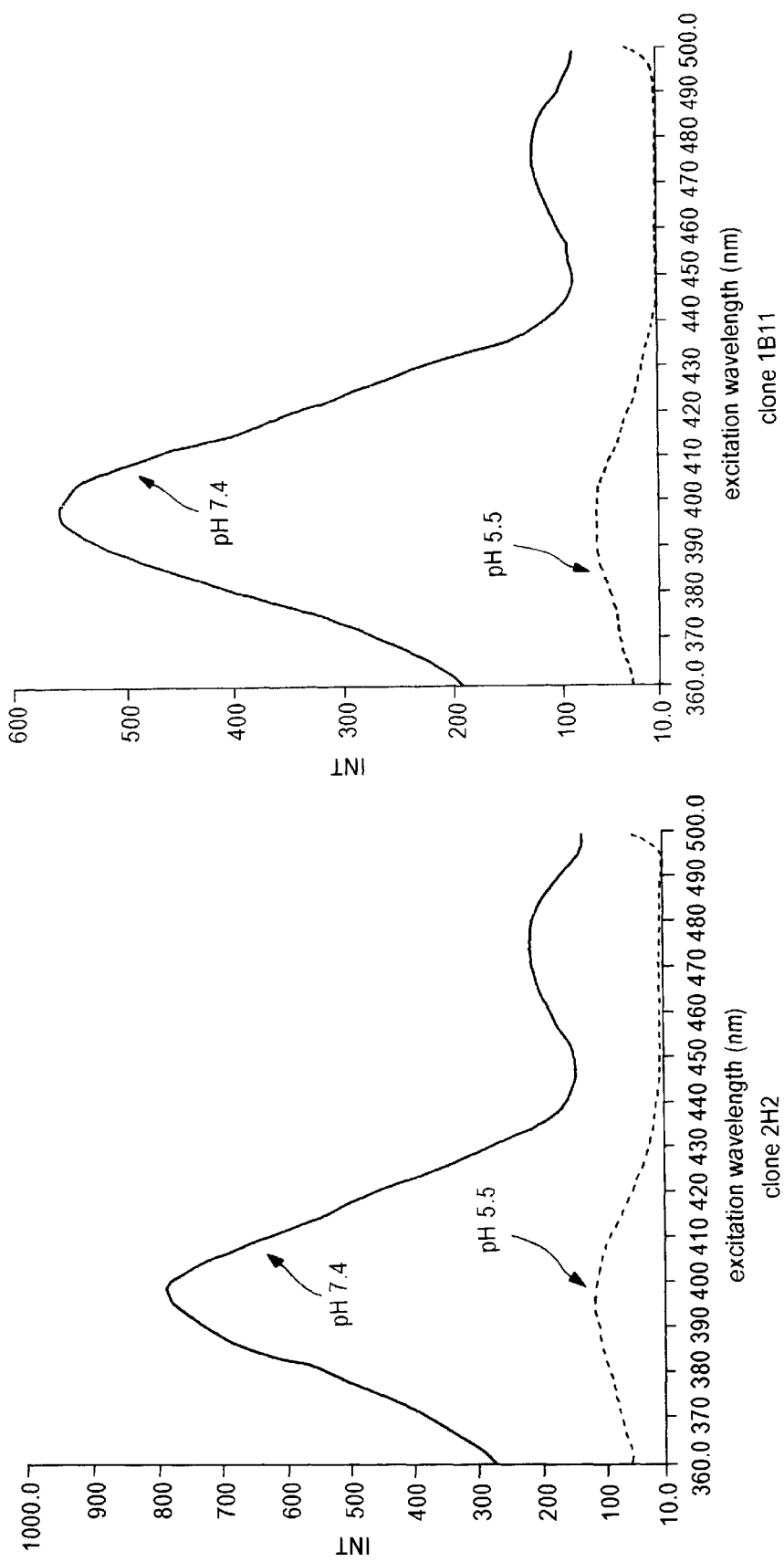

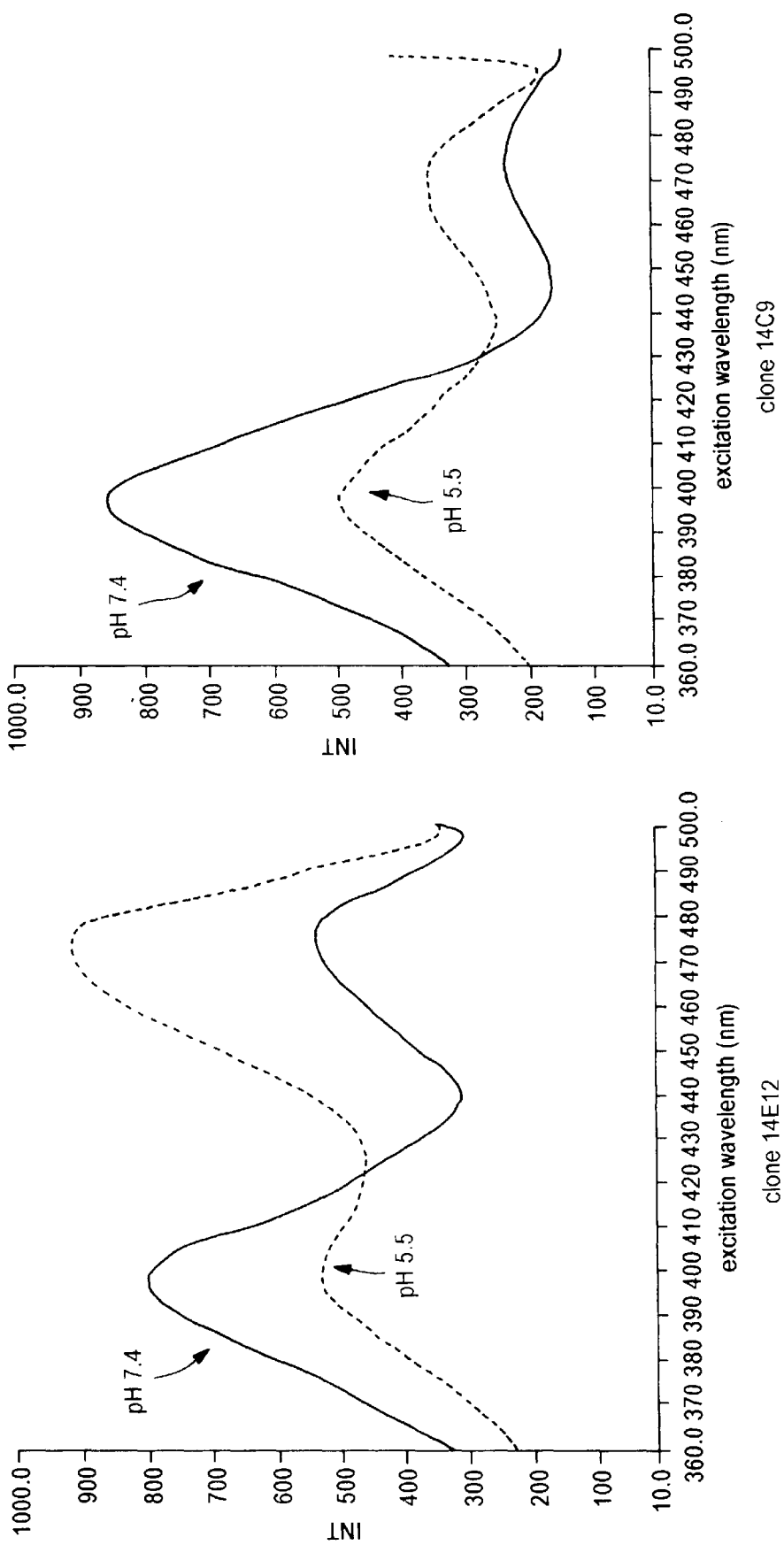

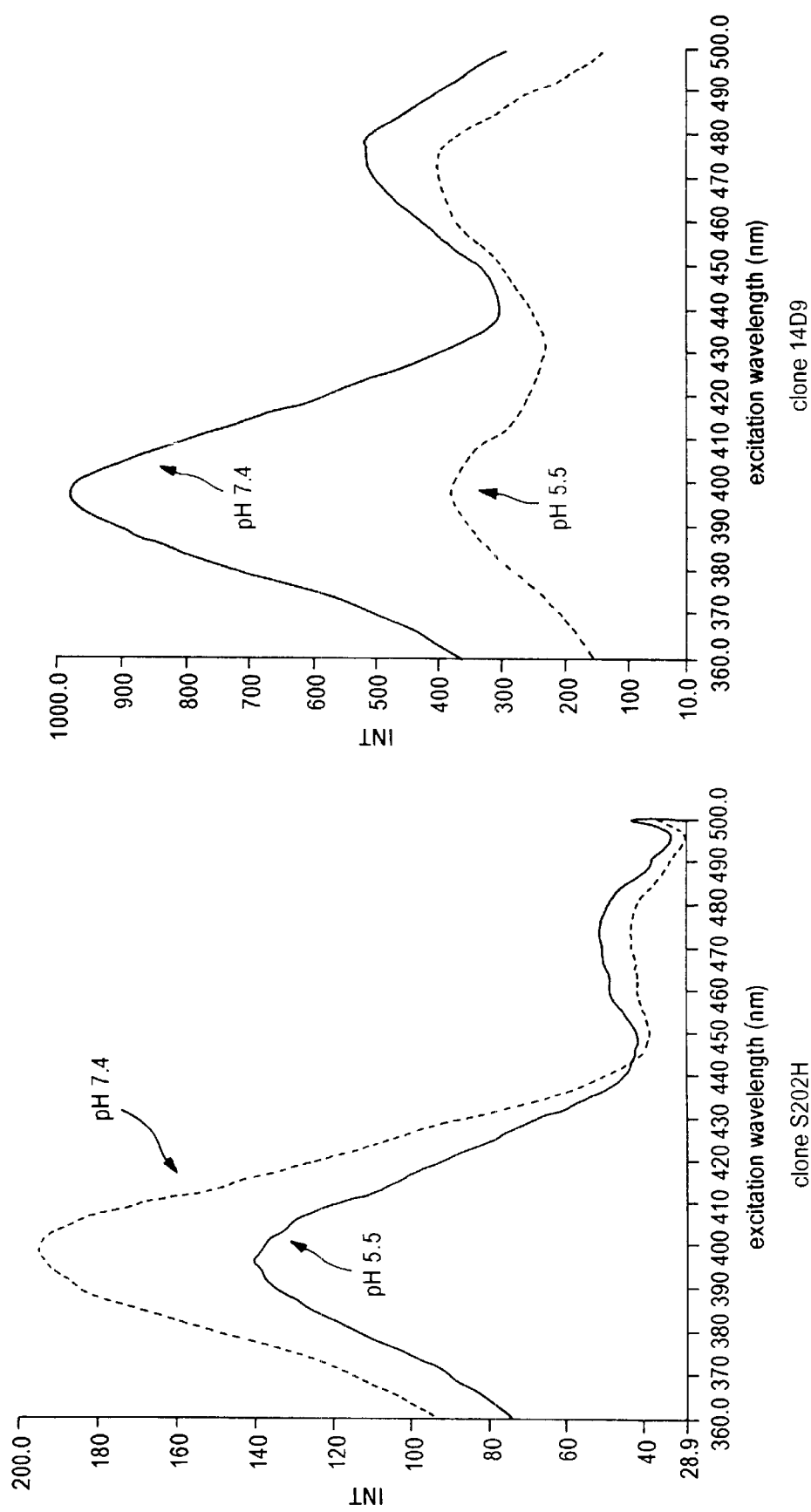
FIG. 10E — clone S202H
FIG. 10F — clone 14D9

1D10

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG CCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACGA TCACAATGTG TACATCATGG CAGACAAACA AAAGAATGGA ATCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG CCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACGA TCACCATGTG TACATCATGG CAGACAAACA AAAGAATGGA ATCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

```
ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT GGACACAAA
TTGGAATACA ACTATAACGA TCACGTGGTG TACATCATGG CAGACAAACA AAAGAATGGA ATCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TCGAAAGAT
CCCAACGAAA AGAGAGACCA CATGGTCCTT CTTGAGTTTG TAACAGCTGC TGGGATTACA CATGGCATGG
ATGAACTATA CAAATAA
```

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG CCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACGA TCACCAGGTG TACATCATGG CAGACAAACA AAAGAATGGA ATCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACGA TCACACTGTG TACATCATGG CAGACAAACA AAAGAATGGA ATCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG CCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATTG AGTTAAAAGG TATTGATTTT AAAGAAGATG GAAACATTCT TGGACACAAA
TTGGAGTACA ACTATAACGA TCACTTGGTG TACATCATGG CAGACAAACA AAAGAATGGT ACCAAAGTTA
ACTTTCAAGT TCACCACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

```
ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATTG AGTTAAAAGG TATTGATTTT AAAGAAGATG GAAACATTCT GGACACAAA
TTGGAGTACA ACTATAACGA TCACGATGTG TACATCATGG CAGACAAACA AAAGAATGGT ACCAAAGTTA
ACTTTCAAGT TCGCCACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA
```

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATTG AGTTAAAAGG TATTGATTTT AAAGAAGATG GAAACATTCT GGACACAAA
TTGGAGTACA ACTATAACGA TCACCTGGTG TACATCATGG CAGACAAACA AAAGAATGGT ACCAAAGTTA
ACTTTCAAGT TCGCCACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATTG AGTTAAAAGG TATTGATTTT AAAGAAGATG GAAACATTCT TGGACACAAA
TTGGAGTACA ACTATAACCC TCACTATGTG TACATCATGG CAGACAAACA AAAGAATGGT ACCAAAGTTA
ACTTTCAAGT TCACCACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACGA GCACTTGGTG TACATCATGG CAGACAAACA AAAGAATGGT ACCAAAGCTA
ACTTTAAAAT TCACCACAAC ATTGAAGATG GAGGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACTC ACACAATGTA TACATCATGG CAGACAAACA AAAGAATGGA ATCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

```
ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG CCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATTG AGTTAAAAGG TATTGATTTT AAAGAAGATG GAAACATTCT TGGACACAAA
TTGGAGTACA ACTATAACCC TCACTGGGTG TACATCATGG CAGACAAACA AAAGAATGGT ACCAAAGTTA
ACTTTCAAGT TCACCACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TCGAAAGAT
CCCAACGAAA AGAGAGACCA CATGGTCCTT CTTGAGTTTG TAACAGCTGC TGGGATTACA CATGGCATGG
ATGAACTATA CAAATAA
```

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG CCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG GAAACATTCT TGGACACAAA
TTGGAATACA ACTATAACCC TCACTGGGTG TACATCATGG CAGACAAACA AAAGAATGGA ATCAAAGTTA
ACTTCAAAAT TAGACACAAC ATTGAAGATG GAAGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

FIGURE 12G

Cypridina luciferase

```
ATGAAGATAA TAATTCTGTC TGTTATATTG GCCTACTGTG TCACCGTCAA CTGTCAAGAT GCATGTCCTG
TAGAAGCGGA ACCGCCATCA AGTACACCAA CAGTTCCAAC TTCTTGTGAA GCTAAAGAAG GAGAATGTAT
AGATACCAGA TGCGCAACAT GTAAACGAGA TATACTATCA GACGGACTGT GTGAAAATAA CCAGGGAAG
ACATGCTGTA GAATGTGCCA GTATGTGATT GAATGCAGAG TAGAAGCAGC TGGTTATTTT AGAACGTTTT
ACGGCAAAAG ATTTAATTTT CAGGAACCTG GTAAATATGT GCTGGCTAGG GGAACCAAGG GTGGCGATTG
GTCTGTAACC CTCACCATGG AGAACCTAGA TGGACAGAAG GGAGCTGTGC TGACTAAGAC AACACTGGAG
GTTGCAGGAG ACGTAATAGA CATTACTCAA GCTACTGCAG ATCCTATCAC AGTTAACGGA GGAGCTGACC
CAGTTATCGC TAACCCGTTC ACAATTGGTG AGGTGACCAT TGCTGTTGTT GAAATACCGG GCTTCAATAT
CACAGTCATC GAATTCTTTA AACTAATCGT GATTGATATT CTGGGAGGAA GATCTGTGAG AATTGCTCCA
GACACAGCAA ACAAAGGACT GATATCTGGT ATCTGTGGTA ATCTGGAGAT GAATGACGCT GATGACTTTA
CTACAGACGC AGATCAGCTG GCGATCCAAC CCAACATAAA CAAAGAGTTC GACGGCTGCC CATTCTATGG
GAATCCTTCT GATATCGAAT ACTGCAAAGG TCTCATGGAG CCATACAGAG CTGTATGTCG TAACAATATC
AACTTCTACT ATTACACTCT ATCCTGCGCC TTCGCTTACT GTATGGGAGG AGAAGAAAGA GCTAAACACG
TCCTTTTCGA CTATGTTGAG ACATGCGCTG CACCGGAAAC GAGAGGAACG TGTGTTTTAT CAGGACATAC
TTTCTATGAC ACATTCGACA AAGCCAGATA TCAATTCCAG GGCCCATGCA AAGAGCTTCT GATGGCCGCA
GACTGTTACT GGAACACATG GGATGTAAAG GTTTCACATA GAGATGTTGA GTCATACACT GAGGTAGAGA
AAGTAACAAT CAGGAAACAG TCAACTGTAG TAGATCTGAT TGTGGATGGC AAGCAGGTCA AGGTTGGAGG
AGTGGATGTA TCTATCCCGT ACAGCTCTGA GAACACATCC ATATACTGGC AGGATGGAGA CATCCTGACG
ACGGCCATCC TACCTGAAGC TCTCGTCGTT AAGTTCAACT TTAAGCAGCT CCTTGTAGTT CATATCAGAG
ATCCATTCGA TGGAAAGACA TGCGGCATAT GTGGTAACTA TAATCAAGAT TCAACTGATG ATTTCTTTGA
CGCAGAAGGA GCATGCGCTC TGACCCCCAA TCCCCCAGGA TGTACAGAGG AGCAGAAACC AGAAGCTGAG
CGACTCTGCA ATAGTCTATT TGATAGTTCT ATCGACGAGA ATGTAATGT CTGCTACAAG CCGGACCGTA
TTGCCCGATG TATGTACGAG TATTGCCTGA GGGGACAGCA AGGATTCTGT GACCATGCTT GGGAGTTCAA
GAAAGAATGC TACATAAAGC ATGGAGACAC TCTAGAAGTA CCACCTGAAT GTCAATAA
```

ATGATTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGATGATG GAAACATTCT TGGACACAAA
TTGGAATACA ACTATAACGA GCACTTGGTG TACATCATGG CAGACAAACA AAAGAATGGT ACCAAAGCTA
TCTTTCAAGT TCACCACAAC ATTGAAGATG GAGGCGTTCA ACTAGCAGAC CATTATCAAC AAAATACTCC
AATTGGCGAT GGCCCTGTCC TTTTACCAGA CAACCATTAC CTGCACACAC AATCTGCCCT TTCGAAAGAT
CCCAACGAAA AGAGAGACCA CATGGTCTTT CTTGAGTTTG TAACAGCTGC TGGGATTACA CATGGCATGG
ATGAAGTNTA CAAATAA

FIGURE 18 pC6

```
  1 MIKGEELFTG VVPILVELDG DVNGHKFSVS GEGEGDATYG KLTLKFICTT GKLPVPWPTL    60
 61 VTTFSYGVQC FSRYPDHMKR HDFFKSAMPE GYVQERTIFF KDDGNYKTRA EVKFEGDTLV   120
121 NRIELKGIDF KDDGNILGHK LEYNYNEHLV YIMADKQKNG TKAIFQVHHN IEDGGVQLAD   180
181 HYQQNTPIGD GPVLLPDNHY LHTQSALSKD PNEKRDHMVF LEFVTAAGIT HGMDEVYK.    239
```

ATGAGTAAAG GAGAAGAACT TTTCACTGGA GTTGTCCCAA TTCTTGTTGA ATTAGATGGT GATGTTAATG
GGCACAAATT TTCTGTCAGT GGAGAGGGTG AAGGTGATGC AACATACGGA AAACTTACCC TTAAATTTAT
TTGCACTACT GGAAAACTAC CTGTTCCATG GCCAACACTT GTCACTACTT TCTCTTATGG TGTTCAATGC
TTTTCAAGAT ACCCAGATCA TATGAAACGG CATGACTTTT TCAAGAGTGC CATGCCCGAA GGTTATGTAC
AGGAAAGAAC TATATTTTTC AAAGATGACG GGAACTACAA GACACGTGCT GAAGTCAAGT TTGAAGGTGA
TACCCTTGTT AATAGAATCG AGTTAAAAGG TATTGATTTT AAAGAAGATG AAACATTCT TGGACACAAA
TTGGAATACA ACTATAACGA TCACCAGGTG TACATCATGG CAGACAAACA AAAGAATGGA ATCAAAGCTA
ACTTCAAAAT TAGACACAAC ATTGAAGATG GAGGCGTTCA ACTAGCAGAC CATTATCAAC AAAATACTCC
AATTGGCGAT GGGCCCGTCC TTTTACCAGA CAACCATTAC CTGTTTACAA CTTCTACTCT TTCGAAAGAT
CCCAACGAAA AGAGAGACCA CATGGTCCTT CTTGAGTTTG TAACAGCTGC TGGGATTACA CATGGCATGG
ATGAACTATA CAAATAA

FIGURE 20 p8F3

```
  1 MSKGEELFTG VVPILVELDG DVNGHKFSVS GEGEGDATYG KLTLKFICTT GKLPVPWPTL    60
 61 VTTFSYGVQC FSRYPDHMKR HDFFKSAMPE GYVQERTIFF KDDGNYKTRA EVKFEGDTLV   120
121 NRIELKGIDF KEDGNILGHK LEYNYNDHQV YIMADKQKNG IKANFKIRHN IEDGGVQLAD   180
181 HYQQNTPIGD GPVLLPDNHY LFTTSTLSKD PNEKRDHMVL LEFVTAAGIT HGMDELYK.    239
```

FIGURE 21 p1B11t

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNDHQV YIMADKQKNG IKANFKIRHN IEDGGVQLAD  180
181 HYQQNTPIGD GPVLLPDNHY LHTQSALSKD PNEKRDHMVL LEFVTAAGIT HGMDELYK.   239
```

FIGURE 22 p14E12t

```
  1 MSKGEELFTG VVPILVELDG DVNGHKFSVS GEGEGDATYG KLTLKFICTT GKLPVPWPTL    60
 61 VTTFSYGVQC FSRYPDHMKR HDFFKSAMPE GYVQERTIFF KDDGNYKTRA EVKFEGDTLV   120
121 NRIELKGIDF KEDGNILGHK LEYNYNDHDV YIMADKQKNG TKANFQVRHN IEDGGVQLAD   180
181 HYQQNTPIGD GPVLLPDNHY LHTQSALSKD PNEKRDHMVL LEFVTAAGIT HGMDELYK.    239
```

FIGURE 23 p1D10

```
  1 MSKGEELFTG VVPILVELDG DVNGHKFSVS GEGEGDATYG KLTLKFICTT GKLPVPWPTL    60
 61 VTTFSYGVQC FSRYPDHMKR HDFFKSAMPE GYVQERTIFF KDDGNYKTRA EVKFEGDTLV   120
121 NRIELKGIDF KEDGNILGHK LEYNYNDHNV YIMADKQKNG IKVNFKIRHN IEDGSVQLAD   180
181 HYQQNTPIGD GPVLLPDNHY LHTQSALSKD PNEKRDHMVL LEFVTAAGIT HGMDELYK.    239
```

FIGURE 24 p2F10

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNDHHV YIMADKQKNG IKVNFKIRHN IEDGSVQLAD  180
181 HYQQNTPIGD GPVLLPDNHY LHTQSALSKD PNEKRDHMVL LEFVTAAGIT HGMDELYK.   239
```

FIGURE 25 p2H2

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNDHVV YIMADKQKNG IKVNFKIRHN IEDGSVQLAD  180
181 HYQQNTPIGD GPVLLPDNHY LHTQSALSKD PNEKRDHMVL LEFVTAAGIT HGMDELYK.   239
```

FIGURE 26 p1B11

```
  1 MSKGEELFTG VVPILVELDG DVNGHKFSVS GEGEGDATYG KLTLKFICTT GKLPVPWPTL    60
 61 VTTFSYGVQC FSRYPDHMKR HDFFKSAMPE GYVQERTIFF KDDGNYKTRA EVKFEGDTLV   120
121 NRIELKGIDF KEDGNILGHK LEYNYNDHQV YIMADKQKNG IKVNFKIRHN IEDGSVQLAD   180
181 HYQQNTPIGD GPVLLPDNHY LHTQSALSKD PNEKRDHMVL LEFVTAAGIT HGMDELYK.    239
```

FIGURE 27 p8F6

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNDHTV YIMADKQKNG IKVNFKIRHN IEDGSVQLAD  180
181 HYQQNTPIGD GPVLLPDNHY LHTQSALSKD PNEKRDHMVL LEFVTAAGIT HGMDELYK.   239
```

FIGURE 28 p19E10

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNDHLV YIMADKQKNG TKVNFQVHHN IEDGSVQLAD  180
181 HYQQNTPIGD GPVLLPDNHY LHTQSALSKD PNEKRDHMVL LEFVTAAGIT HGMDELYK.   239
```

FIGURE 29 p14E12

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNDHDV YIMADKQKNG TKVNFQVRHN IEDGSVQLAD  180
181 HYQQNTPIGD GPVLLPDNHY LHTQSALSKD PNEKRDHMVL LEFVTAAGIT HGMDELYK.   239
```

FIGURE 30 p14C9

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNDHLV YIMADKQKNG TKVNFQVRHN IEDGSVQLAD  180
181 HYQQNTPIGD GPVLLPDNHY LHTQSALSKD PNEKRDHMVL LEFVTAAGIT HGMDELYK.   239
```

FIGURE 31

```
P14c8    1  MSKGEELFTG VVPILVELDG DVNGHKFSVS GEGEGDATYG KLTLKFICTT GKLPVPWPTL   60
            VTTFSYGVQC FSRYPDHMKR HDFFKSAMPE GYVQERTIFF KDDGNYKTRA EVKFEGDTLV  120
            NRIELKGIDF KEDGNILGHK LEYNYNPHYV YIMADKQKNG TKVNFQVHHN IEDGSVQLAD  180
            HYQQNTPIGD GPVLLPDNHY LHTQSALSKD PNEKRDHMVL LEFVTAAGIT HGMDELYK
```

FIG. 32 p2G3

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNEHLV YIMADKQKNG TKANFKIHHN IEDGGVQLAD  180
181 HYQQNTPIGD GPVLLPDNHY LHTQSALSKD PNEKRDHMVL LEFVTAAGIT HGMDELYK.   239
```

FIGURE 33 pS202H

```
  1 MSKGEELFTG VVPILVELDG DVNGHKFSVS GEGEGDATYG KLTLKFICTT GKLPVPWPTL    60
 61 VTTFSYGVQC FSRYPDHMKR HDFFKSAMPE GYVQERTIFF KDDGNYKTRA EVKFEGDTLV   120
121 NRIELKGIDF KEDGNILGHK LEYNYNSHNV YIMADKQKNG IKVNFKIRHN IEDGSVQLAD   180
181 HYQQNTPIGD GPVLLPDNHY LHTQSALSKD PNEKRDHMVL LEFVTAAGIT HGMDELYK.    239
```

FIGURE 34 p8H8

```
  1 MSKGEELFTG VVPILVELDG DVNGHKFSVS GEGEGDATYG KLTLKFICTT GKLPVPWPTL   60
 61 VTTFSYGVQC FSRYPDHMKR HDFFKSAMPE GYVQERTIFF KDDGNYKTRA EVKFEGDTLV  120
121 NRIELKGIDF KEDGNILGHK LEYNYNPHWV YIMADKQKNG IKVNFKIRHN IEDGSVQLAD  180
181 HYQQNTPIGD GPVLLPDNHY LHTQSALSKD PNEKRDHMVL LEFVTAAGIT HGMDELYK.   239
```

FIGURE 35

SEQUENCE LISTING (1) GENERAL INFORMATION:

(iii) NUMBER OF SEQUENCES: 39

(2) INFORMATION FOR SEQ ID NO: 1:

(i) SEQUENCE CHARACTERISTICS:
        (A) LENGTH: 242
        (B) TYPE: AMINO ACID
        (C) STRANDEDNESS: UNKNOWN
        (D) TOPOLOGY: LINEAR (ii) MOLECULE TYPE: PROTEIN (ix) FEATURE:
        (A) NAME/KEY:  GREEN FLUORESCENT PROTEIN (xi) SEQUENCE DESCRIPTION: SEQ ID NO: 1:

Met Gly Lys Gly Glu Glu Leu Phe Thr Gly Val Val
 1               5                  10

Pro Ile Leu Val Glu Leu Asp Gly Asp Val Asn Gly

```
              15                  20
His Lys Phe Ser Val Ser Gly Glu Gly Glu Gly Asp
 25                      30                  35

Ala Thr Tyr Gly Lys Leu Thr Leu Lys Phe Ile Cys
             40                  45

Thr Thr Gly Lys Leu Pro Val Pro Trp Pro Thr Leu
 50                      55                  60

Val Thr Thr Phe Ser Tyr Gly Val Gln Cys Phe Ser
             65                  70

Arg Tyr Pro Asp His Met Lys Arg His Asp Phe Phe
         75                  80

Lys Ser Ala Met Pro Glu Gly Tyr Val Gln Glu Arg
 85                      90                  95

Thr Ile Phe Phe Lys Asp Asp Gly Asn Tyr Lys Thr
             100                 105

Arg Ala Glu Val Lys Phe Glu Gly Asp Thr Leu Val
 110                     115                 120

Asn Arg Ile Glu Leu Lys Gly Ile Asp Phe Lys Glu
             125                 130

Asp Gly Asn Ile Leu Gly His Lys Leu Glu Tyr Asn
         135                 140

Tyr Asn Ser His Asn Val Tyr Ile Met Ala Asp Lys
145                      150                 155

Gln Lys Asn Gly Thr Lys Val Asn Phe Lys Ile Arg
             160                 165

His Asn Ile Glu Asp Gly Ser Val Gln Leu Ala Asp
 170                     175                 180

His Tyr Gln Gln Asn Thr Pro Ile Gly Asp Gly Pro
             185                 190

Val Leu Leu Pro Asp Asn His Tyr Leu Ser Thr Gln
             195                 200

Ser Ala Leu Ser Lys Asp Pro Asn Glu Lys Arg Asp
205                      210                 215

His Met Val Leu Leu Glu Phe Val Thr Ala Ala Gly
             220                 225

Ile Thr His Gly Met Asp Glu Leu Tyr Lys Ser Gly
 230                     235                 240

Ser Arg (2) INFORMATION FOR SEQ ID NO: 2:

(i) SEQUENCE CHARACTERISTICS:
        (A) LENGTH: 729
        (B) TYPE: NUCLEIC ACID
        (C) STRANDEDNESS: UNKNOWN
        (D) TOPOLOGY: UNKNOWN (xi) SEQUENCE DESCRIPTION: SEQ ID NO: 2:

ATGGGTAAAG GAGAAGAACT TTTCACTGGA GTTGTCCCAA                    40

TTCTTGTTGA ATTAGATGGT GATGTTAATG GGCACAAATT                    80

TTCTGTCAGT GGAGAGGGTG AAGGTGATGC AACATACGGA                   120

AAACTTACCC TTAAATTTAT TTGCACTACT GGAAAACTAC                   160

CTGTTCCATG GCCAACACTT GTCACTACTT TCTCTTATGG                   200
```

| | |
|---|---|
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GAACTACAA | 320 |
| GACACGTGCT GAAGTCAAGT TTGAAGGTGA TACCCTTGTT | 360 |
| AATAGAATCG AGTTAAAAGG TATTGATTTT AAAGAAGATG | 400 |
| GAAACATTCT TGGACACAAA TTGGAATACA ACTATAACTC | 440 |
| ACACAATGTA TACATCATGG CAGACAAACA AAAGAATGGA | 480 |
| ACCAAAGTTA ACTTCAAAAT TAGACACAAC ATTGAAGATG | 520 |
| GAAGCGTTCA ACTAGCAGAC CATTATCAAC AAAATACTCC | 560 |
| AATTGGCGAT GGCCCTGTCC TTTTACCAGA CAACCATTAC | 600 |
| CTGTCCACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAGTCCGGA | 720 |
| TCTAGATAA | 729 |

(2) INFORMATION FOR SEQ ID NO: 3:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (xi) SEQUENCE DESCRIPTION: SEQ ID NO: 3:

| | |
|---|---|
| ATGAGTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GAACTACAA | 320 |
| GACACGTGCT GAAGTCAAGT TTGAAGGTGA TACCCTTGTT | 360 |
| AATAGAATCG AGTTAAAAGG TATTGATTTT AAAGAAGATG | 400 |
| GAAACATTCT TGGACACAAA TTGGAATACA ACTATAACGA | 440 |
| TCACCAGGTG TACATCATGG CAGACAAACA AAAGAATGGA | 480 |
| ATCAAAGCTA ACTTCAAAAT TAGACACAAC ATTGAAGATG | 520 |
| GAGGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAATAA | 717 |

(2) INFORMATION FOR SEQ ID NO: 4:

(i) SEQUENCE CHARACTERISTICS:

(A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 14E12t (xi) SEQUENCE DESCRIPTION: SEQ ID NO: 4:

| | |
|---|---|
| ATGAGTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATTG AGTTAAAAGG TATTGATTTT AAAGAAGATG | 400 |
| GAAACATTCT TGGACACAAA TTGGAGTACA ACTATAACGA | 440 |
| TCACGATGTG TACATCATGG CAGACAAACA AAAGAATGGT | 480 |
| ACCAAAGCTA ACTTTCAAGT TCGCCACAAC ATTGAAGATG | 520 |
| GAGGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAATAA | 717 |

(2) INFORMATION FOR SEQ ID NO: 5:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 1D10

(xi) SEQUENCE DESCRIPTION: SEQ ID NO: 5:

| | |
|---|---|
| ATGAGTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATCG AGTTAAAAGG TATTGATTTT AAAGAAGATG | 400 |

```
GAAACATTCT TGGACACAAA TTGGAATACA ACTATAACGA         440

TCACAATGTG TACATCATGG CAGACAAACA AAAGAATGGA         480

ATCAAAGTTA ACTTCAAAAT TAGACACAAC ATTGAAGATG         520

GAAGCGTTCA ACTAGCAGAC CATTATCAAC AAAATACTCC         560

AATTGGCGAT GGCCCTGTCC TTTTACCAGA CAACCATTAC         600

CTGCACACAC AATCTGCCCT TTCGAAAGAT CCCAACGAAA         640

AGAGAGACCA CATGGTCCTT CTTGAGTTTG TAACAGCTGC         680

TGGGATTACA CATGGCATGG ATGAACTATA CAAATAA           717
```

(2) INFORMATION FOR SEQ ID NO: 6:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 2F10

(xi) SEQUENCE DESCRIPTION: SEQ ID NO: 6:

```
ATGAGTAAAG GAGAAGAACT TTTCACTGGA GTTGTCCCAA          40

TTCTTGTTGA ATTAGATGGT GATGTTAATG GGCACAAATT          80

TTCTGTCAGT GGAGAGGGTG AAGGTGATGC AACATACGGA         120

AAACTTACCC TTAAATTTAT TTGCACTACT GGAAAACTAC         160

CTGTTCCATG GCCAACACTT GTCACTACTT TCTCTTATGG         200

TGTTCAATGC TTTTCAAGAT ACCCAGATCA TATGAAACGG         240

CATGACTTTT TCAAGAGTGC CATGCCCGAA GGTTATGTAC         280

AGGAAAGAAC TATATTTTTC AAAGATGACG GGAACTACAA         320

GACACGTGCT GAAGTCAAGT TTGAAGGTGA TACCCTTGTT         360

AATAGAATCG AGTTAAAAGG TATTGATTTT AAAGAAGATG         400

GAAACATTCT TGGACACAAA TTGGAATACA ACTATAACGA         440

TCACCATGTG TACATCATGG CAGACAAACA AAAGAATGGA         480

ATCAAAGTTA ACTTCAAAAT TAGACACAAC ATTGAAGATG         520

GAAGCGTTCA ACTAGCAGAC CATTATCAAC AAAATACTCC         560

AATTGGCGAT GGCCCTGTCC TTTTACCAGA CAACCATTAC         600

CTGCACACAC AATCTGCCCT TTCGAAAGAT CCCAACGAAA         640

AGAGAGACCA CATGGTCCTT CTTGAGTTTG TAACAGCTGC         680

TGGGATTACA CATGGCATGG ATGAACTATA CAAATAA           717
```

(2) INFORMATION FOR SEQ ID NO: 7:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 2H2

(xi) SEQUENCE DESCRIPTION: SEQ ID NO: 7:

```
ATGAGTAAAG GAGAAGAACT TTTCACTGGA GTTGTCCCAA                40
TTCTTGTTGA ATTAGATGGT GATGTTAATG GGCACAAATT                80
TTCTGTCAGT GGAGAGGGTG AAGGTGATGC AACATACGGA               120
AAACTTACCC TTAAATTTAT TTGCACTACT GGAAAACTAC               160
CTGTTCCATG CCAACACTT GTCACTACTT TCTCTTATGG                200
TGTTCAATGC TTTTCAAGAT ACCCAGATCA TATGAAACGG               240
CATGACTTTT TCAAGAGTGC CATGCCCGAA GGTTATGTAC               280
AGGAAAGAAC TATATTTTTC AAAGATGACG GGAACTACAA               320
GACACGTGCT GAAGTCAAGT TTGAAGGTGA TACCCTTGTT               360
AATAGAATCG AGTTAAAAGG TATTGATTTT AAAGAAGATG               400
GAAACATTCT TGGACACAAA TTGGAATACA ACTATAACGA               440
TCACGTGGTG TACATCATGG CAGACAAACA AAAGAATGGA               480
ATCAAAGTTA ACTTCAAAAT TAGACACAAC ATTGAAGATG               520
GAAGCGTTCA ACTAGCAGAC CATTATCAAC AAAATACTCC               560
AATTGGCGAT GGCCCTGTCC TTTTACCAGA CAACCATTAC               600
CTGCACACAC AATCTGCCCT TTCGAAAGAT CCCAACGAAA               640
AGAGAGACCA CATGGTCCTT CTTGAGTTTG TAACAGCTGC               680
TGGGATTACA CATGGCATGG ATGAACTATA CAAATAA                  717
```

(2) INFORMATION FOR SEQ ID NO: 8:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 1B11

(xi) SEQUENCE DESCRIPTION: SEQ ID NO: 8:

```
ATGAGTAAAG GAGAAGAACT TTTCACTGGA GTTGTCCCAA                40
TTCTTGTTGA ATTAGATGGT GATGTTAATG GGCACAAATT                80
TTCTGTCAGT GGAGAGGGTG AAGGTGATGC AACATACGGA               120
AAACTTACCC TTAAATTTAT TTGCACTACT GGAAAACTAC               160
CTGTTCCATG CCAACACTT GTCACTACTT TCTCTTATGG                200
TGTTCAATGC TTTTCAAGAT ACCCAGATCA TATGAAACGG               240
CATGACTTTT TCAAGAGTGC CATGCCCGAA GGTTATGTAC               280
AGGAAAGAAC TATATTTTTC AAAGATGACG GGAACTACAA               320
GACACGTGCT GAAGTCAAGT TTGAAGGTGA TACCCTTGTT               360
AATAGAATCG AGTTAAAAGG TATTGATTTT AAAGAAGATG               400
GAAACATTCT TGGACACAAA TTGGAATACA ACTATAACGA               440
TCACCAGGTG TACATCATGG CAGACAAACA AAAGAATGGA               480
ATCAAAGTTA ACTTCAAAAT TAGACACAAC ATTGAAGATG               520
GAAGCGTTCA ACTAGCAGAC CATTATCAAC AAAATACTCC               560
```

```
AATTGGCGAT GGCCCTGTCC TTTTACCAGA CAACCATTAC                600

CTGCACACAC AATCTGCCCT TTCGAAAGAT CCCAACGAAA                640

AGAGAGACCA CATGGTCCTT CTTGAGTTTG TAACAGCTGC                680

TGGGATTACA CATGGCATGG ATGAACTATA CAAATAA                   717

(2) INFORMATION FOR SEQ ID NO: 9:

(i) SEQUENCE CHARACTERISTICS:
         (A) LENGTH: 717
         (B) TYPE: NUCLEIC ACID
         (C) STRANDEDNESS: UNKNOWN
         (D) TOPOLOGY: UNKNOWN (ix) FEATURE:
         (A) NAME/KEY:  8F6

(xi) SEQUENCE DESCRIPTION: SEQ ID NO: 9:

ATGAGTAAAG GAGAAGAACT TTTCACTGGA GTTGTCCCAA                 40

TTCTTGTTGA ATTAGATGGT GATGTTAATG GGCACAAATT                 80

TTCTGTCAGT GGAGAGGGTG AAGGTGATGC AACATACGGA                120

AAACTTACCC TTAAATTTAT TTGCACTACT GGAAAACTAC                160

CTGTTCCATG GCCAACACTT GTCACTACTT TCTCTTATGG                200

TGTTCAATGC TTTTCAAGAT ACCCAGATCA TATGAAACGG                240

CATGACTTTT TCAAGAGTGC CATGCCCGAA GGTTATGTAC                280

AGGAAAGAAC TATATTTTTC AAAGATGACG GGAACTACAA                320

GACACGTGCT GAAGTCAAGT TTGAAGGTGA TACCCTTGTT                360

AATAGAATCG AGTTAAAAGG TATTGATTTT AAAGAAGATG                400

GAAACATTCT TGGACACAAA TTGGAATACA ACTATAACGA                440

TCACACTGTG TACATCATGG CAGACAAACA AAAGAATGGA                480

ATCAAAGTTA ACTTCAAAAT TAGACACAAC ATTGAAGATG                520

GAAGCGTTCA ACTAGCAGAC CATTATCAAC AAAATACTCC                560

AATTGGCGAT GGCCCTGTCC TTTTACCAGA CAACCATTAC                600

CTGCACACAC AATCTGCCCT TTCGAAAGAT CCCAACGAAA                640

AGAGAGACCA CATGGTCCTT CTTGAGTTTG TAACAGCTGC                680

TGGGATTACA CATGGCATGG ATGAACTATA CAAATAA                   717

(2) INFORMATION FOR SEQ ID NO: 10:

(i) SEQUENCE CHARACTERISTICS:
         (A) LENGTH: 717
         (B) TYPE: NUCLEIC ACID
         (C) STRANDEDNESS: UNKNOWN
         (D) TOPOLOGY: UNKNOWN (ix) FEATURE:
         (A) NAME/KEY:  19E10

(xi) SEQUENCE DESCRIPTION: SEQ ID NO: 10:

ATGAGTAAAG GAGAAGAACT TTTCACTGGA GTTGTCCCAA                 40

TTCTTGTTGA ATTAGATGGT GATGTTAATG GGCACAAATT                 80

TTCTGTCAGT GGAGAGGGTG AAGGTGATGC AACATACGGA                120
```

```
AAACTTACCC TTAAATTTAT TTGCACTACT GGAAAACTAC                  160

CTGTTCCATG GCCAACACTT GTCACTACTT TCTCTTATGG                  200

TGTTCAATGC TTTTCAAGAT ACCCAGATCA TATGAAACGG                  240

CATGACTTTT TCAAGAGTGC CATGCCCGAA GGTTATGTAC                  280

AGGAAAGAAC TATATTTTTC AAAGATGACG GAACTACAA                   320

GACACGTGCT GAAGTCAAGT TTGAAGGTGA TACCCTTGTT                  360

AATAGAATTG AGTTAAAAGG TATTGATTTT AAAGAAGATG                  400

GAAACATTCT TGGACACAAA TTGGAGTACA ACTATAACGA                  440

TCACTTGGTG TACATCATGG CAGACAAACA AAAGAATGGT                  480

ACCAAAGTTA ACTTTCAAGT TCACCACAAC ATTGAAGATG                  520

GAAGCGTTCA ACTAGCAGAC CATTATCAAC AAAATACTCC                  560

AATTGGCGAT GGCCCTGTCC TTTTACCAGA CAACCATTAC                  600

CTGCACACAC AATCTGCCCT TTCGAAAGAT CCCAACGAAA                  640

AGAGAGACCA CATGGTCCTT CTTGAGTTTG TAACAGCTGC                  680

TGGGATTACA CATGGCATGG ATGAACTATA CAAATAA                     717
```

(2) INFORMATION FOR SEQ ID NO: 11:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 14E12

(xi) SEQUENCE DESCRIPTION: SEQ ID NO: 11:

```
ATGAGTAAAG GAGAAGAACT TTTCACTGGA GTTGTCCCAA                   40

TTCTTGTTGA ATTAGATGGT GATGTTAATG GGCACAAATT                   80

TTCTGTCAGT GGAGAGGGTG AAGGTGATGC AACATACGGA                  120

AAACTTACCC TTAAATTTAT TTGCACTACT GGAAAACTAC                  160

CTGTTCCATG GCCAACACTT GTCACTACTT TCTCTTATGG                  200

TGTTCAATGC TTTTCAAGAT ACCCAGATCA TATGAAACGG                  240

CATGACTTTT TCAAGAGTGC CATGCCCGAA GGTTATGTAC                  280

AGGAAAGAAC TATATTTTTC AAAGATGACG GAACTACAA                   320

GACACGTGCT GAAGTCAAGT TTGAAGGTGA TACCCTTGTT                  360

AATAGAATTG AGTTAAAAGG TATTGATTTT AAAGAAGATG                  400

GAAACATTCT TGGACACAAA TTGGAGTACA ACTATAACGA                  440

TCACGATGTG TACATCATGG CAGACAAACA AAAGAATGGT                  480

ACCAAAGTTA ACTTTCAAGT TCGCCACAAC ATTGAAGATG                  520

GAAGCGTTCA ACTAGCAGAC CATTATCAAC AAAATACTCC                  560

AATTGGCGAT GGCCCTGTCC TTTTACCAGA CAACCATTAC                  600

CTGCACACAC AATCTGCCCT TTCGAAAGAT CCCAACGAAA                  640

AGAGAGACCA CATGGTCCTT CTTGAGTTTG TAACAGCTGC                  680

TGGGATTACA CATGGCATGG ATGAACTATA CAAATAA                     717
```

(2) INFORMATION FOR SEQ ID NO: 12:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 14C9

(xi) SEQUENCE DESCRIPTION: SEQ ID NO: 12:

```
ATGAGTAAAG GAGAAGAACT TTTCACTGGA GTTGTCCCAA                    40
TTCTTGTTGA ATTAGATGGT GATGTTAATG GGCACAAATT                    80
TTCTGTCAGT GGAGAGGGTG AAGGTGATGC AACATACGGA                   120
AAACTTACCC TTAAATTTAT TTGCACTACT GGAAAACTAC                   160
CTGTTCCATG GCCAACACTT GTCACTACTT TCTCTTATGG                   200
TGTTCAATGC TTTTCAAGAT ACCCAGATCA TATGAAACGG                   240
CATGACTTTT TCAAGAGTGC CATGCCCGAA GGTTATGTAC                   280
AGGAAAGAAC TATATTTTTC AAAGATGACG GAACTACAA                    320
GACACGTGCT GAAGTCAAGT TTGAAGGTGA TACCCTTGTT                   360
AATAGAATTG AGTTAAAAGG TATTGATTTT AAAGAAGATG                   400
GAAACATTCT TGGACACAAA TTGGAGTACA ACTATAACGA                   440
TCACCTGGTG TACATCATGG CAGACAAACA AAAGAATGGT                   480
ACCAAAGTTA ACTTTCAAGT TCGCCACAAC ATTGAAGATG                   520
GAAGCGTTCA ACTAGCAGAC CATTATCAAC AAAATACTCC                   560
AATTGGCGAT GGCCCTGTCC TTTTACCAGA CAACCATTAC                   600
CTGCACACAC AATCTGCCCT TTCGAAAGAT CCCAACGAAA                   640
AGAGAGACCA CATGGTCCTT CTTGAGTTTG TAACAGCTGC                   680
TGGGATTACA CATGGCATGG ATGAACTATA CAAATAA                      717
```

(2) INFORMATION FOR SEQ ID NO: 13:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 14C8

(xi) SEQUENCE DESCRIPTION: SEQ ID NO: 13:

```
ATGAGTAAAG GAGAAGAACT TTTCACTGGA GTTGTCCCAA                    40
TTCTTGTTGA ATTAGATGGT GATGTTAATG GGCACAAATT                    80
TTCTGTCAGT GGAGAGGGTG AAGGTGATGC AACATACGGA                   120
AAACTTACCC TTAAATTTAT TTGCACTACT GGAAAACTAC                   160
CTGTTCCATG GCCAACACTT GTCACTACTT TCTCTTATGG                   200
TGTTCAATGC TTTTCAAGAT ACCCAGATCA TATGAAACGG                   240
CATGACTTTT TCAAGAGTGC CATGCCCGAA GGTTATGTAC                   280
```

-continued

| | |
|---|---|
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATTG AGTTAAAAGG TATTGATTTT AAAGAAGATG | 400 |
| GAAACATTCT TGGACACAAA TTGGAGTACA ACTATAACCC | 440 |
| TCACTATGTG TACATCATGG CAGACAAACA AAAGAATGGT | 480 |
| ACCAAAGTTA ACTTTCAAGT TCACCACAAC ATTGAAGATG | 520 |
| GAAGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAATAA | 717 |

(2) INFORMATION FOR SEQ ID NO: 14:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 2G3

(xi) SEQUENCE DESCRIPTION: SEQ ID NO: 14:

| | |
|---|---|
| ATGAGTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATCG AGTTAAAAGG TATTGATTTT AAAGAAGATG | 400 |
| GAAACATTCT TGGACACAAA TTGGAATACA ACTATAACGA | 440 |
| GCACTTGGTG TACATCATGG CAGACAAACA AAAGAATGGT | 480 |
| ACCAAAGCTA ACTTTAAAAT TCACCACAAC ATTGAAGATG | 520 |
| GAGGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAATAA | 717 |

(2) INFORMATION FOR SEQ ID NO: 15:

(i) SEQUENCE CHARACTERISTICS:
        (A) LENGTH: 717
        (B) TYPE: NUCLEIC ACID
        (C) STRANDEDNESS: UNKNOWN (D) TOPOLOGY: UNKNOWN (ix) FEATURE:
        (A) NAME/KEY: S202H (xi) SEQUENCE DESCRIPTION: SEQ ID NO: 15:

| | |
|---|---|
| ATGAGTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATCG AGTTAAAAGG TATTGATTTT AAAGAAGATG | 400 |
| GAAACATTCT TGGACACAAA TTGGAATACA ACTATAACTC | 440 |
| ACACAATGTA TACATCATGG CAGACAAACA AAAGAATGGA | 480 |
| ATCAAAGTTA ACTTCAAAAT TAGACACAAC ATTGAAGATG | 520 |
| GAAGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAATAA | 717 |

(2) INFORMATION FOR SEQ ID NO: 16:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 14D9

(xi) SEQUENCE DESCRIPTION: SEQ ID NO: 16:

| | |
|---|---|
| ATGAGTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATTG AGTTAAAAGG TATTGATTTT AAAGAAGATG | 400 |
| GAAACATTCT TGGACACAAA TTGGAGTACA ACTATAACCC | 440 |

| | |
|---|---|
| TCACTGGGTG TACATCATGG CAGACAAACA AAAGAATGGT | 480 |
| ACCAAAGTTA ACTTTCAAGT TCACCACAAC ATTGAAGATG | 520 |
| GAAGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAATAA | 717 |

(2) INFORMATION FOR SEQ ID NO: 17:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: 8H8

(xi) SEQUENCE DESCRIPTION: SEQ ID NO: 17:

| | |
|---|---|
| ATGAGTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATCG AGTTAAAAGG TATTGATTTT AAAGAAGATG | 400 |
| GAAACATTCT TGGACACAAA TTGGAATACA ACTATAACCC | 440 |
| TCACTGGGTG TACATCATGG CAGACAAACA AAAGAATGGA | 480 |
| ATCAAAGTTA ACTTCAAAAT TAGACACAAC ATTGAAGATG | 520 |
| GAAGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCCTT CTTGAGTTTG TAACAGCTGC | 680 |
| TGGGATTACA CATGGCATGG ATGAACTATA CAAATAA | 717 |

(2) INFORMATION FOR SEQ ID NO: 18:

(i) SEQUENCE CHARACTERISTICS:
        (A) LENGTH: 1668
        (B) TYPE: NUCLEIC ACID
        (C) STRANDEDNESS: UNKNOWN
        (D) TOPOLOGY: UNKNOWN (ix) FEATURE:
        (A) NAME/KEY: CYPRIDINA LUCIFERASE (xi) SEQUENCE DESCRIPTION: SEQ ID NO: 18:

| | |
|---|---|
| ATGAAGATAA TAATTCTGTC TGTTATATTG GCCTACTGTG | 40 |

-continued

| | |
|---|---|
| TCACCGTCAA CTGTCAAGAT GCATGTCCTG TAGAAGCGGA | 80 |
| ACCGCCATCA AGTACACCAA CAGTTCCAAC TTCTTGTGAA | 120 |
| GCTAAAGAAG GAGAATGTAT AGATACCAGA TGCGCAACAT | 160 |
| GTAAACGAGA TATACTATCA GACGGACTGT GTGAAAATAA | 200 |
| ACCAGGGAAG ACATGCTGTA GAATGTGCCA GTATGTGATT | 240 |
| GAATGCAGAG TAGAAGCAGC TGGTTATTTT AGAACGTTTT | 280 |
| ACGGCAAAAG ATTTAATTTT CAGGAACCTG GTAAATATGT | 320 |
| GCTGGCTAGG GGAACCAAGG GTGGCGATTG GTCTGTAACC | 360 |
| CTCACCATGG AGAACCTAGA TGGACAGAAG GGAGCTGTGC | 400 |
| TGACTAAGAC AACACTGGAG GTTGCAGGAG ACGTAATAGA | 440 |
| CATTACTCAA GCTACTGCAG ATCCTATCAC AGTTAACGGA | 480 |
| GGAGCTGACC CAGTTATCGC TAACCCGTTC ACAATTGGTG | 520 |
| AGGTGACCAT TGCTGTTGTT GAAATACCGG GCTTCAATAT | 560 |
| CACAGTCATC GAATTCTTTA AACTAATCGT GATTGATATT | 600 |
| CTGGGAGGAA GATCTGTGAG AATTGCTCCA GACACAGCAA | 640 |
| ACAAAGGACT GATATCTGGT ATCTGTGGTA ATCTGGAGAT | 680 |
| GAATGACGCT GATGACTTTA CTACAGACGC AGATCAGCTG | 720 |
| GCGATCCAAC CCAACATAAA CAAAGAGTTC GACGGCTGCC | 760 |
| CATTCTATGG GAATCCTTCT GATATCGAAT ACTGCAAAGG | 800 |
| TCTCATGGAG CCATACAGAG CTGTATGTCG TAACAATATC | 840 |
| AACTTCTACT ATTACACTCT ATCCTGCGCC TTCGCTTACT | 880 |
| GTATGGGAGG AGAAGAAAGA GCTAAACACG TCCTTTTCGA | 920 |
| CTATGTTGAG ACATGCGCTG CACCGGAAAC GAGAGGAACG | 960 |
| TGTGTTTTAT CAGGACATAC TTTCTATGAC ACATTCGACA | 1000 |
| AAGCCAGATA TCAATTCCAG GGCCCATGCA AAGAGCTTCT | 1040 |
| GATGGCCGCA GACTGTTACT GGAACACATG GGATGTAAAG | 1080 |
| GTTTCACATA GAGATGTTGA GTCATACACT GAGGTAGAGA | 1120 |
| AAGTAACAAT CAGGAAACAG TCAACTGTAG TAGATCTGAT | 1160 |
| TGTGGATGGC AAGCAGGTCA AGGTTGGAGG AGTGGATGTA | 1200 |
| TCTATCCCGT ACAGCTCTGA GAACACATCC ATATACTGGC | 1240 |
| AGGATGGAGA CATCCTGACG ACGGCCATCC TACCTGAAGC | 1280 |
| TCTCGTCGTT AAGTTCAACT TTAAGCAGCT CCTTGTAGTT | 1320 |
| CATATCAGAG ATCCATTCGA TGGAAAGACA TGCGGCATAT | 1360 |
| GTGGTAACTA TAATCAAGAT TCAACTGATG ATTTCTTTGA | 1400 |
| CGCAGAAGGA GCATGCGCTC TGACCCCAA TCCCCCAGGA | 1440 |
| TGTACAGAGG AGCAGAAACC AGAAGCTGAG CGACTCTGCA | 1480 |
| ATAGTCTATT TGATAGTTCT ATCGACGAGA AATGTAATGT | 1520 |
| CTGCTACAAG CCGGACCGTA TTGCCCGATG TATGTACGAG | 1560 |
| TATTGCCTGA GGGGACAGCA AGGATTCTGT GACCATGCTT | 1600 |

| | |
|---|---|
| GGGAGTTCAA GAAAGAATGC TACATAAAGC ATGGAGACAC | 1640 |
| TCTAGAAGTA CCACCTGAAT GTCAATAA | 1668 |

(2) INFORMATION FOR SEQ ID NO: 19:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (ix) FEATURE:
        (A) NAME/KEY: C6

(xi) SEQUENCE DESCRIPTION: SEQ ID NO: 19:

| | |
|---|---|
| ATGATTAAAG GAGAAGAACT TTTCACTGGA GTTGTCCCAA | 40 |
| TTCTTGTTGA ATTAGATGGT GATGTTAATG GGCACAAATT | 80 |
| TTCTGTCAGT GGAGAGGGTG AAGGTGATGC AACATACGGA | 120 |
| AAACTTACCC TTAAATTTAT TTGCACTACT GGAAAACTAC | 160 |
| CTGTTCCATG GCCAACACTT GTCACTACTT TCTCTTATGG | 200 |
| TGTTCAATGC TTTTCAAGAT ACCCAGATCA TATGAAACGG | 240 |
| CATGACTTTT TCAAGAGTGC CATGCCCGAA GGTTATGTAC | 280 |
| AGGAAAGAAC TATATTTTTC AAAGATGACG GGAACTACAA | 320 |
| GACACGTGCT GAAGTCAAGT TTGAAGGTGA TACCCTTGTT | 360 |
| AATAGAATCG AGTTAAAAGG TATTGATTTT AAAGATGATG | 400 |
| GAAACATTCT TGGACACAAA TTGGAATACA ACTATAACGA | 440 |
| GCACTTGGTG TACATCATGG CAGACAAACA AAAGAATGGT | 480 |
| ACCAAAGCTA TCTTTCAAGT TCACCACAAC ATTGAAGATG | 520 |
| GAGGCGTTCA ACTAGCAGAC CATTATCAAC AAAATACTCC | 560 |
| AATTGGCGAT GGCCCTGTCC TTTTACCAGA CAACCATTAC | 600 |
| CTGCACACAC AATCTGCCCT TTCGAAAGAT CCCAACGAAA | 640 |
| AGAGAGACCA CATGGTCTTT CTTGAGTTTG TAACAGCTGC | 680 |
| TGGGATTACA CATGGCATGG ATGAAGTNTA CAAATAA | 717 |

(2) INFORMATION FOR SEQ ID NO: 20:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 20:

Met Ile Lys Gly Glu Glu Leu Phe Thr Gly Val Val
 1          5                10

Pro Ile Leu Val Glu Leu Asp Gly Asp Val Asn Gly
        15              20

His Lys Phe Ser Val Ser Gly Glu Gly Glu Gly Asp
 25             30              35

Ala Thr Tyr Gly Lys Leu Thr Leu Lys Phe Ile Cys
          40              45

Thr Thr Gly Lys Leu Pro Val Pro Trp Pro Thr Leu
 50             55              60

```
Val Thr Thr Phe Ser Tyr Gly Val Gln Cys Phe Ser
                 65                  70

Arg Tyr Pro Asp His Met Lys Arg His Asp Phe Phe
         75                  80

Lys Ser Ala Met Pro Glu Gly Tyr Val Gln Glu Arg
 85              90                  95

Thr Ile Phe Phe Lys Asp Asp Gly Asn Tyr Lys Thr
             100                 105

Arg Ala Glu Val Lys Phe Glu Gly Asp Thr Leu Val
     110             115                     120

Asn Arg Ile Glu Leu Lys Gly Ile Asp Phe Lys Asp
                 125             130

Asp Gly Asn Ile Leu Gly His Lys Leu Glu Tyr Asn
             135             140

Tyr Asn Glu His Leu Val Tyr Ile Met Ala Asp Lys
145                 150                 155

Gln Lys Asn Gly Thr Lys Ala Ile Phe Gln Val His
                 160             165

His Asn Ile Glu Asp Gly Gly Val Gln Leu Ala Asp
         170             175                 180

His Tyr Gln Gln Asn Thr Pro Ile Gly Asp Gly Pro
                 185             190

Val Leu Leu Pro Asp Asn His Tyr Leu His Thr Gln
             195             200

Ser Ala Leu Ser Lys Asp Pro Asn Glu Lys Arg Asp
205             210                 215

His Met Val Phe Leu Glu Phe Val Thr Ala Ala Gly
                 220             225

Ile Thr His Gly Met Asp Glu Val Tyr Lys
         230             235

(2) INFORMATION FOR SEQ ID NO: 21:

(i) SEQUENCE CHARACTERISTICS:
        (A) LENGTH: 717
        (B) TYPE: NUCLEIC ACID
        (C) STRANDEDNESS: UNKNOWN
        (D) TOPOLOGY: UNKNOWN (xi) SEQUENCE DESCRIPTION: SEQ ID NO: 21:

ATGAGTAAAG GAGAAGAACT TTTCACTGGA GTTGTCCCAA                40

TTCTTGTTGA ATTAGATGGT GATGTTAATG GGCACAAATT                80

TTCTGTCAGT GGAGAGGGTG AAGGTGATGC AACATACGGA               120

AAACTTACCC TTAAATTTAT TTGCACTACT GGAAAACTAC               160

CTGTTCCATG GCCAACACTT GTCACTACTT TCTCTTATGG               200

TGTTCAATGC TTTTCAAGAT ACCCAGATCA TATGAAACGG               240

CATGACTTTT TCAAGAGTGC CATGCCCGAA GGTTATGTAC               280

AGGAAAGAAC TATATTTTTC AAAGATGACG GAACTACAA                320

GACACGTGCT GAAGTCAAGT TTGAAGGTGA TACCCTTGTT               360

AATAGAATCG AGTTAAAAGG TATTGATTTT AAAGAAGATG               400

GAAACATTCT TGGACACAAA TTGGAATACA ACTATAACGA               440
```

-continued

```
TCACCAGGTG TACATCATGG CAGACAAACA AAAGAATGGA                        480

ATCAAAGCTA ACTTCAAAAT TAGACACAAC ATTGAAGATG                        520

GAGGCGTTCA ACTAGCAGAC CATTATCAAC AAAATACTCC                        560

AATTGGCGAT GGGCCCGTCC TTTTACCAGA CAACCATTAC                        600

CTGTTTACAA CTTCTACTCT TTCGAAAGAT CCCAACGAAA                        640

AGAGAGACCA CATGGTCCTT CTTGAGTTTG TAACAGCTGC                        680

TGGGATTACA CATGGCATGG ATGAACTATA CAAATAA                           717
```

(2) INFORMATION FOR SEQ ID NO: 22:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 22:

```
Met Ser Lys Gly Glu Glu Leu Phe Thr Gly Val Val
 1               5                  10

Pro Ile Leu Val Glu Leu Asp Gly Asp Val Asn Gly
            15                  20

His Lys Phe Ser Val Ser Gly Glu Gly Glu Gly Asp
 25              30                  35

Ala Thr Tyr Gly Lys Leu Thr Leu Lys Phe Ile Cys
             40                  45

Thr Thr Gly Lys Leu Pro Val Pro Trp Pro Thr Leu
     50                  55                  60

Val Thr Thr Phe Ser Tyr Gly Val Gln Cys Phe Ser
                 65                  70

Arg Tyr Pro Asp His Met Lys Arg His Asp Phe Phe
             75                  80

Lys Ser Ala Met Pro Glu Gly Tyr Val Gln Glu Arg
 85              90                  95

Thr Ile Phe Phe Lys Asp Asp Gly Asn Tyr Lys Thr
             100                 105

Arg Ala Glu Val Lys Phe Glu Gly Asp Thr Leu Val
     110                 115                 120

Asn Arg Ile Glu Leu Lys Gly Ile Asp Phe Lys Glu
                 125                 130

Asp Gly Asn Ile Leu Gly His Lys Leu Glu Tyr Asn
             135                 140

Tyr Asn Asp His Gln Val Tyr Ile Met Ala Asp Lys
145                 150                 155

Gln Lys Asn Gly Ile Lys Ala Asn Phe Lys Ile Arg
             160                 165

His Asn Ile Glu Asp Gly Gly Val Gln Leu Ala Asp
         170                 175                 180

His Tyr Gln Gln Asn Thr Pro Ile Gly Asp Gly Pro
                 185                 190

Val Leu Leu Pro Asp Asn His Tyr Leu Phe Thr Thr
             195                 200

Ser Thr Leu Ser Lys Asp Pro Asn Glu Lys Arg Asp
205                 210                 215
```

```
His Met Val Leu Leu Glu Phe Val Thr Ala Ala Gly
            220                 225

Ile Thr His Gly Met Asp Glu Leu Tyr Lys
        230             235

(2) INFORMATION FOR SEQ ID NO: 23:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 23:

Met Ser Lys Gly Glu Leu Phe Thr Gly Val Val
 1               5                  10

Pro Ile Leu Val Glu Leu Asp Gly Asp Val Asn Gly
            15                  20

His Lys Phe Ser Val Ser Gly Glu Gly Glu Gly Asp
 25                  30                  35

Ala Thr Tyr Gly Lys Leu Thr Leu Lys Phe Ile Cys
            40                  45

Thr Thr Gly Lys Leu Pro Val Pro Trp Pro Thr Leu
     50                  55                  60

Val Thr Thr Phe Ser Tyr Gly Val Gln Cys Phe Ser
                65                  70

Arg Tyr Pro Asp His Met Lys Arg His Asp Phe Phe
         75                  80

Lys Ser Ala Met Pro Glu Gly Tyr Val Gln Glu Arg
 85                  90                  95

Thr Ile Phe Phe Lys Asp Asp Gly Asn Tyr Lys Thr
             100                 105

Arg Ala Glu Val Lys Phe Glu Gly Asp Thr Leu Val
     110                 115                 120

Asn Arg Ile Glu Leu Lys Gly Ile Asp Phe Lys Glu
                 125                 130

Asp Gly Asn Ile Leu Gly His Lys Leu Glu Tyr Asn
         135                 140

Tyr Asn Asp His Gln Val Tyr Ile Met Ala Asp Lys
145                 150                 155

Gln Lys Asn Gly Ile Lys Ala Asn Phe Lys Ile Arg
             160                 165

His Asn Ile Glu Asp Gly Gly Val Gln Leu Ala Asp
         170                 175                 180

His Tyr Gln Gln Asn Thr Pro Ile Gly Asp Gly Pro
                 185                 190

Val Leu Leu Pro Asp Asn His Tyr Leu His Thr Gln
             195                 200

Ser Ala Leu Ser Lys Asp Pro Asn Glu Lys Arg Asp
205                 210                 215

His Met Val Leu Leu Glu Phe Val Thr Ala Ala Gly
            220                 225

Ile Thr His Gly Met Asp Glu Leu Tyr Lys
        230             235

(2) INFORMATION FOR SEQ ID NO: 24:
```

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 24:

Met Ser Lys Gly Glu Glu Leu Phe Thr Gly Val Val
  1               5                  10

Pro Ile Leu Val Glu Leu Asp Gly Asp Val Asn Gly
             15                  20

His Lys Phe Ser Val Ser Gly Glu Gly Glu Gly Asp
 25                  30                  35

Ala Thr Tyr Gly Lys Leu Thr Leu Lys Phe Ile Cys
             40                  45

Thr Thr Gly Lys Leu Pro Val Pro Trp Pro Thr Leu
         50              55                  60

Val Thr Thr Phe Ser Tyr Gly Val Gln Cys Phe Ser
                 65                  70

Arg Tyr Pro Asp His Met Lys Arg His Asp Phe Phe
             75                  80

Lys Ser Ala Met Pro Glu Gly Tyr Val Gln Glu Arg
 85                  90                  95

Thr Ile Phe Phe Lys Asp Asp Gly Asn Tyr Lys Thr
             100                 105

Arg Ala Glu Val Lys Phe Glu Gly Asp Thr Leu Val
     110                 115                 120

Asn Arg Ile Glu Leu Lys Gly Ile Asp Phe Lys Glu
                 125                 130

Asp Gly Asn Ile Leu Gly His Lys Leu Glu Tyr Asn
             135                 140

Tyr Asn Asp His Asp Val Tyr Ile Met Ala Asp Lys
145                 150                 155

Gln Lys Asn Gly Thr Lys Ala Asn Phe Gln Val Arg
                 160                 165

His Asn Ile Glu Asp Gly Gly Val Gln Leu Ala Asp
     170                 175                 180

His Tyr Gln Gln Asn Thr Pro Ile Gly Asp Gly Pro
                 185                 190

Val Leu Leu Pro Asp Asn His Tyr Leu His Thr Gln
             195                 200

Ser Ala Leu Ser Lys Asp Pro Asn Glu Lys Arg Asp
205                 210                 215

His Met Val Leu Leu Glu Phe Val Thr Ala Ala Gly
             220                 225

Ile Thr His Gly Met Asp Glu Leu Tyr Lys
             230                 235

(2) INFORMATION FOR SEQ ID NO: 25:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 25:

Met Ser Lys Gly Glu Glu Leu Phe Thr Gly Val Val
 1               5                  10

Pro Ile Leu Val Glu Leu Asp Gly Asp Val Asn Gly
         15                 20

His Lys Phe Ser Val Ser Gly Glu Gly Glu Gly Asp
 25              30                  35

Ala Thr Tyr Gly Lys Leu Thr Leu Lys Phe Ile Cys
             40              45

Thr Thr Gly Lys Leu Pro Val Pro Trp Pro Thr Leu
     50              55                  60

Val Thr Thr Phe Ser Tyr Gly Val Gln Cys Phe Ser
                 65              70

Arg Tyr Pro Asp His Met Lys Arg His Asp Phe Phe
         75              80

Lys Ser Ala Met Pro Glu Gly Tyr Val Gln Glu Arg
 85              90                  95

Thr Ile Phe Phe Lys Asp Asp Gly Asn Tyr Lys Thr
             100             105

Arg Ala Glu Val Lys Phe Glu Gly Asp Thr Leu Val
     110             115                 120

Asn Arg Ile Glu Leu Lys Gly Ile Asp Phe Lys Glu
                 125             130

Asp Gly Asn Ile Leu Gly His Lys Leu Glu Tyr Asn
         135             140

Tyr Asn Asp His Asn Val Tyr Ile Met Ala Asp Lys
145             150                 155

Gln Lys Asn Gly Ile Lys Val Asn Phe Lys Ile Arg
             160             165

His Asn Ile Glu Asp Gly Ser Val Gln Leu Ala Asp
     170             175                 180

His Tyr Gln Gln Asn Thr Pro Ile Gly Asp Gly Pro
                 185             190

Val Leu Leu Pro Asp Asn His Tyr Leu His Thr Gln
         195             200

Ser Ala Leu Ser Lys Asp Pro Asn Glu Lys Arg Asp
205             210                 215

His Met Val Leu Leu Glu Phe Val Thr Ala Ala Gly
             220             225

Ile Thr His Gly Met Asp Glu Leu Tyr Lys
     230             235

(2) INFORMATION FOR SEQ ID NO: 26:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 26:

Met Ser Lys Gly Glu Glu Leu Phe Thr Gly Val Val
 1               5                  10

Pro Ile Leu Val Glu Leu Asp Gly Asp Val Asn Gly
         15                 20

His Lys Phe Ser Val Ser Gly Glu Gly Glu Gly Asp

```
                  25                  30                  35
Ala Thr Tyr Gly Lys Leu Thr Leu Lys Phe Ile Cys
                40                  45

Thr Thr Gly Lys Leu Pro Val Pro Trp Pro Thr Leu
    50                  55                  60

Val Thr Thr Phe Ser Tyr Gly Val Gln Cys Phe Ser
                65                  70

Arg Tyr Pro Asp His Met Lys Arg His Asp Phe Phe
        75                  80

Lys Ser Ala Met Pro Glu Gly Tyr Val Gln Glu Arg
85                  90                  95

Thr Ile Phe Phe Lys Asp Asp Gly Asn Tyr Lys Thr
                100                 105

Arg Ala Glu Val Lys Phe Glu Gly Asp Thr Leu Val
        110                 115                 120

Asn Arg Ile Glu Leu Lys Gly Ile Asp Phe Lys Glu
                125                 130

Asp Gly Asn Ile Leu Gly His Lys Leu Glu Tyr Asn
        135                 140

Tyr Asn Asp His His Val Tyr Ile Met Ala Asp Lys
145                 150                 155

Gln Lys Asn Gly Ile Lys Val Asn Phe Lys Ile Arg
                160                 165

His Asn Ile Glu Asp Gly Ser Val Gln Leu Ala Asp
        170                 175                 180

His Tyr Gln Gln Asn Thr Pro Ile Gly Asp Gly Pro
                185                 190

Val Leu Leu Pro Asp Asn His Tyr Leu His Thr Gln
        195                 200

Ser Ala Leu Ser Lys Asp Pro Asn Glu Lys Arg Asp
205                 210                 215

His Met Val Leu Leu Glu Phe Val Thr Ala Ala Gly
                220                 225

Ile Thr His Gly Met Asp Glu Leu Tyr Lys
        230                 235

(2) INFORMATION FOR SEQ ID NO: 27:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 27:

Met Ser Lys Gly Glu Glu Leu Phe Thr Gly Val Val
1                   5                   10

Pro Ile Leu Val Glu Leu Asp Gly Asp Val Asn Gly
                15                  20

His Lys Phe Ser Val Ser Gly Glu Gly Glu Gly Asp
        25                  30                  35

Ala Thr Tyr Gly Lys Leu Thr Leu Lys Phe Ile Cys
                40                  45

Thr Thr Gly Lys Leu Pro Val Pro Trp Pro Thr Leu
    50                  55                  60
```

Val Thr Thr Phe Ser Tyr Gly Val Gln Cys Phe Ser
                65                  70

Arg Tyr Pro Asp His Met Lys Arg His Asp Phe Phe
        75                  80

Lys Ser Ala Met Pro Glu Gly Tyr Val Gln Glu Arg
85                  90                  95

Thr Ile Phe Phe Lys Asp Asp Gly Asn Tyr Lys Thr
                100                 105

Arg Ala Glu Val Lys Phe Glu Gly Asp Thr Leu Val
        110                 115                 120

Asn Arg Ile Glu Leu Lys Gly Ile Asp Phe Lys Glu
                125                 130

Asp Gly Asn Ile Leu Gly His Lys Leu Glu Tyr Asn
        135                 140

Tyr Asn Asp His Val Val Tyr Ile Met Ala Asp Lys
145                 150                 155

Gln Lys Asn Gly Ile Lys Val Asn Phe Lys Ile Arg
        160                 165

His Asn Ile Glu Asp Gly Ser Val Gln Leu Ala Asp
        170                 175                 180

His Tyr Gln Gln Asn Thr Pro Ile Gly Asp Gly Pro
                185                 190

Val Leu Leu Pro Asp Asn His Tyr Leu His Thr Gln
        195                 200

Ser Ala Leu Ser Lys Asp Pro Asn Glu Lys Arg Asp
205                 210                 215

His Met Val Leu Leu Glu Phe Val Thr Ala Ala Gly
        220                 225

Ile Thr His Gly Met Asp Glu Leu Tyr Lys
        230                 235

(2) INFORMATION FOR SEQ ID NO: 28:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 28:

Met Ser Lys Gly Glu Glu Leu Phe Thr Gly Val Val
1               5                   10

Pro Ile Leu Val Glu Leu Asp Gly Asp Val Asn Gly
        15                  20

His Lys Phe Ser Val Ser Gly Glu Gly Glu Gly Asp
25                  30                  35

Ala Thr Tyr Gly Lys Leu Thr Leu Lys Phe Ile Cys
        40                  45

Thr Thr Gly Lys Leu Pro Val Pro Trp Pro Thr Leu
        50                  55                  60

Val Thr Thr Phe Ser Tyr Gly Val Gln Cys Phe Ser
                65                  70

Arg Tyr Pro Asp His Met Lys Arg His Asp Phe Phe
        75                  80

Lys Ser Ala Met Pro Glu Gly Tyr Val Gln Glu Arg
85                  90                  95

-continued

```
Thr Ile Phe Phe Lys Asp Asp Gly Asn Tyr Lys Thr
            100                 105
Arg Ala Glu Val Lys Phe Glu Gly Asp Thr Leu Val
            110                 115                 120
Asn Arg Ile Glu Leu Lys Gly Ile Asp Phe Lys Glu
                        125                 130
Asp Gly Asn Ile Leu Gly His Lys Leu Glu Tyr Asn
            135                 140
Tyr Asn Asp His Gln Val Tyr Ile Met Ala Asp Lys
145                 150                 155
Gln Lys Asn Gly Ile Lys Val Asn Phe Lys Ile Arg
            160                 165
His Asn Ile Glu Asp Gly Gly Val Gln Leu Ala Asp
            170                 175                 180
His Tyr Gln Gln Asn Thr Pro Ile Gly Asp Gly Pro
                        185                 190
Val Leu Leu Pro Asp Asn His Tyr Leu His Thr Gln
            195                 200
Ser Ala Leu Ser Lys Asp Pro Asn Glu Lys Arg Asp
205                 210                 215
His Met Val Leu Leu Glu Phe Val Thr Ala Ala Gly
            220                 225
Ile Thr His Gly Met Asp Glu Leu Tyr Lys
            230                 235

(2) INFORMATION FOR SEQ ID NO: 29:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 29:

Met Ser Lys Gly Glu Glu Leu Phe Thr Gly Val Val
 1               5                  10
Pro Ile Leu Val Glu Leu Asp Gly Asp Val Asn Gly
            15                  20
His Lys Phe Ser Val Ser Gly Glu Gly Glu Gly Asp
 25                  30                  35
Ala Thr Tyr Gly Lys Leu Thr Leu Lys Phe Ile Cys
            40                  45
Thr Thr Gly Lys Leu Pro Val Pro Trp Pro Thr Leu
 50                  55                  60
Val Thr Thr Phe Ser Tyr Gly Val Gln Cys Phe Ser
            65                  70
Arg Tyr Pro Asp His Met Lys Arg His Asp Phe Phe
            75                  80
Lys Ser Ala Met Pro Glu Gly Tyr Val Gln Glu Arg
 85                  90                  95
Thr Ile Phe Phe Lys Asp Asp Gly Asn Tyr Lys Thr
            100                 105
Arg Ala Glu Val Lys Phe Glu Gly Asp Thr Leu Val
            110                 115                 120
Asn Arg Ile Glu Leu Lys Gly Ile Asp Phe Lys Glu
```

```
            125                 130
Asp Gly Asn Ile Leu Gly His Lys Leu Glu Tyr Asn
            135                 140

Tyr Asn Asp His Thr Val Tyr Ile Met Ala Asp Lys
145                 150                 155

Gln Lys Asn Gly Ile Lys Val Asn Phe Lys Ile Arg
            160                 165

His Asn Ile Glu Asp Gly Ser Val Gln Leu Ala Asp
            170                 175                 180

His Tyr Gln Gln Asn Thr Pro Ile Gly Asp Gly Pro
                    185                 190

Val Leu Leu Pro Asp Asn His Tyr Leu His Thr Gln
            195                 200

Ser Ala Leu Ser Lys Asp Pro Asn Glu Lys Arg Asp
205                 210                 215

His Met Val Leu Leu Glu Phe Val Thr Ala Ala Gly
            220                 225

Ile Thr His Gly Met Asp Glu Leu Tyr Lys
            230                 235

(2) INFORMATION FOR SEQ ID NO: 30:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 30:

Met Ser Lys Gly Glu Glu Leu Phe Thr Gly Val Val
1                   5                   10

Pro Ile Leu Val Glu Leu Asp Gly Asp Val Asn Gly
            15                  20

His Lys Phe Ser Val Ser Gly Glu Gly Glu Gly Asp
25                  30                  35

Ala Thr Tyr Gly Lys Leu Thr Leu Lys Phe Ile Cys
            40                  45

Thr Thr Gly Lys Leu Pro Val Pro Trp Pro Thr Leu
    50                  55                  60

Val Thr Thr Phe Ser Tyr Gly Val Gln Cys Phe Ser
                65                  70

Arg Tyr Pro Asp His Met Lys Arg His Asp Phe Phe
        75                  80

Lys Ser Ala Met Pro Glu Gly Tyr Val Gln Glu Arg
85                  90                  95

Thr Ile Phe Phe Lys Asp Asp Gly Asn Tyr Lys Thr
            100                 105

Arg Ala Glu Val Lys Phe Glu Gly Asp Thr Leu Val
            110                 115                 120

Asn Arg Ile Glu Leu Lys Gly Ile Asp Phe Lys Glu
                125                 130

Asp Gly Asn Ile Leu Gly His Lys Leu Glu Tyr Asn
            135                 140

Tyr Asn Asp His Leu Val Tyr Ile Met Ala Asp Lys
145                 150                 155
```

Gln Lys Asn Gly Thr Lys Val Asn Phe Gln Val His
            160                 165

His Asn Ile Glu Asp Gly Ser Val Gln Leu Ala Asp
        170                 175                 180

His Tyr Gln Gln Asn Thr Pro Ile Gly Asp Gly Pro
                185                 190

Val Leu Leu Pro Asp Asn His Tyr Leu His Thr Gln
            195                 200

Ser Ala Leu Ser Lys Asp Pro Asn Glu Lys Arg Asp
205                 210                 215

His Met Val Leu Leu Glu Phe Val Thr Ala Ala Gly
            220                 225

Ile Thr His Gly Met Asp Glu Leu Tyr Lys
            230                 235

(2) INFORMATION FOR SEQ ID NO: 31:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 31:

Met Ser Lys Gly Glu Glu Leu Phe Thr Gly Val Val
1               5                   10

Pro Ile Leu Val Glu Leu Asp Gly Asp Val Asn Gly
            15                  20

His Lys Phe Ser Val Ser Gly Glu Gly Glu Gly Asp
25                  30                  35

Ala Thr Tyr Gly Lys Leu Thr Leu Lys Phe Ile Cys
            40                  45

Thr Thr Gly Lys Leu Pro Val Pro Trp Pro Thr Leu
    50                  55                  60

Val Thr Thr Phe Ser Tyr Gly Val Gln Cys Phe Ser
                65                  70

Arg Tyr Pro Asp His Met Lys Arg His Asp Phe Phe
            75                  80

Lys Ser Ala Met Pro Glu Gly Tyr Val Gln Glu Arg
85                  90                  95

Thr Ile Phe Phe Lys Asp Asp Gly Asn Tyr Lys Thr
            100                 105

Arg Ala Glu Val Lys Phe Glu Gly Asp Thr Leu Val
    110                 115                 120

Asn Arg Ile Glu Leu Lys Gly Ile Asp Phe Lys Glu
            125                 130

Asp Gly Asn Ile Leu Gly His Lys Leu Glu Tyr Asn
            135                 140

Tyr Asn Asp His Asp Val Tyr Ile Met Ala Asp Lys
145                 150                 155

Gln Lys Asn Gly Thr Lys Val Asn Phe Gln Val Arg
            160                 165

His Asn Ile Glu Asp Gly Ser Val Gln Leu Ala Asp
        170                 175                 180

His Tyr Gln Gln Asn Thr Pro Ile Gly Asp Gly Pro
                185                 190

Val Leu Leu Pro Asp Asn His Tyr Leu His Thr Gln
        195                 200

Ser Ala Leu Ser Lys Asp Pro Asn Glu Lys Arg Asp
205                 210                 215

His Met Val Leu Leu Glu Phe Val Thr Ala Ala Gly
        220                 225

Ile Thr His Gly Met Asp Glu Leu Tyr Lys
        230                 235

(2) INFORMATION FOR SEQ ID NO: 32:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 32:

Met Ser Lys Gly Glu Glu Leu Phe Thr Gly Val Val
1               5                   10

Pro Ile Leu Val Glu Leu Asp Gly Asp Val Asn Gly
        15                  20

His Lys Phe Ser Val Ser Gly Glu Gly Glu Gly Asp
    25                  30                  35

Ala Thr Tyr Gly Lys Leu Thr Leu Lys Phe Ile Cys
        40                  45

Thr Thr Gly Lys Leu Pro Val Pro Trp Pro Thr Leu
    50                  55                  60

Val Thr Thr Phe Ser Tyr Gly Val Gln Cys Phe Ser
        65                  70

Arg Tyr Pro Asp His Met Lys Arg His Asp Phe Phe
        75                  80

Lys Ser Ala Met Pro Glu Gly Tyr Val Gln Glu Arg
85                  90                  95

Thr Ile Phe Phe Lys Asp Asp Gly Asn Tyr Lys Thr
        100                 105

Arg Ala Glu Val Lys Phe Glu Gly Asp Thr Leu Val
    110                 115                 120

Asn Arg Ile Glu Leu Lys Gly Ile Asp Phe Lys Glu
                125                 130

Asp Gly Asn Ile Leu Gly His Lys Leu Glu Tyr Asn
        135                 140

Tyr Asn Asp His Leu Val Tyr Ile Met Ala Asp Lys
145                 150                 155

Gln Lys Asn Gly Thr Lys Val Asn Phe Gln Val Arg
        160                 165

His Asn Ile Glu Asp Gly Ser Val Gln Leu Ala Asp
        170                 175                 180

His Tyr Gln Gln Asn Thr Pro Ile Gly Asp Gly Pro
                185                 190

Val Leu Leu Pro Asp Asn His Tyr Leu His Thr Gln
        195                 200

Ser Ala Leu Ser Lys Asp Pro Asn Glu Lys Arg Asp
205                 210                 215

His Met Val Leu Leu Glu Phe Val Thr Ala Ala Gly

```
            220                 225

Ile Thr His Gly Met Asp Glu Leu Tyr Lys
    230                 235

(2) INFORMATION FOR SEQ ID NO: 33:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 33:

Met Ser Lys Gly Glu Glu Leu Phe Thr Gly Val Val
1               5                   10

Pro Ile Leu Val Glu Leu Asp Gly Asp Val Asn Gly
            15                  20

His Lys Phe Ser Val Ser Gly Glu Gly Glu Gly Asp
    25                  30                  35

Ala Thr Tyr Gly Lys Leu Thr Leu Lys Phe Ile Cys
                40                  45

Thr Thr Gly Lys Leu Pro Val Pro Trp Pro Thr Leu
        50                  55                  60

Val Thr Thr Phe Ser Tyr Gly Val Gln Cys Phe Ser
                    65                  70

Arg Tyr Pro Asp His Met Lys Arg His Asp Phe Phe
            75                  80

Lys Ser Ala Met Pro Glu Gly Tyr Val Gln Glu Arg
85                  90                  95

Thr Ile Phe Phe Lys Asp Asp Gly Asn Tyr Lys Thr
                100                 105

Arg Ala Glu Val Lys Phe Glu Gly Asp Thr Leu Val
            110                 115                 120

Asn Arg Ile Glu Leu Lys Gly Ile Asp Phe Lys Glu
                    125                 130

Asp Gly Asn Ile Leu Gly His Lys Leu Glu Tyr Asn
            135                 140

Tyr Asn Pro His Tyr Val Tyr Ile Met Ala Asp Lys
145                 150                 155

Gln Lys Asn Gly Thr Lys Val Asn Phe Gln Val His
                160                 165

His Asn Ile Glu Asp Gly Ser Val Gln Leu Ala Asp
            170                 175                 180

His Tyr Gln Gln Asn Thr Pro Ile Gly Asp Gly Pro
                    185                 190

Val Leu Leu Pro Asp Asn His Tyr Leu His Thr Gln
            195                 200

Ser Ala Leu Ser Lys Asp Pro Asn Glu Lys Arg Asp
205                 210                 215

His Met Val Leu Leu Glu Phe Val Thr Ala Ala Gly
            220                 225

Ile Thr His Gly Met Asp Glu Leu Tyr Lys
    230                 235

(2) INFORMATION FOR SEQ ID NO: 34:
```

(i) SEQUENCE CHARACTERISTICS:
    (A) LENGTH: 238
    (B) TYPE: AMINO ACID
    (C) STRANDEDNESS: UNKNOWN
    (D) TOPOLOGY: UNKNOWN (xi) SEQUENCE DESCRIPTION: SEQ ID NO: 34:

```
Met Ser Lys Gly Glu Glu Leu Phe Thr Gly Val Val
 1               5                  10

Pro Ile Leu Val Glu Leu Asp Gly Asp Val Asn Gly
            15                  20

His Lys Phe Ser Val Ser Gly Glu Gly Glu Gly Asp
 25                  30                  35

Ala Thr Tyr Gly Lys Leu Thr Leu Lys Phe Ile Cys
            40                  45

Thr Thr Gly Lys Leu Pro Val Pro Trp Pro Thr Leu
 50                  55                  60

Val Thr Thr Phe Ser Tyr Gly Val Gln Cys Phe Ser
            65                  70

Arg Tyr Pro Asp His Met Lys Arg His Asp Phe Phe
            75                  80

Lys Ser Ala Met Pro Glu Gly Tyr Val Gln Glu Arg
 85                  90                  95

Thr Ile Phe Phe Lys Asp Asp Gly Asn Tyr Lys Thr
            100                 105

Arg Ala Glu Val Lys Phe Glu Gly Asp Thr Leu Val
            110                 115                 120

Asn Arg Ile Glu Leu Lys Gly Ile Asp Phe Lys Glu
                     125                 130

Asp Gly Asn Ile Leu Gly His Lys Leu Glu Tyr Asn
            135                 140

Tyr Asn Glu His Leu Val Tyr Ile Met Ala Asp Lys
 145                 150                 155

Gln Lys Asn Gly Thr Lys Ala Asn Phe Lys Ile His
            160                 165

His Asn Ile Glu Asp Gly Gly Val Gln Leu Ala Asp
            170                 175                 180

His Tyr Gln Gln Asn Thr Pro Ile Gly Asp Gly Pro
                     185                 190

Val Leu Leu Pro Asp Asn His Tyr Leu His Thr Gln
            195                 200

Ser Ala Leu Ser Lys Asp Pro Asn Glu Lys Arg Asp
 205                 210                 215

His Met Val Leu Leu Glu Phe Val Thr Ala Ala Gly
            220                 225

Ile Thr His Gly Met Asp Glu Leu Tyr Lys
            230                 235
```

(2) INFORMATION FOR SEQ ID NO: 35:

(i) SEQUENCE CHARACTERISTICS:
    (A) LENGTH: 238
    (B) TYPE: AMINO ACID
    (C) STRANDEDNESS: UNKNOWN
    (D) TOPOLOGY: UNKNOWN (xi) SEQUENCE DESCRIPTION: SEQ ID NO: 35:

```
Met Ser Lys Gly Glu Glu Leu Phe Thr Gly Val Val
  1               5                  10

Pro Ile Leu Val Glu Leu Asp Gly Asp Val Asn Gly
             15                  20

His Lys Phe Ser Val Ser Gly Glu Gly Glu Gly Asp
 25                  30                  35

Ala Thr Tyr Gly Lys Leu Thr Leu Lys Phe Ile Cys
             40                  45

Thr Thr Gly Lys Leu Pro Val Pro Trp Pro Thr Leu
 50                  55                  60

Val Thr Thr Phe Ser Tyr Gly Val Gln Cys Phe Ser
             65                  70

Arg Tyr Pro Asp His Met Lys Arg His Asp Phe Phe
             75                  80

Lys Ser Ala Met Pro Glu Gly Tyr Val Gln Glu Arg
 85                  90                  95

Thr Ile Phe Phe Lys Asp Asp Gly Asn Tyr Lys Thr
            100                 105

Arg Ala Glu Val Lys Phe Glu Gly Asp Thr Leu Val
110                 115                 120

Asn Arg Ile Glu Leu Lys Gly Ile Asp Phe Lys Glu
            125                 130

Asp Gly Asn Ile Leu Gly His Lys Leu Glu Tyr Asn
            135                 140

Tyr Asn Ser His Asn Val Tyr Ile Met Ala Asp Lys
145                 150                 155

Gln Lys Asn Gly Ile Lys Val Asn Phe Lys Ile Arg
            160                 165

His Asn Ile Glu Asp Gly Ser Val Gln Leu Ala Asp
            170                 175                 180

His Tyr Gln Gln Asn Thr Pro Ile Gly Asp Gly Pro
                    185                 190

Val Leu Leu Pro Asp Asn His Tyr Leu His Thr Gln
            195                 200

Ser Ala Leu Ser Lys Asp Pro Asn Glu Lys Arg Asp
205                 210                 215

His Met Val Leu Leu Glu Phe Val Thr Ala Ala Gly
            220                 225

Ile Thr His Gly Met Asp Glu Leu Tyr Lys
            230                 235

(2) INFORMATION FOR SEQ ID NO: 36:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 36:

Met Ser Lys Gly Glu Glu Leu Phe Thr Gly Val Val
  1               5                  10

Pro Ile Leu Val Glu Leu Asp Gly Asp Val Asn Gly
             15                  20

His Lys Phe Ser Val Ser Gly Glu Gly Glu Gly Asp
 25                  30                  35
```

```
Ala Thr Tyr Gly Lys Leu Thr Leu Lys Phe Ile Cys
             40                  45

Thr Thr Gly Lys Leu Pro Val Pro Trp Pro Thr Leu
         50                  55                  60

Val Thr Thr Phe Ser Tyr Gly Val Gln Cys Phe Ser
                 65                  70

Arg Tyr Pro Asp His Met Lys Arg His Asp Phe Phe
             75                  80

Lys Ser Ala Met Pro Glu Gly Tyr Val Gln Glu Arg
 85                  90                  95

Thr Ile Phe Phe Lys Asp Asp Gly Asn Tyr Lys Thr
                100                 105

Arg Ala Glu Val Lys Phe Glu Gly Asp Thr Leu Val
        110                 115                 120

Asn Arg Ile Glu Leu Lys Gly Ile Asp Phe Lys Glu
                125                 130

Asp Gly Asn Ile Leu Gly His Lys Leu Glu Tyr Asn
                135                 140

Tyr Asn Pro His Trp Val Tyr Ile Met Ala Asp Lys
145                 150                 155

Gln Lys Asn Gly Ile Lys Val Asn Phe Lys Ile Arg
                160                 165

His Asn Ile Glu Asp Gly Ser Val Gln Leu Ala Asp
        170                 175                 180

His Tyr Gln Gln Asn Thr Pro Ile Gly Asp Gly Pro
                185                 190

Val Leu Leu Pro Asp Asn His Tyr Leu His Thr Gln
                195                 200

Ser Ala Leu Ser Lys Asp Pro Asn Glu Lys Arg Asp
205                 210                 215

His Met Val Leu Leu Glu Phe Val Thr Ala Ala Gly
        220                 225

Ile Thr His Gly Met Asp Glu Leu Tyr Lys
        230                 235

(2) INFORMATION FOR SEQ ID NO: 37:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 37:

Met Ser Lys Gly Glu Glu Leu Phe Thr Gly Val Val
 1                   5                  10

Pro Ile Leu Val Glu Leu Asp Gly Asp Val Asn Gly
             15                  20

His Lys Phe Ser Val Ser Gly Glu Gly Glu Gly Asp
 25                  30                  35

Ala Thr Tyr Gly Lys Leu Thr Leu Lys Phe Ile Cys
             40                  45

Thr Thr Gly Lys Leu Pro Val Pro Trp Pro Thr Leu
         50                  55                  60

Val Thr Thr Phe Ser Tyr Gly Val Gln Cys Phe Ser
```

```
                      65                  70
Arg Tyr Pro Asp His Met Lys Arg His Asp Phe Phe
            75                  80
Lys Ser Ala Met Pro Glu Gly Tyr Val Gln Glu Arg
 85                  90                  95
Thr Ile Phe Phe Lys Asp Asp Gly Asn Tyr Lys Thr
                100                 105
Arg Ala Glu Val Lys Phe Glu Gly Asp Thr Leu Val
110                 115                     120
Asn Arg Ile Glu Leu Lys Gly Ile Asp Phe Lys Glu
                125                 130
Asp Gly Asn Ile Leu Gly His Lys Leu Glu Tyr Asn
            135                 140
Tyr Asn Pro His Trp Val Tyr Ile Met Ala Asp Lys
145                 150                     155
Gln Lys Asn Gly Thr Lys Val Asn Phe Gln Val His
                160                 165
His Asn Ile Glu Asp Gly Ser Val Gln Leu Ala Asp
            170                 175                 180
His Tyr Gln Gln Asn Thr Pro Ile Gly Asp Gly Pro
                185                 190
Val Leu Leu Pro Asp Asn His Tyr Leu His Thr Gln
            195                 200
Ser Ala Leu Ser Lys Asp Pro Asn Glu Lys Arg Asp
205                 210                     215
His Met Val Leu Leu Glu Phe Val Thr Ala Ala Gly
                220                 225
Ile Thr His Gly Met Asp Glu Leu Tyr Lys
            230                 235

(2) INFORMATION FOR SEQ ID NO: 38:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (ix) FEATURE:
        (A) NAME/KEY: XAA
        (B) LOCATION: 93
        (D) OTHER INFORMATION: XAA = Any amino acid (ix) FEATURE:
        (A) NAME/KEY: XAA
        (B) LOCATION: 95
        (D) OTHER INFORMATION: XAA = Any amino acid (ix) FEATURE:
        (A) NAME/KEY: XAA
        (B) LOCATION: 97
        (D) OTHER INFORMATION: XAA = Any amino acid (ix) FEATURE:
        (A) NAME/KEY: XAA
        (B) LOCATION: 147
        (D) OTHER INFORMATION: XAA = Any amino acid (ix) FEATURE:
        (A) NAME/KEY: XAA
        (B) LOCATION: 149
        (D) OTHER INFORMATION: XAA = Any amino acid (ix) FEATURE:
```

```
            (A) NAME/KEY:  XAA
            (B) LOCATION:  166
            (D) OTHER INFORMATION:  XAA = Any amino acid (ix) FEATURE:
            (A) NAME/KEY:  XAA
            (B) LOCATION:  168
            (D) OTHER INFORMATION:  XAA = Any amino acid (ix) FEATURE:
            (A) NAME/KEY:  XAA
            (B) LOCATION:  202
            (D) OTHER INFORMATION:  XAA = Any amino acid (ix) FEATURE:
            (A) NAME/KEY:  XAA
            (B) LOCATION:  204
            (D) OTHER INFORMATION:  XAA = Any amino acid (ix) FEATURE:
            (A) NAME/KEY:  XAA
            (B) LOCATION:  206
            (D) OTHER INFORMATION:  XAA = Any amino acid (ix) FEATURE:
            (A) NAME/KEY:  XAA
            (B) LOCATION:  221
            (D) OTHER INFORMATION:  XAA = Any amino acid (ix) FEATURE:
            (A) NAME/KEY:  XAA
            (B) LOCATION:  223
            (D) OTHER INFORMATION:  XAA = Any amino acid (xi) SEQUENCE DESCRIPTION: SEQ ID NO: 38:

Met Ser Lys Gly Glu Glu Leu Phe Thr Gly Val Val
 1               5                  10

Pro Ile Leu Val Glu Leu Asp Gly Asp Val Asn Gly
            15                  20

His Lys Phe Ser Val Ser Gly Glu Gly Glu Gly Asp
 25                  30                  35

Ala Thr Tyr Gly Lys Leu Thr Leu Lys Phe Ile Cys
             40                  45

Thr Thr Gly Lys Leu Pro Val Pro Trp Pro Thr Leu
 50                  55                  60

Val Thr Thr Phe Ser Tyr Gly Val Gln Cys Phe Ser
             65                  70

Arg Tyr Pro Asp His Met Lys Arg His Asp Phe Phe
 75                  80

Lys Ser Ala Met Pro Glu Gly Tyr Xaa Gln Xaa Arg
 85                  90                  95

Xaa Ile Phe Phe Lys Asp Asp Gly Asn Tyr Lys Thr
                    100                 105

Arg Ala Glu Val Lys Phe Glu Gly Asp Thr Leu Val
 110                 115                 120

Asn Arg Ile Glu Leu Lys Gly Ile Asp Phe Lys Glu
                    125                 130

Asp Gly Asn Ile Leu Gly His Lys Leu Glu Tyr Asn
             135                 140

Tyr Asn Xaa His Xaa Val Tyr Ile Met Ala Asp Lys
 145                 150                 155

Gln Lys Asn Gly Ile Lys Val Asn Phe Xaa Ile Xaa
             160                 165

His Asn Ile Glu Asp Gly Ser Val Gln Leu Ala Asp
```

-continued

```
            170                 175                 180
His Tyr Gln Gln Asn Thr Pro Ile Gly Asp Gly Pro
                    185                 190

Val Leu Leu Pro Asp Asn His Tyr Leu Xaa Thr Xaa
            195                 200

Ser Xaa Leu Ser Lys Asp Pro Asn Glu Lys Arg Asp
205                 210                 215

His Met Val Leu Xaa Glu Xaa Val Thr Ala Ala Gly
                    220                 225

Ile Thr His Gly Met Asp Glu Leu Tyr Lys
            230                 235
```

(2) INFORMATION FOR SEQ ID NO: 39:

(i) SEQUENCE CHARACTERISTICS:
        (A) LENGTH: 238
        (B) TYPE: AMINO ACID
        (C) STRANDEDNESS: UNKNOWN
        (D) TOPOLOGY: UNKNOWN (ix) FEATURE:
        (A) NAME/KEY: XAA
        (B) LOCATION: 147
        (D) OTHER INFORMATION: XAA = Any amino acid (ix) FEATURE:
        (A) NAME/KEY: XAA
        (B) LOCATION: 149
        (D) OTHER INFORMATION: XAA = Any amino acid (ix) FEATURE:
        (A) NAME/KEY: XAA
        (B) LOCATION: 161
        (D) OTHER INFORMATION: XAA = Any amino acid (ix) FEATURE:
        (A) NAME/KEY: XAA
        (B) LOCATION: 163
        (D) OTHER INFORMATION: XAA = Any amino acid (ix) FEATURE:
        (A) NAME/KEY: XAA
        (B) LOCATION: 166
        (D) OTHER INFORMATION: XAA = Any amino acid (ix) FEATURE:
        (A) NAME/KEY: XAA
        (B) LOCATION: 167
        (D) OTHER INFORMATION: XAA = Any amino acid (ix) FEATURE:
        (A) NAME/KEY: XAA
        (B) LOCATION: 168
        (D) OTHER INFORMATION: XAA = Any amino acid (ix) FEATURE:
        (A) NAME/KEY: XAA
        (B) LOCATION: 175
        (D) OTHER INFORMATION: XAA = Any amino acid (ix) FEATURE:
        (A) NAME/KEY: XAA
        (B) LOCATION: 202
        (D) OTHER INFORMATION: XAA = Any amino acid (xi) SEQUENCE DESCRIPTION: SEQ ID NO: 39:

```
Met Ser Lys Gly Glu Glu Leu Phe Thr Gly Val Val
1                   5                   10

Pro Ile Leu Val Glu Leu Asp Gly Asp Val Asn Gly
            15                  20
```

-continued

```
His Lys Phe Ser Val Ser Gly Glu Gly Glu Gly Asp
 25              30                  35

Ala Thr Tyr Gly Lys Leu Thr Leu Lys Phe Ile Cys
             40              45

Thr Thr Gly Lys Leu Pro Val Pro Trp Pro Thr Leu
     50              55              60

Val Thr Thr Phe Ser Tyr Gly Val Gln Cys Phe Ser
                 65              70

Arg Tyr Pro Asp His Met Lys Arg His Asp Phe Phe
         75              80

Lys Ser Ala Met Pro Glu Gly Tyr Val Gln Glu Arg
 85              90                      95

Thr Ile Phe Phe Lys Asp Asp Gly Asn Tyr Lys Thr
            100             105

Arg Ala Glu Val Lys Phe Glu Gly Asp Thr Leu Val
        110             115             120

Asn Arg Ile Glu Leu Lys Gly Ile Asp Phe Lys Glu
                125             130

Asp Gly Asn Ile Leu Gly His Lys Leu Glu Tyr Asn
            135             140

Tyr Asn Xaa His Xaa Val Tyr Ile Met Ala Asp Lys
145             150                     155

Gln Lys Asn Gly Xaa Lys Xaa Asn Phe Xaa Xaa Xaa
            160             165

His Asn Ile Glu Asp Gly Xaa Val Gln Leu Ala Asp
        170             175             180

His Tyr Gln Gln Asn Thr Pro Ile Gly Asp Gly Pro
                185             190

Val Leu Leu Pro Asp Asn His Tyr Leu Xaa Thr Gln
        195             200

Ser Ala Leu Ser Lys Asp Pro Asn Glu Lys Arg Asp
205             210             215

His Met Val Leu Leu Glu Phe Val Thr Ala Ala Gly
            220             225

Ile Thr His Gly Met Asp Glu Leu Tyr Lys
230             235
```

HYBRID MOLECULES AND THEIR USE FOR OPTICALLY DETECTING CHANGES IN CELLULAR MICROENVIRONMENTS

This application claims priority from U.S. provisional application Nos. 60/038,179 filed Feb. 13, 1997 and 60/036,805 filed Feb. 14, 1997 both of which are incorporated herein by reference in their entirety.

TECHNICAL FIELD OF THE INVENTION

This invention relates to compositions and methods for monitoring changes in the local environment inside or outside of cells by detecting optical changes in an environment-sensitive reporter molecule. In particular, this invention relates to compositions which may be specifically incorporated into cells, or may be caused to be produced by them, which produce an optically detectable signal in response to a change in the environment in which the optically sensitive reporter molecule is present. This invention is particularly applicable to detecting the release of substances stored in exocytotic vesicles of cells, such as synaptic vesicles, wherein the compositions of the invention are localized in the vesicles and become exposed to the extracellular space upon release of the contents of the vesicles.

BACKGROUND OF THE INVENTION

Various methods are known for monitoring molecular changes in local environments at a microscopic level. Detection of changes in the microenvironments involving active cells presents a particular challenge because many methods involve destruction or damage to the cells being analyzed. Although significant information has been obtained using electrophysiological techniques, these techniques have limited application for studying complex real time cell physiology and also may damage and thereby alter the cells being recorded. Also, electrophysiology is limited to detecting events involving a change in electrical potential.

Many cell process involve changes in the molecular microenvironment. Such processes include, for example, exocytosis and endocytosis which involves contact between the intracellular and extracellular environments, and changes in ion concentration associated with electrically active cells such as neurons and muscle cells. The release of cellular substances, in particular, is a generalized phenomenon of several cell types which is fundamental to the function of multicellular organisms. Blood cells, endocrine cells and neurons are examples of cell types particularly dependent on such processes. Blood granulocytes, for example, release various mediators of inflammation through exocytosis; endocrine cells release hormones required by other cells; and neurons release neurotransmitters packaged in synaptic vesicles. The ability to detect changes in the microenvironment caused, for example, by the fusion of an exocytotic vesicle with a plasma membrane and contact of the lumenal surface and contents of the vesicle with the extracellular space would provide information useful for understanding and modulating processes which causes release of such cellular substances.

Exocytotic events are particularly important to the proper function of neurons since synaptic transmission is dependent upon the controlled release of synaptic vesicles. Many problems in neurophysiology can be reduced to questions about the location, timing, and magnitude of synaptic activity, including, for instance, the integration of inputs by a single neuron, synaptic plasticity, and pattern classification and storage by neural networks. The study of these and related problems would greatly benefit from a method that allows direct recording from many synapses simultaneously, with the capacity to reliably detect single exocytotic events. Such a method would appear optimal because, on the one hand, central synapses generally transmit information via the fusion of a single synaptic vesicle (1,2), while, on the other hand, the computational power of the nervous system arises from networks containing large numbers of synapses (refs. 3–5).

While current electrophysiological methods allow the activity of individual synapses to be recorded, they do not permit populations to be studied. There is a practical limit to the number of cells that can be impaled simultaneously with intracellular electrodes, and importantly, an invasive method requires an a priori decision on which cells to study, making discovery difficult. Extracellular field recordings with multiple electrodes avoids some of these problems and thereby allows the collective activities of many cells to be measured, but does not permit activity to be ascribed to individual synapses or neurons (6,7). Optical imaging of light emission from fluorescent indicators of membrane potential or intracellular $Ca^{2+}$ concentration (7–10) greatly increases spatial resolution but again, does not measure synaptic activity directly. An alternative optical approach that offers a direct gauge of synaptic activity is to load synaptic vesicles with fluorescent dyes and to observe dye release (11,12). However, this method is intrinsically incapable of resolving individual quanta, which can cause only a small decrease in total fluorescence. Despite their limitations, these techniques have opened a window on multicellular phenomena as diverse as the representation of visual scenes by retinal ganglion cells (13) and the emergence of cortical circuits during development (14). Methods that reveal the detailed patterns of synaptic inputs and outputs in entire networks can thus be expected to disclose important new physiological concepts operative at the relatively unexplored interface between cellular and systems neurophysiology.

Due to the importance to physiology of proper exocytotic processes in neurons and other cells types, it is therefore desirable to develop sensitive compositions and methods which can detect changes in the microenvironment inside or outside of cells including quantal exocytotic events in real time. Molecules which can detect changes in microenvironments would be useful as probes of cellular events involving changes in such microenvironments due to movement of molecules in solution or the spacial location of molecules associated with cell membranes. It would be particularly desirable to have available molecules that provided an optical signal upon encountering such a change in the microenvironment.

Various types of molecules have been used in the art for the detection of the presence of other molecular entities. Radiochemical labels have high sensitivity but are hazardous and must be used with appropriate caution. In addition, these labels are not useful for real time localization. Optical labels such as fluorescent molecules or other forms of dyes have also been coupled to molecules to act as reporters for the detection of specific molecular entities. Typically a reporter cable of generating an optical signal is bound to a specific binding molecule which is a member of a ligand binding pair. Such binding molecules are usually antibodies, specific binding proteins, e.g. receptors or peptide hormones which specifically binds a corresponding target ligand. These reporter-ligands are reagents which must be added from the external environment to the system under investigation. Their usefulness is therefore limited by their accessibility to the appropriate molecular target, nonspecific binding or diffusion to inappropriate locations and availability of appropriate binding pairs. Another type of molecular reporter comprises signal generating molecules expressed endogenously by a cell. Several bioluminescent proteins have been reported as useful as detectable labels for optically reporting the presence of a molecular entity.

The green fluorescent protein (GFP) of *Aequora victoria*, for example, is a naturally fluorescent protein with a p-hydroxybenzylideneimidazolone chromophore, created by in vivo cyclization and oxidation of the sequence Ser-Tyr-Gly (positions 65–67). The chromophore's phenolic group, derived from Tyr-66, exists in two states of protonation, which in all likelihood underlie the protein's two main excitation peaks at 395 and 475 nm (ref. 47). Several reports have characterized various bioluminescent proteins. See, for example, Cormier et al., "Recombinant DNA Vectors Capable of Expressing Apoaequorin", U.S. Pat. No. 5,422,266; Prasher, "Modified Apoaequorin Having Increased Bioluminescent Activity", U.S. Pat. No. 5,541,309; Cormier et al., "Isolated Renilla Luciferase And Method Of Use Thereof", U.S. Pat. No. 5,418,155; McElroy et al., "Recombinant Expression of Coleoptera Luciferase", U.S. Pat. No. 5,583,024. The use of bioluminescent fusion proteins as reporters of gene expression has also been reported. See, for example, Harpold et al., "Assay Methods And Compositions For Detecting And Evaluating The Intracellular Transduction Of An Extracellular Signal", U.S. Pat. No. 5,436,128; Tsein et al., "Modified Green Fluorescent Proteins". International Application WO 96/23810; Gustafson et al., "Fusion Reporter Gene For Bacterial Luciferase", U.S. Pat. No. 5,196,524; and Chalfie et al. "Uses Of Green-Fluorescent Protein", U.S. Pat. No. 5,491,084. Although GFP has been reported as a useful reporter molecule, its utility would be further enhanced if it could be made sensitive to changes in the microenvironment.

SUMMARY OF THE INVENTION

This invention provides compositions and methods useful for detecting changes in microenvironments. Many dynamic systems are dependent on compartmentalization of molecules with subsequent merging of compartments or release of the contents of one compartment into another compartment. Endocytosis and exocytosis are examples of biologic systems which involve compartmentalization of molecular entities. The compositions and methods of this invention are especially useful for detecting changes in the microenvironment associated with changes in compartmentalization. Detection of quantalcellular exocytotic events in real time such as those occurring in connection with the release of synaptic vesicles is made possible by this invention.

The method of this invention comprises detecting a change in the light emitting properties of a hybrid molecular reporter present in a first compartment upon contact with a second compartment. The hybrid molecular reporter comprises a targeting region and a reporter region which participates in a light-generating reaction upon contact with the second compartment. As applied to cells, the method of this invention enables the quantal detection of the release of components of exocytotic vesicles, especially synaptic vesicles. The method of this invention is anticipated to be applicable to detecting the release of vesicular contents within a cell as well.

This invention also provides hybrid molecular reporter molecules. At least two types of hybrid molecules are provided by this invention. One type of molecule is derived externally from the compartment in which it is to be introduced. When used to detect cellular processes, such hybrid molecules are typically not genetically encoded by the cells to which they are directed. In addition, the light-generating component provides a detectable optical signal which is environment sensitive. The other type of hybrid molecule provided by this invention is genetically encoded. These molecules themselves are of two types: a) those which include a targeting region and a reporter region wherein the reporter region is co-expressed with the targeting region and is capable of generating an optically detectable signal; and b) those which include a targeting region and a binding region which binds to a separate reporter molecule capable of generating an optically detectable signal but which is not encoded by the cell encoding the targeting-binding region and which is provided from the external environment.

The hybrid molecules of this invention are typically, but not necessarily, polypeptides since polypeptides are particularly well suited as targeting entities and may be genetically encoded and expressed. The compositions of this invention may be targeted to various types of multicompartment systems. In one embodiment, the hybrid molecules may be targeted to liposomes and used to monitor delivery to cells of substances, such as drugs contained by the liposomes. In another embodiment, the compositions of this invention may be targeted to intracellular locations, such as exocytotic vesicles, where they are not in contact with the extracellular environment until an exocytotic event occurs. Upon exocytosis, the interior of the exocytotic vesicle, including for example the lumenal side of the vesicle membrane, comes in contact with the extracellular environment. By coming into contact with the extracellular environment the compositions of this invention targeted to the vesicle cause a release of photons which may be detected as an optical event indicative of quantal exocytotic release.

The targeting polypeptide of the invention preferably is targeted to exocytotic vesicle membranes and the amino acid sequence required for generation of the optical signal is preferably located at the lumenal surface of the vesicle membranes. This embodiment encompasses molecules which generate an optical signal that directly reports neurotransmitter release. The detection of individual vesicle fusion events is made possible by this invention which also provides for the regeneration of probes for many rounds of recording. Preferred probes for this and other embodiments are genetically encoded proteins.

Genetic control of the expression of the probes of this invention allows recordings to be obtained from cells, cultures, tissue slices or exposed tissues of transgenic animals, and affords means to detect individual cells including neurons (by localized DNA transfer techniques), types of neurons (by cell-type specific promoters), or elements of a circuit (by recombinant viral vectors that spread through synaptic contacts). Such probes are useful for detecting the release of synaptic vesicle.

In one embodiment of this invention, hybrid reporter molecules which comprise a luciferase enzyme and at least a portion of a vesicle membrane protein are provided. These hybrid reporter molecules are referred to as "synaptolucins".

This invention also includes mutants of green fluorescent protein of *Aequora victoria* which exhibit environment sensitive excitation and/or emission spectra and are useful, for example, as reporter moieties in the hybrid molecules of this invention. Examples of environment-sensitive GFP mutants provided by this invention are various pH sensitive mutants, which are termed "pHluorins". Two preferred types of GFP mutants which are provided by this invention are mutants which, in response to a reduction in pH, from pH 7.4 to 5.5 exhibit attenuation or loss of the GFP excitation peak at 475 nm (ecliptic pHluorins) and mutants which exhibit an inverse in the ratio of the excitation peaks at 395 and 475 nm upon a reduction in pH from 7.4 to 6.0 (ratiometric pHluorins). The nucleic acid molecules encoding the amino acid sequences of these GFP mutants are also within the scope of this invention.

In another embodiment of this invention, hybrid reporter molecules which comprise a pHluorin and at least a portion of a vesicle membrane protein are provided. These hybrid reporter molecules are termed "synaptopHluorins".

In another embodiment of this invention, nucleic acid molecules are provided which encode for the hybrid reporter molecule polypeptides of this invention. Preferably, such nucleic acid molecules comprise a promoter which causes expression of the polypeptide in a specific cell. Also provided are vectors and transformed cells containing the nucleic acid molecules of this invention. Various types of cells may be transformed with the nucleic acids of this invention and include primary cells either in vivo or in vitro, cultured cells including cell lines and cells of transgenic animals. Transgenic animals which express the claimed nucleic acids are thus another embodiment of this invention.

The hybrid molecules and methods of this invention are useful for detecting contact of molecules in an environment with a second environment. This invention is particularly useful for detecting fusion events associated with cell membranes involving endo or exocytosis. In addition, fusion of liposomes containing the hybrid reporter molecules with cells may also be monitored according to this invention. Screening for molecules which alter exocytotic processes, especially in specific cell populations is also made possible by this invention. In addition, the method of this invention provides a means of simultaneously recording the activity of several cells, for example neuronal cells, because one can distinguish spatially, the source of multiple optical signals generated by the cellular release of the peptides provided by this invention.

By providing a means of detecting release of exocytotic vesicles in discrete cell populations this invention provides a means of identifying the contribution of specific proteins or cell processes to exocytosis by measuring such processes in cells which have been altered in some way, for example by the inactivation of certain genes believed to encode for certain proteins involved in such exocytotic processes. Thus, for example, the use of this invention with animals or cells in which certain genes have been "knocked out" may provide useful models for providing information regarding exocytosis in various cell types and under various conditions.

Through the use of the synaptopHluorins of this invention, synaptic transmission at individual boutons, as well as secretion in a variety of cell types may be non-invasively imaged by fluorescence microscopy. It is anticipated that the use of pHluorins can be extended to visualize such diverse trafficking processes as endocytosis, receptor activation, and intercompartmental translocation in individual cells or populations of designated cell types, in cultures, tissues, or intact transparent organisms.

The GFP mutants provided by this invention are useful as optical labels. These mutants may be bound to a specific binding molecule which is one member of a ligand binding pair to detect the presence of the other member of the ligand binding pair. These mutants may also be used as reporters of protein expression. Because of their pH sensitivity, these mutants may also be used to detect pH changes in their environment.

An object of this invention is to provide bifunctional polypeptides which may be localized to specific cell types, cell compartments, or cell locations and which participate in the generation of an optical signal upon contact of the polypeptide with the extracellular space.

Another object of this invention is to provide a method for optically detecting the release of the contents of exocytotic vesicles, especially for example, synaptic vesicles.

Another object of this invention is to provide a method of identifying processes and substances which regulate vesicle release.

Yet another object of this invention is to provide mutants of GFP which exhibit excitation and/or emission spectra which are sensitive to changes in the environment.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 2A–2F. Hippocampal neurons expressing synaptolucin-1, imaged by wide-field microscopy. About 60% of the neurons were infected by HSV transducing synaptolucin-1. Scale bar, 20 $\mu$m. FIG. 2A displays the synaptic map, revealed by loading nerve terminals with FM 4-64. The fluorescent signal from FM 4-64 was acquired at low intensifier gain and averaged over 32 video frames. FIGS. 2B–2E represent photon registrations accumulated from synaptolucin emissions over 30 seconds, obtained at 30 nM luciferin, maximum image intensifier gain, and a discriminator value for photon detection that suppressed background and equipment noise (photon counts in the presence of a depolarizing stimulus but the absence of luciferin) to an average of 1.06 photon registrations per 100-pixel field. The preparation was imaged successively in normokalemic solution (2B) and during three hyperkalemic challenges to induce exocytosis, performed in either the presence (FIGS. 2C and 2D) or the absence (FIG. 2E) of external $Ca^{2+}$. Ten minutes under resting conditions elapsed between each of the successive stimuli. The dashed red lines in FIGS. 2A–2C mark areas of stimulation-independent synaptolucin activity, in all likelihood due to virus-infected glial cells. Panel 2F superimposes the synaptolucin signal of FIG. 2C, colored here in red, onto a binary version of the synaptic map. The binary map was constructed by thresholding FIG. 2A such that pixels with an intensity above the $97^{th}$ percentile appear in black.

FIG. 5. Amino acid sequence of wild-type GFP (SEQ ID NO: 1).

FIG. 6. cDNA nucleic acid coding sequence of wild-type GFP (SEQ ID NO:2).

FIG. 7A. cDNA nucleic acid coding sequence of GFP mutant 1B11t (SEQ ID NO:3).

FIG. 7B. cDNA nucleic acid coding sequence of GFP mutant 14E12t (SEQ ID NO:4).

FIGS. 8A–8D. Excitation spectra of GFP mutants. The excitation spectra from 360 to 500 nm was determined at an emission wavelength of 510 nm at pH 7.4 (solid lines) and pH 5.5 (dashed lines) for wild type GFP (FIG. 8A), GFP mutant S202H (FIG. 8B), GFP mutant 1B11t (FIG. 8C) and GFP mutant 14E12t (FIG. 8D).

FIGS. 9A–9F. Excitation spectra of 1B11-like GFP mutants. Excitation spectra were obtained as described for FIGS. 8A–8D (clone 1D10, FIG. 9A; clone 2F10, FIG. 9B; clone 2H2, FIG. 9C; clone 1B11, FIG. 9D; clone 8F6, FIG. 9E; and clone 19E10, FIG. 9F).

FIGS. 10A–10G. Excitation spectra of 14E12-like GFP mutants. Excitation spectra were obtained as described for FIGS. 8A–8D (clone 14E12, FIG. 10A; clone 14C9, FIG. 10B; clone 14C8, FIG. 10C; clone 2G3, FIG. 10D; clone S202H, FIG. 10E; clone 14D9, FIG. 10F; and clone 8H8, FIG. 10G).

FIG. 11A. cDNA nucleic acid sequence for the coding region of clone 1D10 (SEQ ID NO:5).

FIG. 11B. cDNA nucleic acid sequence for the coding region of clone 2F10 (SEQ ID NO:6).

FIG. 11C. cDNA nucleic acid sequence for the coding region of clone 2H2 (SEQ ID NO:7).

FIG. 11D. cDNA nucleic acid sequence for the coding region of clone 1B11 (SEQ ID NO:8).

FIG. 11E. cDNA nucleic acid sequence for the coding region of clone 8F6 (SEQ ID NO:9).

FIG. 11F. cDNA nucleic acid sequence for the coding region of clone 19E10 (SEQ ID NO:10).

FIG. 12A. cDNA nucleic acid sequence for the coding region of clone 14E12: 14E12 (SEQ ID NO:11).

FIG. 12B. cDNA nucleic acid sequence for the coding region of clone 14C9 (SEQ ID NO: 12).

FIG. 12C. cDNA nucleic acid sequence for the coding region of clone 14C8 (SEQ ID NO: 13).

FIG. 12D. cDNA nucleic acid sequence for the coding region of clone 2G3 (SEQ ID NO: 14).

FIG. 12E. cDNA nucleic acid sequence for the coding region of clone S202H (SEQ ID NO: 15).

FIG. 12F. cDNA nucleic acid sequence for the coding region of clone 14D9 (SEQ ID NO:16).

FIG. 12G. cDNA nucleic acid sequence for the coding region of clone 8H8 (SEQ ID NO:17).

FIG. 13. cDNA nucleic acid sequence for the coding region of *Cypridina luciferase* (SEQ ID NO: 18)

In FIG. 14A, blue regions indicate cassettes of amino acids (positions 94–97, 146–149, 164–168, 202–205, 221–225) subjected to combinatorial mutagenesis. In FIG. 14B, blue regions indicate the 7 key residues and their side chains. The predominant side chain conformation of Thr$^{203}$ is shown.

Figure 14A:
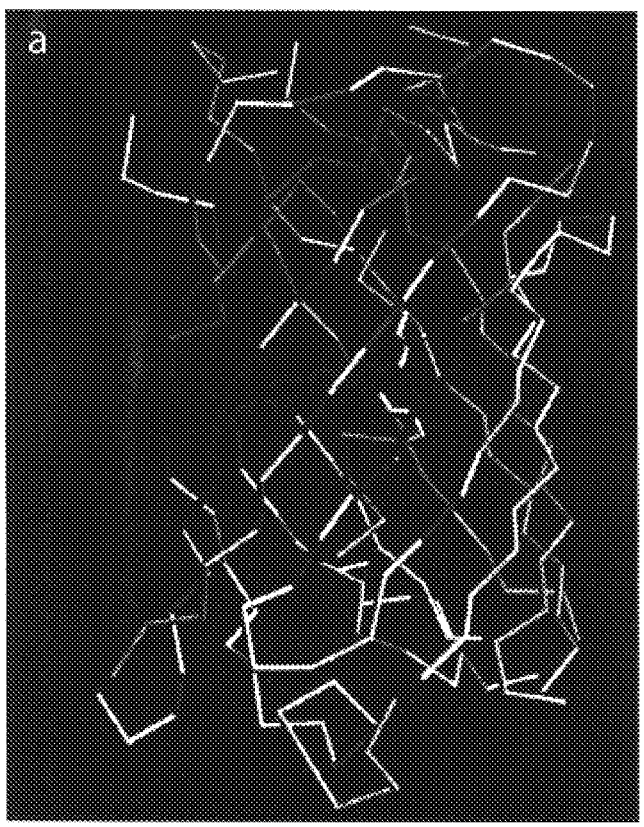
FIGS. 14A–14B. Side (14A) and top (14B) views of the beta-barrel structure of GFP. The polypeptide backbone is shown in grey and the chromophore, formed by internal cyclization of the tripeptide Ser$^{65}$-Tyr$^{66}$-Gly$^{67}$, in green; the hydroxyl group of Ty$^{66}$ is highlighted in red.
Figure 14B:
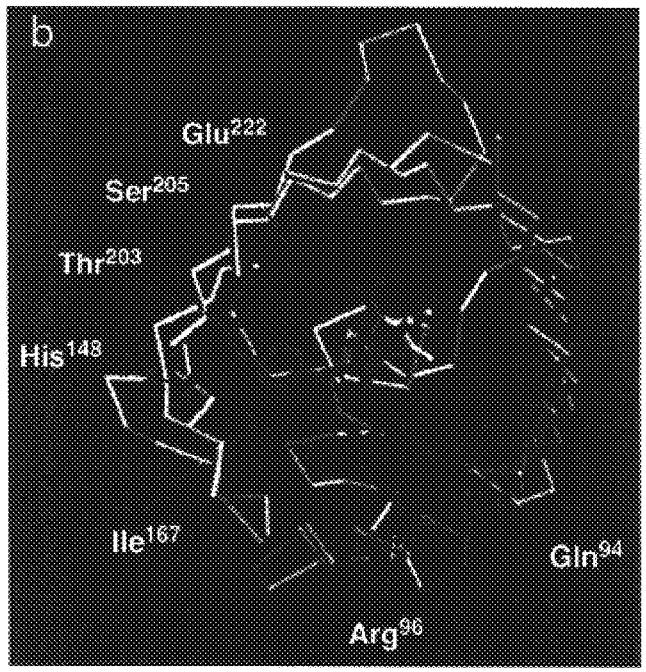
Figure 14C:
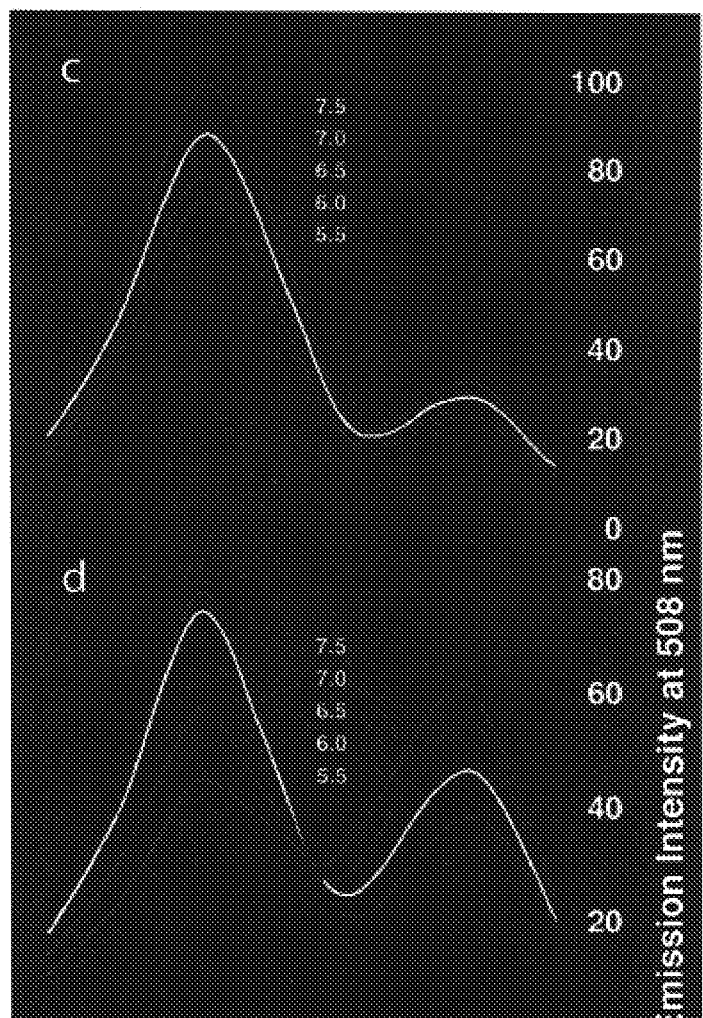
FIG. 14C. Excitation spectra at 508 nm of wild-type GFP.
Figure 14D:
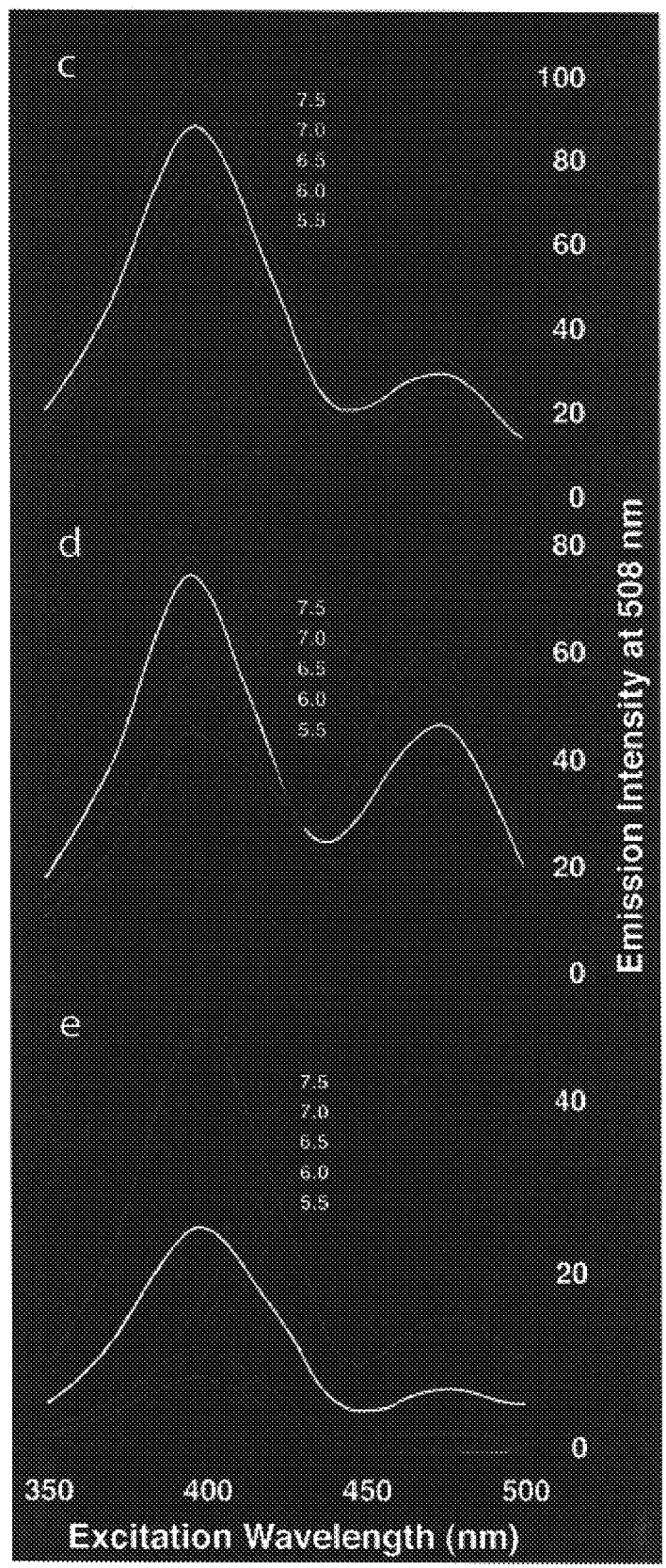
FIG. 14D. Excitation spectra at 508 nm of ratiometric pHluorin (clone C6).
Figure 14E:
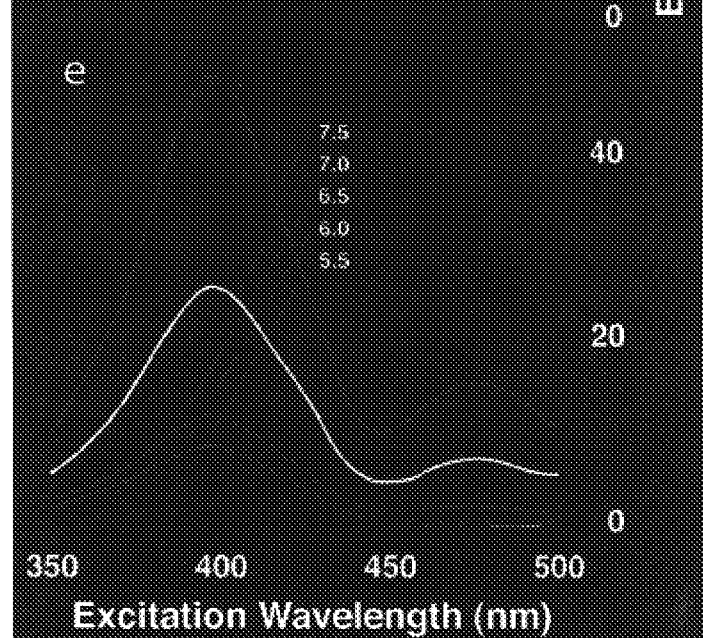
FIG. 14E. Excitation spectra at 508 nm of ecliptic pHluorin (clone 8F3).

The ordinate scales in FIGS. 14C–14E reflect normalized differences in emitted fluorescence intensity, recorded at 25° C. Samples contained 27.5 $\mu$M chromophore, 50 mM sodium cacodylate, 50 mM sodium acetate, 100 mM NaCl, 1 mM CaCl$_2$, and 1 mM MgCl$_2$.

Figures 15A, 15B, 15C, 15D, 15E:
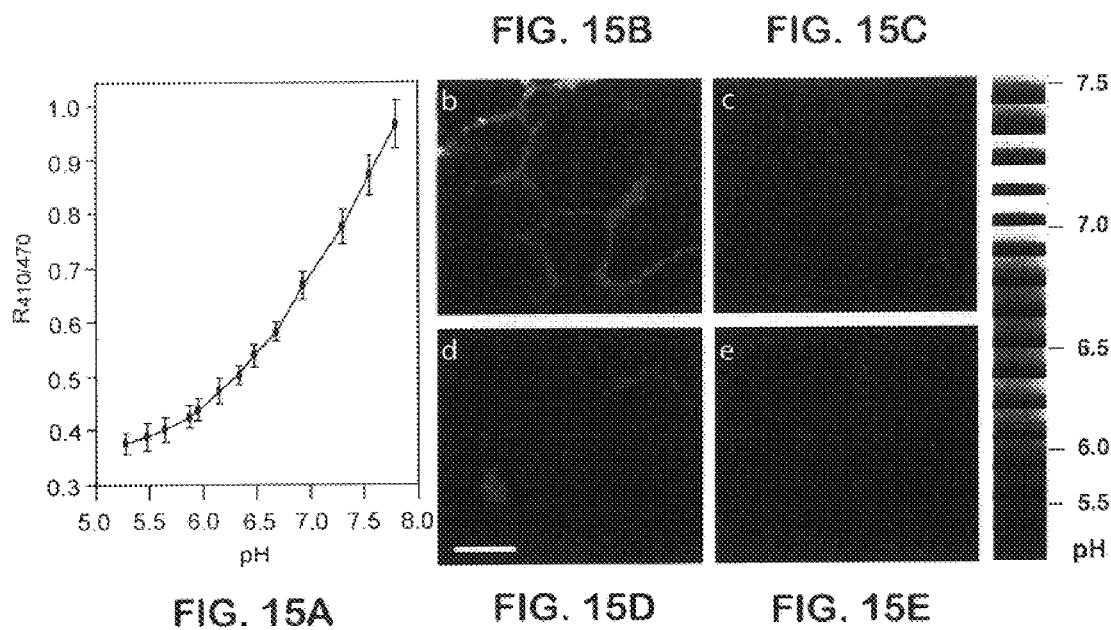

FIG. 15A. The relationship between $R_{410/470}$ (mean±SD) and pH. Cells expressing GPI-anchored ratiometric pHluorin at their surface (n=28) were imaged in imaging buffers adjusted to pH values between 5.28 and 7.8 (at 37° C.).

FIG. 15B. Ratiometric pH measurement of extracellular space, color encoded according to the look-up table displayed at right. The targeting module used was a GPI-anchor for delivery to the cell surface of transiently transfected HeLa cells, in imaging buffer of pH 7.4).

FIG. 15C. Ratiometric pH measurement of endosomes, color encoded according to the look-up table displayed at right. The targeting module used was Cellubrevin, in transiently transfected HeLa cells. Scale bar, 10 $\mu$m, is valid for FIGS. 15B–15E.

FIG. 15D. Ratiometric pH measurement of the trans-Golgi network, color encoded according to the look-up table displayed at right. The targeting module used was TGN38, in transiently transfected HeLa cells.

FIG. 15E. Ratiometric pH measurement of synaptic vesicles, color encoded according to the look-up table displayed at right. The targeting module used was VAMP/synaptobrevin, in hippocampal neurons infected with an HSV amplicon vector.

Figure 16A:
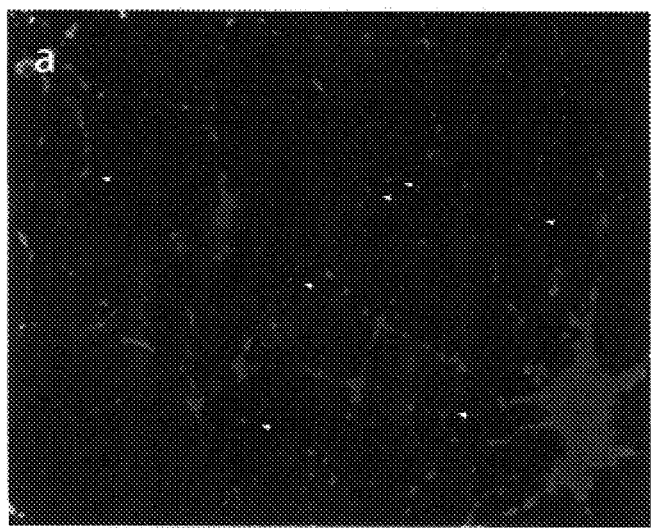

FIG. 16A. Map of all synapses in a field of hippocampal neurons, obtained by immunostaining with a monoclonal antibody against synaptotagmin-I. Note the numerous synaptic inputs to the cell body on the lower right.

Figure 16B:
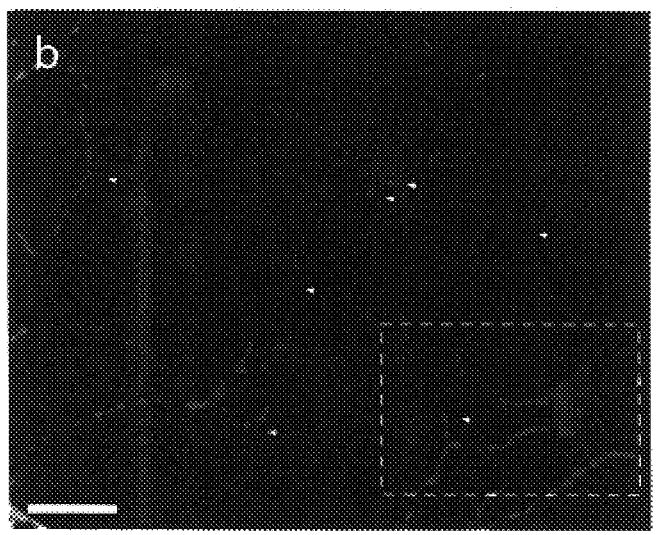

FIG. 16B. Map of synaptopHluorin-expressing synapses, formed by HSV-infected neurons whose somata lie outside the field of view. Due to the low multiplicity of infection, only a small fraction of the synapses labeled in FIG. 16A are synaptopHluorin-positive. Note the relative paucity of synaptopHluorin-positive inputs to the cell body on the lower right, attesting to the specificity of synaptopHluorin expression. Arrows indicate points of registration between FIGS. 16A and 16B. Scale bar, 20 μm.

Figure 16C:
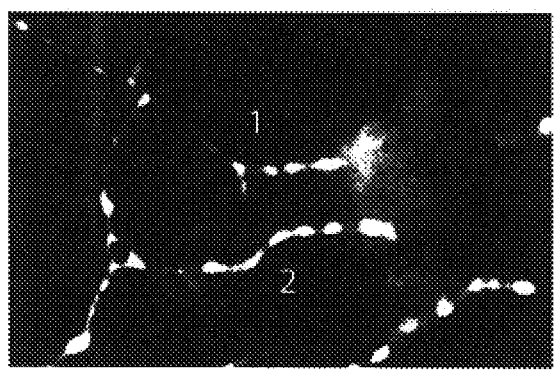

FIG. 16C. Photo: the dashed box in FIG. 16B, shown at higher magnification. Two boutons (1 and 2) are identified.

Figure 16D:
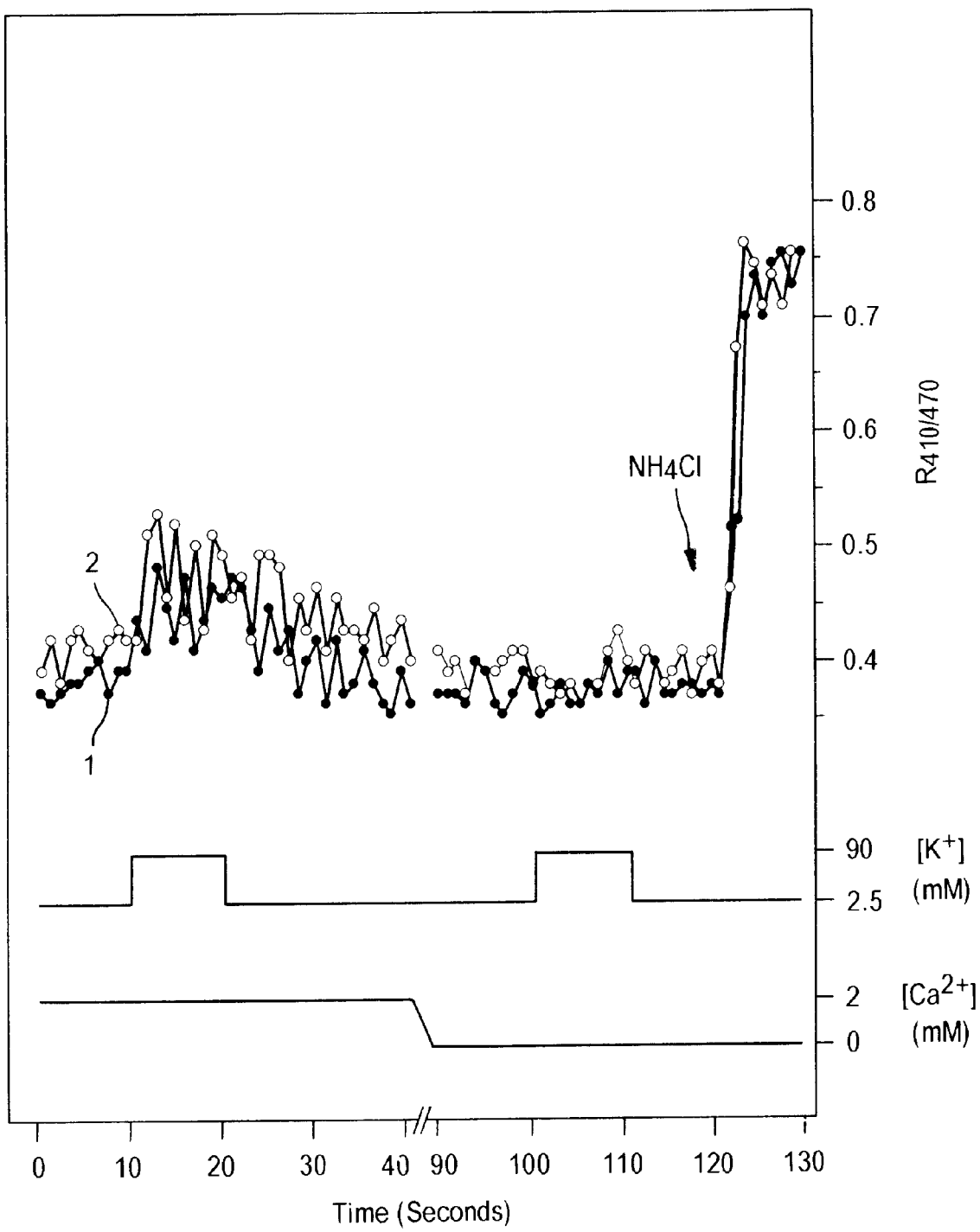

FIG. 16D. Recordings of synaptic activity obtained from the two boutons identified in FIG. 16C. $R_{410/470}$ was sampled at 1 Hz, with 200-msec exposures at each excitation wavelength. Neurons were stepped through two depolarization cycles by raising extracellular [$K^+$], first in 2 mM extracellular $Ca^{2+}$ (abscissa 0–40 sec) and then in the absence of $Ca^{2+}$ and in the presence of 2.5 mM EGTA (abscissa 90–130 sec).

Figure 17A:
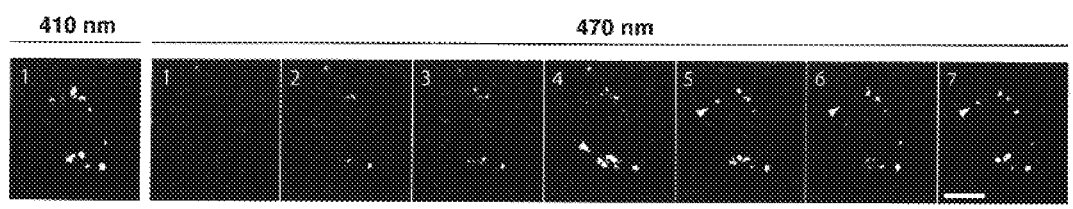

FIG. 17A. Secretion visualized with ecliptic pHluorin. RBL-2H3 cells expressing ecliptic pHluorin were pre-incubated for 3 h with 10 ng/ml anti-DNP IgE to load cell surface IgE receptors. Under resting conditions (frame 1), secretory granules are visible only with 410-nm but not with 470-nm excitation. After addition of 1 mg/ml anti-IgE antibodies to trigger a secretory response, 200-msec exposures were acquired at 0.1 Hz. Selected frames (2–7) taken with 470-nm excitation are displayed. All images were contrast-enhanced and low-pass filtered with a 3×3 binomial kernel. Scale bar, 10 μm.

Frame 4: arrows mark a cluster from which individual spots are disappearing in frames 5 and 6.

Frames 5–7: a "flickering" spot.

Figure 17B:
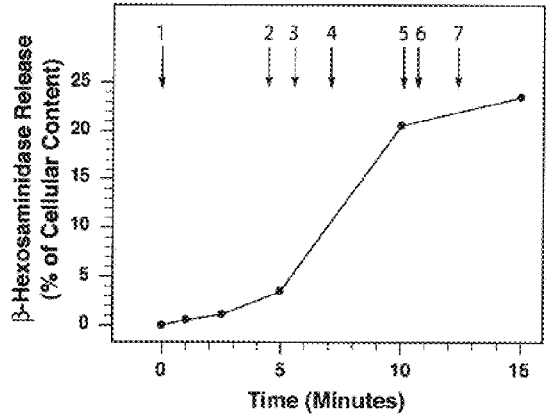

FIG. 17B. The relationship between optical and biochemical measures of secretion. Times at which individual frames in FIG. 17A were acquired are indicated by arrows. The activity of β-hexosaminidase, a marker enzyme of RBL cell granules, was assayed in 20-μl aliquots of imaging buffer, withdrawn at the indicated times.

Figure 17C:
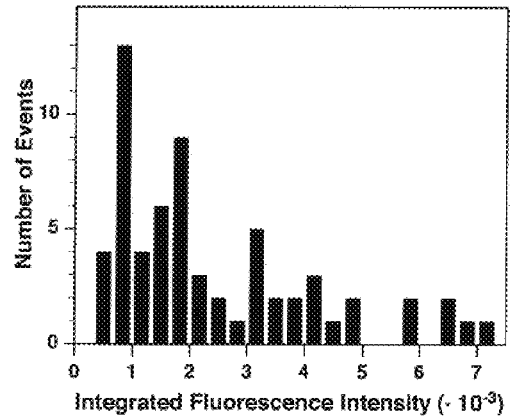

FIG. 17C. Size distribution of secretory events, derived from raw images acquired with 470-nm excitation. Integrated fluorescence intensity is the product of pixel area and average intensity. Events were counted if: 1) the grey level of each of their pixels exceeded a threshold which was empirically set so that no events would be scored in the absence of a secretory stimulus (frame 1) and 2) their area exceeded 4 contiguous pixels, equal in size to the in-focus image (Airy disk) of a fluorescent object with a diameter of ca. 0.5 μm, somewhat smaller than the average mast cell granule.

FIG. 18. DNA sequence of coding region of GFP mutant C6 (SEQ ID NO:19)

FIG. 19. Amino acid sequence of GFP mutant C6 (SEQ ID NO:20).

FIG. 20. DNA sequence of coding region of GFP mutant 8F3 (SEQ ID NO:21).

FIG. 21. Amino acid sequence of GFP mutant 8F3 (SEQ ID NO:22).

FIG. 22. Amino acid sequence of GFP 1B11t (SEQ ID NO:23).

FIG. 23. Amino acid sequence of GFP 14E12t (SEQ ID NO:24).

FIG. 24. Amino acid sequence of GFP 1D10 (SEQ ID NO:25).

FIG. 25. Amino acid sequence of GFP 2F10 (SEQ ID NO:26).

FIG. 26. Amino acid sequence of GFP 2H2 (SEQ ID NO:27).

FIG. 27. Amino acid sequence of GFP 1B11 (SEQ ID NO:28).

FIG. 28. Amino acid sequence of GFP 8F6 (SEQ ID NO:29).

FIG. 29. Amino acid sequence of GFP 19E10 (SEQ ID NO:30).

FIG. 30. Amino acid sequence of GFP 14E12 (SEQ ID NO:31).

FIG. 31. Amino acid sequence of GFP 14C9 (SEQ ID NO:32).

FIG. 32. Amino acid sequence of GFP 14C8 (SEQ ID NO:33).

FIG. 33. Amino acid sequence of GFP 2G3 (SEQ ID NO:34).

FIG. 34. Amino acid sequence of GFP S202H (SEQ ID NO:35).

FIG. 35. Amino acid sequence of GFP 8H8 (SEQ ID NO:36).

DETAILED DESCRIPTION OF THE INVENTION

This invention relates to compositions and methods for detecting changes in microenvironments useful for monitoring dynamic physiological processes.

Hybrid Polypeptide Compositions

The compositions of this invention include hybrid molecules comprising a targeting region and a reporter region capable of participating in a reaction resulting in an optically detectable signal when the hybrid molecule encounters a change in the microenvironment. These hybrid molecules are preferably polypeptides comprising at least one amino acid sequence which targets the hybrid molecule to a specific cell or intracellular location and at least one other amino acid sequence which functions as the reporter and participates in generating the optically detectable signal. Modifications of the basic structure are within the scope of this invention including, for example, molecules comprising a plurality of reporter amino acid sequences as a means of amplifying the optical signal. Whereas in many cases it will be desirable to use an amino acid sequence as the reporter region, other moieties capable of generating an optical signal such as fluorescent or fluorogenic molecules may also be used as the reporter region. As used herein, a fluorogenic molecule is a molecule which takes part, as a reagent or catalyst, in a bioluminescent or chemiluminescent reaction, or which takes part in a reaction which generates a fluorescent or luminescent species. Fluorogenic substrates are molecules whose processing by an appropriate enzyme results in the emission of light, for example luciferin. A linker comprising at least one amino acid may also be interposed between the targeting and reporter regions.

Another form of hybrid molecule according to this invention are molecules comprising a targeting region and a specific binding region which functions as one member of a ligand-binding pair which is recognizable by a separate molecular entity which functions as the reporter. Such hybrid molecules would therefore bind to affinity-based reagents which include, but are not limited to, antibodies, or fragments thereof, and other members of ligand-binding pairs. Preferably, the hybrid molecule is a polypeptide which is genetically encodable. These hybrid molecules may be endogenous or engineered structures. The separate light-generating reporter, such as a labeled antibody, which binds to the specific binding region of the hybrid molecule is generally not expressed by the cells expressing the hybrid molecule but is added to the system from the external environment.

The ability to detect the change in the microenvironment results from the combination of the choice of targeting region and reporter region. For example, a reporter region which when expressed would be constitutively capable of generating an optical signal may be turned off by being expressed as part of a molecule comprising a targeting region which targets the molecule to a region of the cell having an environment which does not provide the necessary environment to generate the detectable signal. Upon a change in the microenvironment, the reporter region would then generate the detectable optical signal. This change in microenvironment may result, for example, due to movement of the hybrid molecule to a different location resulting in exposure to the extracellular space where necessary substrates may be present or a change in pH occurs.

The hybrid polypeptide compositions of this invention are particularly useful for monitoring physiological changes in the microenvironment such as those which occur during exocytotic processes when the exocytotic vesicle fuses with the plasma membrane causing the internal contents of the vesicle to come in contact with the extracellular environment. To monitor such processes it is possible through this invention to load intracellular vesicles with the hybrid polypeptides of this invention and then detect the fusion of the vesicle with the plasma membrane. In a particularly preferred embodiment neuronal synaptic vesicles are caused to contain the hybrid molecules of this invention to enable the quantal detection of synaptic vesicle release.

Incorporation of the hybrid molecules of this invention in liposomes also provides a method for detecting the contact of the liposome and fusion with cell membranes. Liposomes are increasing being used as drug delivery systems. By inserting the hybrid reporter molecules of this invention into either the interior of the liposome or into its lipid bilayer one may then detect fusion of the liposome with a target membrane. One method of practicing this embodiment for example would be to load vesicles with a hybrid reporter molecule where the reporter moiety is self-quenching fluorophore. Upon fusion of the liposome with the target cell the fluorophore would be diluted causing an increase in fluorescence.

Nucleic Acid Molecules

Another embodiment of this invention are the nucleic acid molecules encoding the hybrid polypeptides. These nucleic acid molecules comprise at least one nucleic acid sequence encoding the targeting amino acid sequence in reading frame with at least one nucleic acid sequence encoding the reporter amino acid sequence. An additional nucleic acid sequence encoding an optional flexible amino acid linker may also be interposed in between the targeting and reporter encoding nucleic acid sequences. The length of the amino acid linker may be chosen to optimize accessibility of the reporter region of the molecule to the external environment while maintaining sufficient anchorage with the target region to maintain the molecule in the desired location. In one exemplary embodiment the linker is fifteen (15) or fewer amino acids in length. In another embodiment the linker is twelve (12) amino acids in length. Preferred amino acid linkers are —(Ser-Gly-Gly)$_4$ and —(Ser-Gly-Gly)$_2$-Thr-Gly-Gly.

The nucleic acid molecule of the invention preferably comprises a promoter sequence which causes expression of the hybrid polypeptide in a desired tissue and/or at a desired time. Thus, the promoter sequence also can contribute to targeting of the hybrid polypeptide. Tissue specific promoters are described in Short, "Nucleic Acid Construct Encoding A Nuclear Transport Peptide Operatively Linked To An Inducible Promoter", U.S. Pat. No. 5,589,392 which is incorporated herein by reference in its entirety, but see in particular Col. 8–10. Examples of preferred promoters include the promoters for the genes encoding synaptotagmin-I and VAMP/synaptobrevin-2 when the target is neuronal synaptic vesicles. Promoters for polypeptide hormones such as insulin (Bucchini et al., *Proc. Natl. Acad. Sci., USA*, 82:7815–7819 (1985), growth hormone, prolactin, (Crenshaw et al., *Genes and Development* 3:959–972 (1989), and proopiomelanacortin (Tremblay et al., *Proc. Natl. Acad. Sci., USA*, 85:8890–8894 (1988) which are released by exocytosis may be useful for targeting the hybrid molecules of the invention respectively to pancreatic beta cells, and various cells of the pituitary gland, depending on the genes they express.

Neuron-specific promoters may be used for targeting the hybrid molecules of this invention to the nervous system and specific neurons. Such promoters generally fall within two categories, those which are "neuron-specific housekeeping" promoters, and those which are cell-type specific. Neuronal "house-keeping" promoters, for example, may be selected from the promoter for the synapsin I gene (See, Sauerwald A. et al., *J. Biol. Chem.* 265:14932–14937 (1990) and neuron specific enolase (Sakimura K. et al., *Gene* 60:103–113 (1987). Promoters for specific cell types may include the tryptophan hydroxylase promoter for serotoninergic neurons (Stoll J. and Goldman, D., *J. Neurosci. Res.* 28:457–465 (1991); the choline acetyltransferase promoter L. B. *J. Neurochem.* 61:306–314 (1993); the dopamine beta hydroxylase promoter for adrenergic neurons (Shaskus, J. et al., *J. Biol. Chem.* 267:18821–18830 (1992).

The nucleic acid molecules of this invention may be inserted in various vectors, preferably viral vectors such HSV or adenovirus, to cause expression in the desired cells. The constructs for use in this invention should also contain the necessary initiation, termination, and control sequences for proper transcription and processing of the gene encoding the hybrid polypeptides of this invention. Target cells for the nucleic acid molecules of this invention may be in vitro or in vivo.

Methods for inserting DNA into cells are well known in the art and have also been reported in connection with introducing bioluminescent proteins into cells. For example, the following patents and patent application, which are all incorporated herein in their entirety by reference, refer to methods for using bioluminescent polypeptides as reporters of gene expression. Tsien et al., "Modified Green Fluorescent Proteins" International Application WO 96/23810; Gustafson et al., "Fusion Reporter Gene For Bacterial Luciferase", U.S. Pat. No. 5,196,524; and Chalfie et al. "Uses Of Green-Fluorescent Protein", U.S. Pat. No. 5,491,084. Methods for introducing the nucleic acids into cells include for example conventional gene transfection methods such as calcium phosphate co-precipitation, liposomal transfection (see Epand et al. U.S. Pat. No. 5,283,185 (which is incorporated herein in its entirety by reference), microinjection, electroporation, and infection or viral transduction. In addition, it is envisioned that the invention can encompass all or a portion of a viral sequence—containing vector, such as those described in P. Roy-Burman et al., U.S. Pat. No. 5,112,767 (which is incorporated herein by reference in its entirety) for targeting delivery of genes to specific tissues.

Transgenic animals, preferably non-human mammals such as mice or rats, or genetically tractable organisms such as *C. elegans*, Drosophila, and zebrafish, may also be produced which express the hybrid polypeptides encoded by the nucleic acid molecules of this invention. Methods for preparing transgenic animals are described in the art in Hogan et al., *Manipulating the Mouse Embryo: A Laboratory Manual*, Cold Spring Harbor, N.Y. (1987); Short, "Nucleic Acid Construct Encoding A Nuclear Transport Peptide Operatively Linked To An Inducible Promoter", U.S. Pat. No. 5,589,392; and Wagner et al., "Virus-Resistant Transgenic Mice", U.S. Pat. No. 5,175,385 (all of which are incorporated herein by reference in their entirety).

Targeting Amino Acid Sequences

The amino acid sequences which target the hybrid molecules of this invention may be entire proteins or fragments thereof which cause the hybrid molecule to be substantially localized to the desired target tissue and/or cell region. Transmembrane proteins specific for cell types are preferred for use with this invention and may include for example, receptors, ion channels, cell adhesion proteins (e.g. N-CAM) or vesicle docking proteins (e.g. synaptotagmin) and transport proteins. Antibodies, Fc fragments or other specific binding proteins may also be used since they would cause the hybrid molecule to be bound to specific antigenic recognition sites.

Preferably the polypeptides used for targeting the hybrid molecules are targeted to sites that are subject to changes in their microenvironment. For example, if the targeting moiety causes the hybrid molecule to be located intracellularly but becomes exposed to the extracellular space the hybrid molecule can be used to detect the time and location of such exposure to the extracellular environment provided the extracellular environment has the properties or substrate necessary to activate the reporter region of the hybrid molecule. In addition, it is preferable that such targeting polypeptides not be freely diffusable so as to avoid dilution of the optical signal and to keep the optical signal concentrated and localized at its site of generation. Accordingly, membrane proteins are especially preferred for use as the targeting region of the hybrid molecules of the invention. For detecting synaptic vesicle release synaptotagmin, VAMP/synaptobrevin are preferred.

In a preferred embodiment of this invention the hybrid molecules are engineered proteins consisting of two modules: a targeting module derived from a synaptic vesicle-specific integral membrane protein, and a light-generating module that is constitutively "off" but becomes activated when the vesicle fuses with the presynaptic membrane. In this way, light emission signals synaptic activity. Potential targeting modules may include any amino sequence which comprises at least one region which is lumenally exposed to provide an attachment site for the luminescent module. The targeting modules of this invention comprise an amino acid sequence which upon expression provides for targeting the sequence to a specific cellular location. In this case of synaptic vesicles this would preferably be the lumenal surface of synaptic vesicles. Such amino acid sequences preferably include a sequence sufficiently homologous to an endogenous protein to cause the sequence to be transported to the desired location. The targeting module may comprise a plurality of regions including at least one targeting region and at least one luminescent attachment site. The luminescent attachment site is not restricted to any particular portion of the targeting module provided it is accessible to the luminescent module if other portions of the targeting module are membrane bound or embedded within a membrane.

Reporter Regions

The reporter regions of the hybrid molecules of this invention may be any molecular moiety that participates in a bioluminescent, chemiluminescent, fluorescent, or fluorogenic reaction, or which participates in the quenching or suppressing of fluorescence or luminescence. Changes in light intensity or wavelength may be used to optically detect the presence or activation of the reporter moiety. Such reporter activity may result from ionic changes such as those resulting in pH changes, quenching, presence or absence of enzyme substrates, or ability to bind a second reagent, such as an antibody conjugate, which itself participates in generating an optically detectable signal.

Light-generating reporters typically are two-component systems, where light emitted by one component undergoes either a spectral or an intensity change due to a physical interaction of the first component with the second component. According to this invention, the first component may either be co-expressed as a fusion protein with the targeting region of the hybrid molecules, or it may bind to a specific binding site attached to the targeting molecule (see below). The second component of the light-generating system may be a molecule or ion, the concentration of which differs or can be made to differ in the various compartments which the first component contacts. An optical signal, and/or a change in the optical signal, is generated by movement of the light-generating component between the different compartments, or by contact of the light-generating component with different compartments.

Non-limiting examples of suitable light-emitting reporters, referred to herein as "fluorogens", for use with this invention include:

1. enzyme-substrate complexes (e.g. luciferases)
2. environmentally sensitive fluorophores as the first component, which can be genetically encodable (e.g., an environment-sensitive GFP mutant, infra) or not genetically encodable such as synthetic dyes such as, for example, fluorescein, SNAFL, SNARF, NERF, merocyanines, fura-2, etc. The second component which activates these light-generating components includes, but is not limited to, ions (e.g. protons, calcium ions, and any other endogenous or synthetic ions); or any other molecule which concentration differs, or can be made to differ, between the different compartments to be analyzed;
3. fluorescence resonance energy transfer pairs; and
4. self-quenching fluorophores, which exhibit increased fluorescence upon dilution into a larger compartment, such as the extracellular space.

The non-genetically encoded light-generating reporters may be bound to the member of the ligand pair which recognizes and binds the other member of the ligand binding pair associated with the target region in the compartment to be analyzed.

Where the hybrid molecule of this invention is itself to be added to cells for localization followed by activation by a reporter not expressed by the cells to be analyzed, the reporter may be any form of substance discussed above which is covalently bound to the targeting amino acid sequence such as an antibody or antibody fragment. Preferably, however, the reporter itself is an amino acid sequence which is co-expressed as a fusion protein with the targeting amino acid sequence as discussed above. Under such circumstances the optical signal is generated by a reporter amino acid sequence which is selected from the group consisting of a) amino acid sequences which contain a pH-sensitive chromophore or fluorophore, b) self-quenching fluorescent amino acid sequences which fluoresce upon dilution into a larger compartment (for example, into the extracellular space), c) enzymatic sequences which react with a fluorogenic substrate present in the extracellular space, and d) amino acid sequences which bind to a specific immunological reagent present in the extracellular space.

Several bioluminescent molecules are known in the art and are suitable for use with this invention as the reporter of the change in microenvironment. For example Cormier et al., "Recombinant DNA Vectors Capable of Expressing Apoaequorin", U.S. Pat. No. 5,422,266, which is incorporated herein in its entirety by reference, refers to recombinant DNA vectors capable of expressing the bioluminescent protein apoaequorin. In the presence of coelenterate luciferin, apoaequorin is termed aequorin and produces visible light in the presence of calcium ions. Various natural and modified luciferases are known. See, for example, Prasher, "Modified Apoaequorin Having Increased Bioluminescent Activity", U.S. Pat. No. 5,541,309, Tsien et al., supra. Examples of other luciferases suitable for use with this invention include Cormier et al., "Isolated Renilla Luciferase And Method Of Use Thereof", U.S. Pat. No. 5,418,155; McElroy et al., "Recombinant Expression of Coleoptera Luciferase", U.S. Pat. No. 5,583,024. Harpold et al., "Assay Methods And Compositions For Detecting And Evaluating The Intracellular Transduction Of An Extracellular Signal", U.S. Pat. No. 5,436,128 and that obtained from *Cypridina hilgendorfii* (29).

Green-fluorescent protein (GFP) is described in Chalfie et al. "Uses Of Green-Fluorescent Protein", U.S. Pat. No. 5,491,084. Certain modified forms of green-fluorescent protein have been reported and may be used with this invention, for example as described in Tsien et al., "Modified Green Fluorescent Proteins" International Application WO 96/23810. The GFP mutants described herein are particularly preferred for use as reporters in this invention.

For measurement of synaptic release the emitted signal must be of sufficient intensity to be detected upon release of a single synaptic vesicle. In addition, photon emission must be conditional upon synaptic vesicle exocytosis. In one embodiment, a luciferase acting on a membrane-impermeant substrate may be employed. If the substrate is present in the extracellular medium and the enzyme sequestered in synaptic vesicles, light emission can not occur, but once the vesicle fuses with the presynaptic membrane and the catalytic module is externalized, a burst of photon emission follows (FIG. 2C). Preferably, a useful luciferase is one that can i) catalyze a sufficiently high photon flux for imaging (a quantity dependent on the enzyme's turnover number and the quantum yield of the light-emitting complex), ii) use a membrane-impermeant substrate, iii) be capable of folding in the ER lumen and be targeted to synaptic vesicles, and iv) operate efficiently under the pH and salt conditions of the extracellular environment.

Of the well-characterized bioluminescent systems, that of the ostracod *Cypridina* (or *Vargula*) *hilgendorfii* (29) matches this profile remarkably well and is preferred. The commonly used firefly luciferase is less preferred for the reasons discussed below. Cypridina luciferase is a monomeric, naturally secreted glycoprotein of 62 kDa (16, 30) which can be expressed in and is secreted from transfected mammalian cells (31), whereas firefly luciferase is peroxisomal. Cypridina luciferin (32) carries a guanidino group expected to be positively charged at physiological pH and to thereby render the molecule slowly permeant or even impermeant to membranes. Unlike firefly luciferase, which requires ATP (and, for sustained activity, coenzyme A), Cypridina luciferase uses no cofactors other than water and $O_2$ (29). Its luminescent reaction proceeds optimally at pH 7.2 and physiological salt concentrations (30), whereas that of firefly is optimal at low ionic strength (activity is inhibited 5- to 10-fold by physiological salt), alkaline pH, and reducing conditions. With a turnover number of 1600 $min^{-1}$ (33) and a quantum yield of 0.29 (34), Cypridina luciferase produces a specific photon flux exceeding that of the optimized firefly system (35) by a factor of at least 50.

The GFP mutants provided by this invention may also be used as reporters since they too may be expressed as fusion proteins with the target regions.

Another form of reporter for use with this invention includes a binding region which is bound to the targeting region, which binding region specifically binds a separate light-generating reporter molecule. The binding region is preferably genetically encodable, and is most preferably co-expressed as a fusion protein with the targeting amino acid sequence. The separate light-generating reporter molecule to which the binding region specifically binds may be an antibody, a fragment of an antibody such as a Fab fragment, or any other moiety which is a ligand partner of the binding region attached to the targeting region. The separate light-generating reporter molecule will be labeled with a component which participates in producing a fluorogenic signal may then be detected by an appropriate method.

Any member of a ligand binding pair is suitable for use as the binding region provided the other member may be covalently attached to, or otherwise stably associated with, a light-generating reporter molecule. Preferably the binding regions are amino acid sequences recognizable by specific antibodies. Examples of such amino acid sequences which are recognized by commercially available antibodies include, but are not limited to:
1) myc-tag: EQKLISEEDL
   antibody: 9E10
   Evan, G. I., et al., (1985) *Mol. Cell. Biol.* 4:2843–2850,
2) Flag-tag: DYKDDDDK
   antibody: M2
   Brizzard, B. L., et al., (1994) *BioTechniques* 16: 730–734,
3 VSV-tag: YfDIEMNRLGK
   antibody: P5D4
   Kreis, T. E. (1986) *EMBO J.* 5:931–941, and
4) HA-tag: YPYDVPDYA
   antibody: 12CAS
   Wilson, I. A., et al., (1984) *Cell* 37: 767–778.

By expressing different binding regions in a single transgenic animal it is possible according to this invention to identify different populations of cells in a single preparation since different light-generating reporters may then be used.

Detection of the optical signal generated by the reporter may be accomplished using standard methods known in the art. Images may be recorded with a video or digital camera attached to a standard or fluorescent microscope, digitized and optically enhanced. Methods for amplifying the optical signal such as through the use of an intensifier photocathode may also be employed. Control images obtained prior to activation of the reporter region may also be digitized, electronically stored and subtracted from the image to remove background emissions to more accurately identify specific activation events such as those resulting from exocytosis.

As shown in the examples herein, the methods and compositions of this invention are especially useful for detecting release of exocytosis, as in synaptic vesicle release. The reproducible pattern of photon registrations in repeated trials (compare FIGS. 2C and 2D) attests to the reliability of synaptolucin and synaptopHluorin hybrid molecules of this invention as indicators of exocytosis, with many possible applications. For example, the interpretation of many studies on synaptic plasticity is fraught with controversy, possibly because the pre- and postsynaptic components of neurotransmission cannot be distinguished by traditional methods, which are all indirect (40). Measuring exocytosis directly via synaptolucins or synaptopHluorins, before and after maneuvers that alter synaptic strength, can help to resolve ambiguities. Or, the multiple inputs to a postsynaptic neuron can be mapped using synaptolucins or synaptopHluorins. If the postsynaptic neuron's membrane potential is monitored electrically, the shape of a synaptic potential as it arrives after propagation through the dendritic tree could be measured and immediately correlated with its anatomical site of origin, with important implications for input integration (5). The pattern of activation of individual synaptic inputs can be measured in relation to the activation of a post-synaptic neuron, affording a direct means of establishing firing rules.

The sensitivity and temporal resolution afforded by synaptolucins and synaptopHluorins are determined by three factors: the number of synaptolucin or synaptopHluorin molecules per vesicle, their specific emission rate, and the time over which photon counts can be integrated to keep pace with the relevant physiology. At video rates, this interval is usually a single video frame, or about 30 msec. At the other extreme, with long photon-counting times as in the present experiments, the timing of the synaptic vesicle cycle itself becomes limiting. In such cases, photon emission begins as a vesicle fuses with the presynaptic membrane—probabilistically (41,42), at any time during the observation period—and ends as the vesicle's reporter molecules are re-internalized—again, probabilistically—or when the camera shutter is closed. Vesicle recycling will terminate synaptolucin activity virtually instantaneously: if luciferin is taken up by recycling vesicles at its bulk concentration of 30 nM, only about one in a thousand recycled vesicles will contain a luciferin molecule (as can be calculated from the internal diameter of a synaptic vesicle of 50 nm), and those few which do will consume the internalized luciferin (via luciferase) rapidly. This effectively prevents the visualization of endocytosed vesicles, and limits photon emissions to the synaptolucin dwell time in the presynaptic membrane. In the case of the synaptopHluorins, the duration of fluorescence upon vesicle re-internalization will depend on the rate at which the intra-vesicular pH is re-established. It is anticipated that the synaptopHluorins will be useful for studying this phenomenon.

When using a Cypridina luciferase, luciferin should be used at subsaturating concentrations to minimize its penetration into cells, limiting luciferase to about 3% of its maximum velocity. Use of a truly impermeant luciferin derivative at saturating concentrations would increase photon emissions about 35-fold. In addition, the number of light-generating modules per synaptic vesicle can be increased i) by gene replacement technology to fully substitute synaptolucins for VAMP and/or synaptotagmin and ii) by including multiple light-generating modules in a single synaptolucin. Singly, or in combination, these engineering steps should permit reliable detection of single vesicle fusion events at every visible synapse.

The compositions and methods provided by this invention are useful for detecting changes in microenvironments, particularly those involving cells wherein different cell compartments contact each other or come in contact with the extracellular space. This invention is especially useful for detecting exocytotic events, especially the release of synaptic vesicles.

The ability to monitor such events is useful for providing new means of diagnosing disorders involving alterations of exocytosis. In addition, model systems involving cell cultures may be used to determine the effects of drugs on exocytotic processes. Not only may effects on release be monitored by this invention, but the rate of re-uptake of released material may also be monitored by detecting the rate of decrease in the signal intensity over time as dilution of the hybrid molecules occurs. This invention may therefore be particularly useful for identifying new drugs such as antidepressants which alter the neuronal release and/or re-uptake of neurotransmitters.

The pHluorins of this invention are useful for imaging many trafficking processes that connect compartments of differing pH. Secretory storage vesicles generally have an acidic pH (50), so that pHluorins, even in the form of a single VAMP-based construct (see FIGS. 16 and 17), can be used to monitor exocytosis. The controlled release of the contents of secretory vesicles underlies a great many intercellular signalling processes in homeostasis and development. Imaging of such events in cells, or in genetically tagged cell types in tissues or transgenic organisms, is of value in cell and developmental biology, as well as in physiology. The pHluorin method can also be adapted for high-throughput, cell-based screening for compounds affecting trafficking processes of medical relevance. Examples of transport pathways connecting the cell surface and acidic endosomes (50) include receptor-mediated endocytosis, the internalization of activated signalling receptors (such as tyrosine kinases (75) and G protein-coupled receptors (76)), and the translocation of glucose transporters to the cell surface in response to insulin (77).

SynaptopHluorins are anticipated to find many neurobiological applications. Because the probes are encodeable, specific types of neurons (for example, glutamatergic vs. GABAergic) can be tagged and recorded selectively. Because synaptopHluorins rely exclusively on cellular machinery for synthesis and localization, as well as for translating neurotransmission into optical signals, the activities of entire populations of neurons can be imaged in situ. This combination of self-sufficiency with anatomical and functional specificity promises to aid in visualizing the flow of information in complex neural systems.

As discussed above, this invention may be used with cell lines or primary cultures. In addition tissue slices from animals including the transgenic animals of this invention may be used. This invention may also be used on dissociated cells, organ cultures and dissected and exposed tissues of intact animals which are bathed in an appropriate medium. Because of its relative ease of accessibility, neurons of the myenteric plexus of intact animals are particularly well suited for analysis using the compositions and methods of this invention.

Where the hybrid molecules are added to the cells from the medium the cells are incubated with the medium for a sufficient time, typically several hours or overnight, to allow the molecules to be taken up by the cells and packaged for release. After an appropriate time the medium containing the hybrid molecule, is washed out and replaced with medium containing the necessary substrate or condition such as pH to cause activation of the reporter upon its contact with the extracellular space. Cells which have been made to express the hybrid molecules of the invention may be contacted with medium containing the activating conditions directly.

Environment-sensitive GFP Mutants (pHluorins)

Mutants of GFP of *Aequora victoria* are provided according to this invention by mutating amino acids which directly or indirectly interact with the natural chromophore p-hydroxybenzlideneimidazole, which is created by the in vivo cyclization and oxidation of the GFP Ser-Tyr-Gly sequence (positions 65–67).

Wild-type GFP has a bimodal excitation spectrum (54) with peaks at 395 and 475 nm (FIG. 1C). Underlying the two excitation maxima are protonated and deprotonated states of the chromophore (55–57), which are stabilized by different conformations of a hydrogen bond network involving the phenolic oxygen of $Tyr^{66}$, which is incorporated into the chromophore (55, 48, 58). The protonated form of $Tyr^{66}$ accounts for the 395-nm excitation maximum, while deprotonated $Tyr^{66}$, present in a smaller fraction of GFP, gives rise to the minor 475-nm peak (55–57). Excitation at either 395 or 475 nm results in virtually identical emission spectra, with a single maximum around 508 nm.

The excitation spectrum of GFP is essentially unaltered between pH 5.5 and 10 (54). Because water can access critical residues like $Tyr^{66}$, as evidenced by a pronounced deuterium kinetic isotope effect (56) on fluorescence excited at 395 nm, this lack of pH sensitivity implies that protonation-deprotonation reactions are conformationally constrained. In other words, a given GFP is kinetically trapped in either of two alternate conformations, in one of which the chromophore is protonated (and can be excited at 395 nm), and in the other of which it is deprotonated (and can be excited at 475 nm).

Wild-type GFP as obtained commercially (Clontech, Inc.) has the amino acid sequence depicted in FIG. 5. This sequence differs from that published in patent application WO 96/23810 in that a Thr is present, rather than an Ile, at position 161. Mutants of GFP may be identified by determining the excitation spectrum over a range of about 350 to about 500 nm at an emission wavelength of 508 nm. Alterations in the naturally occurring excitation peaks at 395 and 475 nm may thus be determined. Similarly, alterations in the emission spectrum may also be determined by scanning the emission spectrum from about 350 to about 500 nm at a constant excitation wavelength, preferably 395 nm which is the peak excitation wavelength at pH 7.4.

Amino acid residues in contact with, or in close proximity to, the GFP chromophore identify preferred regions for substituting one or more amino acids. Amino acids identified as being in preferred regions include Gln-69, Gln-94, Arg-96, Asn-121, His-148, Phe-165, Ile-167, Gln-183, Thr-203, Ser-205 and Glu-222. Most preferred are Gln-94, Arg-96, His-148, Ile-167, Thr-203, Ser-205, and Glu-222.

Amino acid substitutions are preferably made at residues flanking the above-identified amino acids since side chains of the flanking residues which are present in the beta-barrel structure face the outer surface of the protein and may therefore be more sensitive to the environment, especially-changes in pH. To create a pH sensitive mutant having a sensitivity at a particular pH range it is preferred to substitute one or more of the flanking amino acids identified above with amino acids having a side chain with a pKa within the range for which the mutant GFP is to be used to detect pH changes. Preferably the range is about one pH unit above and below the pKa. For example, histidine, having a pKa value of about 6.4, is preferred for obtaining mutants having pH sensitivity from about pH 5.5 to 7.5; glutamic acid, with a pKa of about 4.3, is preferred for mutants having a pH sensitivity of about 3.3 to 5.3; and lysine, having a pKa of 10.8, is preferred for mutants having a sensitivity of between about 9.8 to 11.8. Other substitutions may be made based on the known pKa's for particular amino acids.

Among the various positions which may be suitable for substitution with a pH sensitive amino acid, position 202 is preferred. Additional random mutagenesis of the regions in contact with or, in close proximity to, the chromophore may also be introduced to further modify the light emitting properties of the mutant GFP protein. Such additional mutations may further alter the light-emitting properties of GFP by quenching emitted photons or altering excitation properties of the protein.

The terminology used herein for referring to amino acid substitutions in the GFP mutants employs the notation XNY, where "X" is the single letter or three-letter amino acid code for the amino acid residue at position "N" in wild-type GFP, and "Y" is the single letter or three-letter code for the amino acid inserted at position N in place of X.

Amino acid substitutions suitable for preparing the GFP mutants of this invention include, but are not limited to, S147D, S147E, S147P, N149H, N149V, N149Q, N149T, N149L, N149D, N149Y, N149W, T161I, K163A, K166Q, I167V, R168H, S175G, and S202H. Preferred are S147D, N149Q, N149D, T161I, V163A, K166Q, I167V and S202H. More preferred combinations are those represented by clones 1B11t, 14E12t, 8F3, and C6. Most preferred are clones 8F3 and C6. The V163A and S175G mutations may optionally be included to decrease the temperature sensitivity of the mutant GFPs.

GFP mutants prepared according to the methods of this invention may also contain substitutions of amino acids of the wild type protein with amino acids of similar charge. See Yang et al., "The Molecular Structure Of Green Fluorescent Protein," *Nature Biotechnology*, 14:1246–1251 (1996) which is incorporated herein by reference for a report of the shape and topology of GFP.

Two classes of pH sensitive mutants are provided by way of example. The mutants of one class exhibit attenuation or loss of the excitation peak at 475 nm and a loss of fluorescence intensity excitable at 395 nm. Preferred members of the class include the clones 8F3, 1D10, 2F10, 2H2, 1B11, 8F6 and 19E10. See Table 2, infra. Most preferred is clone 8F3. The second class of pH sensitive mutants responds to decreases in pH with decreased fluorescence due to decreased excitation at the 395 nm peak and increased fluorescence due to increased excitation at the 475 nm peak. Preferred members of this class include clones C6, 14E12, 14C9, 14C8, 2G3, S202, H14D9, and 8H8. Most preferred is C6.

Mutants of the 8F3 class (ecliptic pHluorins) are preferred for use for detecting release of secretory granules. Secretory granules contain a proton pump of the vacuolar type. The proton pump generates a proton-motive force (pmf) across the synaptic vesicle membrane, consisting of a pH gradient (vesicle lumen acidic, pH ca. 5.5) and a membrane potential (vesicle lumen positive). When a synaptopHluorin utilizing 8F3 as the light-generating module is targeted to a secretory vesicle, the acidic intravesicular pH will turn the excitation peak at 475 nm off. Light emission after excitation at 475 nm, however, will resume at the more alkaline pH prevalent in the synaptic cleft, allowing an optical signal to be associated with exocytosis. This signal is large enough to permit detection of individual vesicle fusion events in real time.

The dynamic range of the signal generated by mutant C6 between pH 7.4 and 5.5 is too small to allow detection of individual vesicle fusion events. However, C6 and other ratiometric pHluorins, fused to an appropriate targeting module, are ideally suited to serve as ratiometric pH indicators for dynamic compartments such as intracellular organelles.

The GFP mutants and the Cypridina luciferase provided by this invention may be used for any application for which it is desirable to have a light-emitting detectable signal. Such mutants may therefore be used to detect the presence of an analyte in standard immunometric assays by coupling the GFP mutant or the Cypridina luciferase to an appropriate binding ligand using techniques well known in the art for conjugating proteins to other molecules. The GFP mutants and the Cypridina luciferase may also be expressed as fusion proteins and act as reporters of expression. Bound to such fusion proteins, the environment sensitive mutants may be used to spatially detect in real time the location of the expressed protein.

The nucleic acid molecules encoding the GFP mutants and the Cypridina luciferase are also within the scope of this invention. The nucleic acid sequences encoding the amino acid sequences disclosed in Table 2, as well as the specific nucleic acid sequences of FIG. 5 (GFP) and FIG. 13 (Cypridina luciferase), are preferred. These nucleic acid molecules may be incorporated into plasmids, and expression vectors for expression in various cells including bacteria cells such as *E. coli*, fungi, such as yeast, and mammalian cells by methods well known in the art. Expression in nearly transparent animals such as *C. elegans* and zebra fish is preferred.

Alterations to the nucleic acid sequences disclosed herein, which do not alter the amino acid sequence of the encoded polypeptide but which make translation of the nucleic acid sequence more efficient with respect to the preferred codon usage of the expressing cells, are within the ability of those skilled in the art, and nucleic acid sequences modified in this manner are also contemplated to be within the scope of this invention.

EXAMPLES

Example 1

Synaptolucins

Synaptolucins. Total Cypridina RNA extracted with TRI-SOLV (Biotecx; Houston, Tex.) served as the template for the RT-PCR synthesis of a cDNA encoding the luciferase (16). The PCR product was subcloned into the amplicon plasmid pα4"a" (17,18) and its sequence determined with SEQUENASE 2.0 (United States Biochemical; Cleveland, Ohio). To construct synaptolucins-1 and -2, the appropriate portions of the open reading frames for Cypridina luciferase (16) and, respectively, rat synaptotagmin-I (19) and VAMP/synaptobrevin-2 (20,21) were fused via stretches of nucleotides encoding the flexible linker —(Ser-Gly-Gly)$_4$—.

The amplicon plasmids were transfected into E5 cells (17,22) with the help of LIPOFECTAMINE (Gibco BRL; Bethesda, Md.), and replicated and packaged into virions after infection with 0.1 PFU/cel of the HSV deletion mutant d120 (22). The primary virus stock was passaged on E5 cells until the vector-to-helper ratio exceeded 1:4; the ratio was estimated as the number of synaptolucin-positive Vero cells (by immunostaining, using mAbs M48 (23) and CL67.1 (24)) vs. the number of viral plaques formed after infection of E5 cells.

PC12 Cells were infected at a multiplicity of 1 amplicon virion/cell and at 6 h p.i. harvested in buffer H (10 mM HEPES-NaOH, pH 7.4, 150 mM NaCl, 0.1 mM MgCl$_2$, 1 mM EGTA, 1 mM PMSF and 1 μg/ml each of aprotinin, leupeptin and pepstatin). Homogenates were prepared by 13 passes through a ball-bearing cell cracker and postnuclear supernatants (5 min at 5,000 g) fractionated on 5–25% (w/v) glycerol gradients in a Beckman SW41 rotor, operated for 2 h at 41,000 rpm (25). Gradient fractions were analyzed by SDS-PAGE, Western blotting, and immunostaining.

To measure synaptolucin activities, postnuclear supernatants were solubilized on ice with 1% NONIDET P-40, clarified (10 min at 15,000 g), and diluted 50-fold into buffer L (20 mM HEPES-NaOH, pH 7.4, 150 mM NaCl, 2 35 mM CaCl$_2$, 2 mM MgCl$_2$) that had been prewarmed to 30° C. After addition of Cypridina luciferin to 5 1 μM, photon fluxes were integrated for 10 sec in an LXB 1250 luminometer calibrated with a [$^{14}$C]hexadecane standard (26). Synaptolucin concentrations were determined by quantitative immunoblotting with mAbs M48 (23) and CL67.1 (24) and [$^{125}$I]protein G (New England Nuclear; Boston, Mass.), using the recombinant cytoplasmic domains of synaptotagmin and VAMP as the standards.

Hippocampal Neurons. The hippocampal CA1–CA3 fields of P1 Sprague-Dawley rats were dissected into EBSS with 10 mM HEPES-NaOH, pH 7.0, and mechanically dissociated after treatment with 20 U/ml papain (Worthington; Freehold, N.J.) (27,28). Cells were plated onto the poly-D-lysine- and laminin-coated surface of 35-mm dishes with central 8-mm glass windows (adhesive substrates were from Sigma Chemical Corp.; St. Louis, Mo.). The cultures were maintained in BME with Earle's salts and 25 mM HEPES-NaOH, pH 7.4, supplemented with 20 mM glucose, 1 mM sodium pyruvate, 10% fetal bovine serum, 0.1% MITO+Serum Extender (Collaborative Biomedical Products; Bedford, Mass.), 100 U/ml penicillin, 0.1 mg/ml streptomycin, and from day 5 after plating, 5 μM cytosine arabinoside (Sigma Chemical Corp.) (28). The preparations were infected with HSV amplicon vectors after 1–2 weeks in vitro. Viral inocula were diluted to multiplicities of roughly 0.1 in conditioned medium containing 1 mM kynurenate (Fluka; Buchs, Switzerland), adsorbed for 1 h, removed, and replaced with conditioned medium.

Optical Recording. At 8–20 h p.i., culture dishes were transferred to a PDMI-2 microincubator (Medical Systems Corp., Greenvale, N.Y.) mounted on the stage of a Zeiss AXIOVERT 135 TV microscope and held at 30° C. A teflon insert forming an 8 mm wide channel across the optical window was placed in the dish to allow rapid perfusion with either normokalemic solution (25 mM HEPES-NaOH, pH 7.05, 119 mM NaCl, 2.5 mM KCl, 2 mM NaCl$_2$, 2 mM MgCl$_2$, 30 mM glucose) or its hyperkalemic counterpart (KCl raised to 90 mM, NaCl reduced to 31.5 mM). Nerve terminals were stained by a 1-min exposure to 3 μM FM 4-64 (Molecular Probes; Eugene, Oreg.) in hyperkalemic solution (12) with 1% dialyzed bovine serum, followed by superfusion with normokalemic solution for >10 min.

FM 4-64 fluorescence was excited with the 510–560 nm band of an attenuated xenon arc lamp; alternatively, synaptolucin bioluminescence was initiated by adding 30 nM luciferin from a 30 μM methanolic stock. Emitted light was collected with a Zeiss 40×/1.3 NA PLAN-NEOFLUAR oil immersion objective, 590 nm longpass-filtered in the case of FM 4-64 fluorescence, and focussed onto the photocathode of a C2400-30H image intensifier coupled to a C2400-75 charge-coupled device (both from Hamamatsu Photonics; Hamamatsu, Japan). The video signal was 8-bit digitized in an ARGUS-20 image processor (Hamamatsu Photonics) and saved to a POWER MACINTOSH for analysis, using NIH Image 1.60 (http://rsb.info.nih.gov/nih-image/), TRANSFORM 3.3 (Fortner Research LLC; Sterling, Va.), and MATHEMATICA 3.0 (Wolfram Research; Champaign, Ill.).

The cDNA encoding Cypridina luciferase was used to construct two synaptolucins. In synaptolucin-1, the C-terminus of luciferase was fused to the N-terminus of synaptotagmin-1, located in the lumen of synaptic vesicles. The hybrid protein relies on the cleavable signal peptide encoded by the luciferase gene for membrane translocation and is anchored in the membrane of the synaptic vesicle by the transmembrane domain of synaptotagmin. In synaptolucin-2, the mature N-terminus of luciferase is fused to the C-terminus of VAMP-2, located in the vesicle lumen. This results in a second type of hybrid protein with a membrane-anchor segment that also serves as a non-cleavable signal sequence. The luciferase cDNA which was obtained (GenBank accession number U89490) differed from the published DNA sequence (ref. 16) at 30 positions, only three of which gave rise to amino acid substitutions: Asp-16 →Val, Ile-346 →Leu, and Asn-495 →Ser. The first substitution shifted the predicted signal peptide cleavage site (16), leading us to consider Gln-19 the mature N-terminus and to construct synaptolucin-2 accordingly. The cDNA nucleic acid sequence encoding the Cypridina luciferase, which is also considered part of this invention, is shown in FIG. 13.

Figure 1:
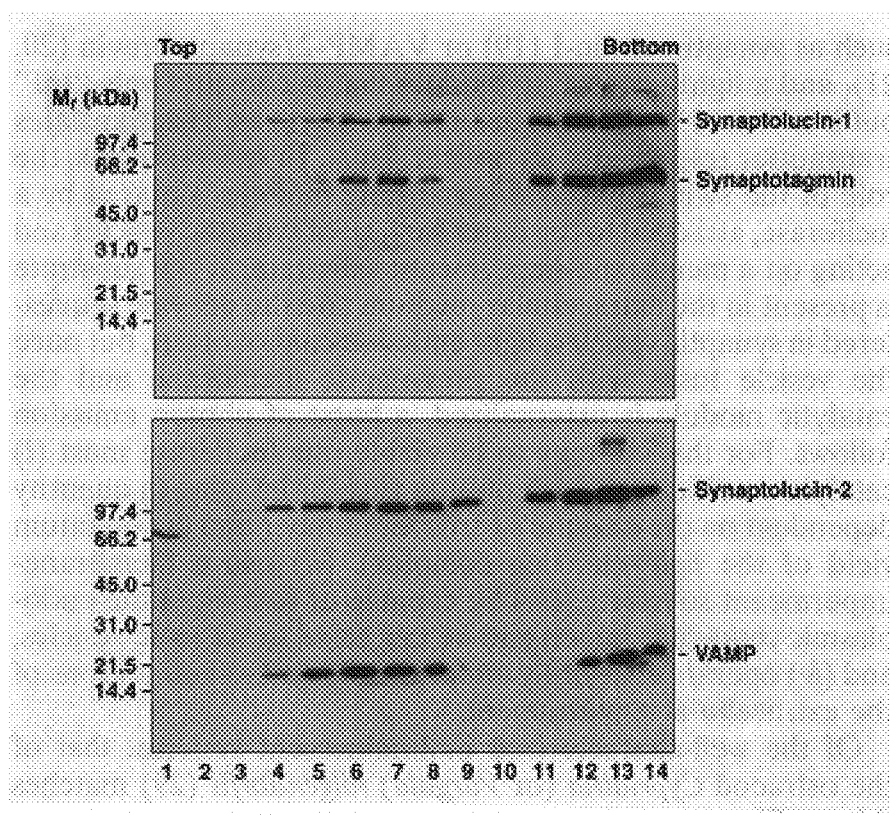
FIG. 1. Cofractionation of synaptolucins with synaptic vesicle proteins. Amplicon-infected PC12 cells were homogenized and postnuclear supernatants sedimented into 5–25% glycerol gradients. Small synaptic vesicles band in fractions 4–9, endosomes in fractions 11–14 (ref. 25). The bottom fractions contain material collected on sucrose cushions. Compared to the slower-sedimenting fractions, only 15% of this material was analyzed by SDS-PAGE. Proteins were precipitated with trichloroacetic acid, separated on 8–18% gels, and transferred to nitrocellulose. The filters were probed with mAb M48 (ref. 23), directed against synaptotagmin-I (top), or mAb CL67.1 (ref. 24), directed against VAMP-2 (bottom). Bound antibodies were visualized by ECL (Amersham; Arlington Heights, Ill.).

When expressed in PC12 cells, the synaptolucin genes directed the synthesis of membrane proteins of the expected sizes which co-sedimented with their respective targeting modules in velocity gradients (FIG. 1). The synaptolucins, like VAMP and synaptotagmin, were found both in synaptic vesicles (fractions 4–9) and endosomes (fractions 11–14) (25). Both synaptolucins were enzymatically active, with a $k_{cat}$ of 5.2 and 3.7 photon emissions $sec^{-1}$ per synaptolucin-1 and -2 molecule, respectively.

Imaging Neurotransmitter Release. Initial experiments on hippocampal neurons, performed at a saturating luciferin concentration of 5 $\mu$M (30), revealed that a depolarizing stimulus was not required for photon emissions to occur. It was suspected that this signal arose from the intracellular synaptolucin pool, which would become visible if Cypridina luciferin, an imidazo[1,2-a]pyrazine nucleus with mostly hydrophobic substitutions (32), crossed biological membranes once its guanidino group was deprotonated. Thus, the pH of the bath solutions was lowered from 7.4 to 7.05, to favor the protonated luciferin species, and the luciferin content was decreased to reduce diffusion across membranes. Indeed, at a luciferin concentration of 30 nM, the background signal disappeared and photon emissions became stimulation-dependent. However, longer photon-counting times were required because at a luciferin concentration so far below the $K_m$ of luciferase (0.52 $\mu$M, ref. 30), synaptolucin operated at only 3% of its $V_{max}$.

FIG. 2 illustrates a typical imaging experiment on hippocampal neurons infected with an HSV amplicon vector transducing synaptolucin-1. We first obtained a map of the synapses within the field of view (FIG. 2A) by taking the preparation through a depolarization cycle (12) in the presence of FM 4-64 (36), a member of the family of fluorescent dyes that are known to stain recycling synaptic vesicles (11). FM 4-64 was chosen over the more widely used FM 1-43 (11,12) because it does not absorb significantly at 462 nm, the emission wavelength of Cypridina luciferin (34), and thus permits the acquisition of an unperturbed synaptolucin signal from a stained preparation. After perfusion with normokalemic solution for at least 10 min, sufficient to replenish the synaptic vesicle pool and to remove excess FM 4-64, a bolus of luciferin was added to the bath solution and photon emissions were counted for the next 30 sec. In many cases, such as the one shown in FIG. 2B, some photons were registered in the absence of a depolarizing stimulus, but these originated mainly from regions without an appreciable density of synapses (compare the areas marked by dashed red lines in FIGS. 2A and 2B). It is likely that HSV-infected glial cells in the mixed culture are the source of this background signal, because the neurotropism of HSV in hippocampal cultures is incomplete (17), and because synaptotagmin, the targeting module of synaptolucin-1, appears at the cell surface when expressed in non-neuronal cells (37). More precise targeting may be accomplished by using neuron-specific promoters.

To record light emission resulting from synaptic activation, the hippocampal preparation was perfused with hyperkalemic solution to depolarize the neurons, open voltage-gated $Ca^{2+}$ channels in presynaptic terminals, and trigger exocytosis. Because Cypridina luciferin is unstable in aqueous solution, decomposing with a $t_{1/2}$ on the order of 1 min (29,30), a second bolus of luciferin was added immediately after depolarization, and photons were counted for 30 sec thereafter. A far greater number of photons were registered than in the absence of a stimulus, and now their pattern (FIG. 2C) was similar to the synaptic map recorded with FM 4-64 (FIG. 2A). The match, however, was imperfect, presumably because the synaptolucin image contained background emissions from virus-infected glial cells (compare the areas marked by dashed red lines in FIG. 2B and 2C), and because only a subset of synapses (those formed by neurons that are virus-infected) are potential light sources. Repeating the depolarization after a 10-min resting period evoked a similar but not entirely identical response (FIG. 2D), whereas depolarization without $Ca^{2+}$ influx (by omitting free $Ca^{2+}$ from the hyperkalemic solution) left the photon count at baseline level, with photon emissions only from the regions attributed to glial cells (compare FIG. 2E and 2B).

Figure 3:
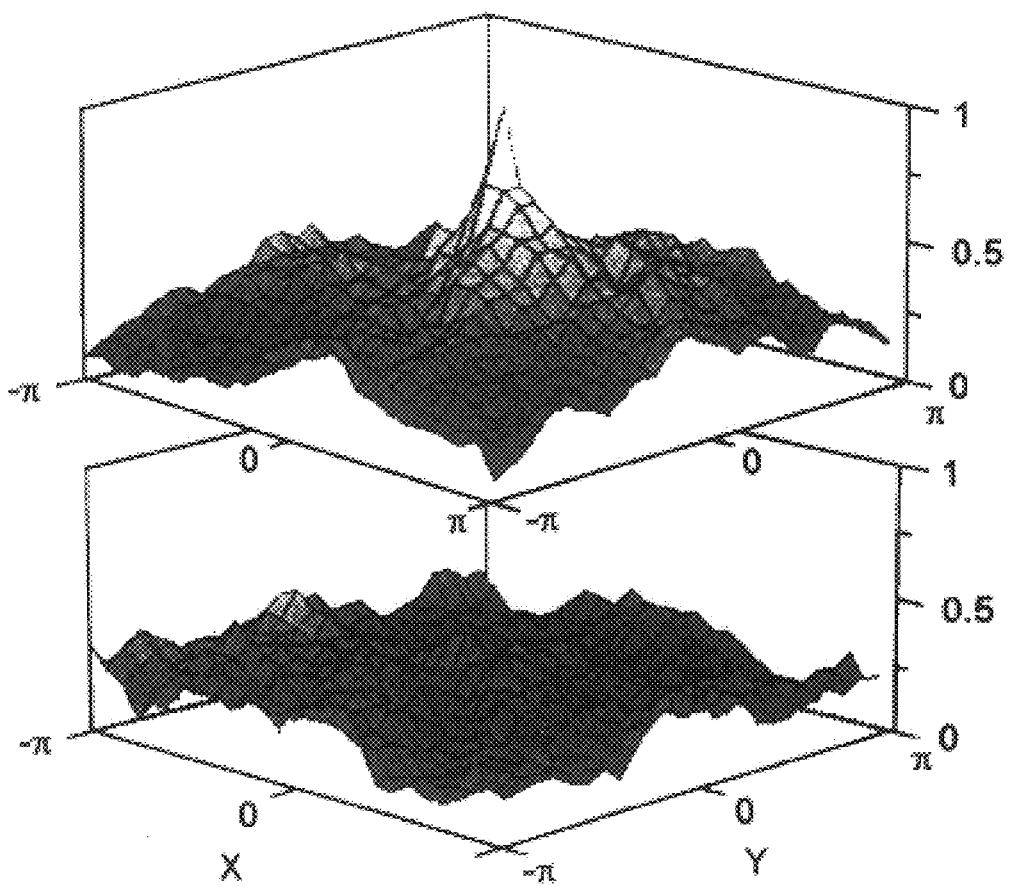
FIG. 3. Matched filtering of two synaptolucin images, FIGS. 2B (control) and 2C (exocytosis triggered), with their common synaptic map, FIG. 2A, as shown schematically in FIG. 2F. The x- and y-axes indicate the relative shifts between filter and image in these projections, and the ordinate the normalized cross-correlation function, a measure of the match between image and filter (Ref. 38). The function is computed by pointwise multiplication in the spatial frequency domain and—due to the properties of the Fourier transform—periodic (Ref. 38). Only a single period, from $-\pi$ to $\pi$ in the x- and y-directions, is shown. At shift (0,0), filter and image are in register, at shifts (x,+/−π) or (+/−π,y), the filter's center is displaced to an edge of the image. (Top) Scanning of FIG. 2C, showing evoked synaptolucin emissions. Note the peak at a filter shift of (0,0), indicating a matching structure in the image. (Bottom) Scanning of FIG. 2B, lacking evoked synaptolucin emissions. Note the absence of a central peak.

To examine the degree of correspondence between the sites of synaptolucin activity and the synaptic map more rigorously, photon-counting images were overlaid with a binary filter constructed from the synaptic map, FIG. 2A, as depicted schematically in FIG. 2F. The filter was chosen such that it "transmitted" only at pixels where the intensity of FM 4-64 fluorescence exceeded the $97^{th}$ percentile of the grayscale (black areas in FIG. 2F) but blocked transmission elsewhere (gray areas in FIG. 2F). If such a digital filter scans another image and the intensity of the transmitted signal is plotted as a function of the relative shift between filter and image, maxima occur where the filter detects a matching structure in the image (ref. 38). FIG. 3 shows the result of scanning two synaptolucin images, FIGS. 2B and 2C, with a filter constructed from FIG. 2A. Clearly, the signal in FIG. 2B has no counterpart in the synaptic map, supporting its identification as a contaminant of non-neuronal origin (FIG. 3, bottom). The sites of evoked photon emissions in FIG. 2C, by contrast, produce a sharp maximum where filter and image are in register and thus map to nerve terminals (FIG. 3, top).

Figure 4A:
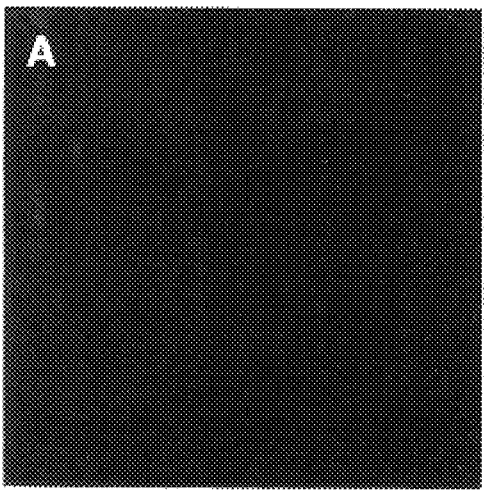
FIG. 4. Hippocampal neurons expressing synaptolucin-1, imaged by wide-field microscopy at the same intensifier and detector settings as in FIG. 2. (Top) Photon registrations from synaptolucin emissions during the first 30 sec after triggering exocytosis, colored in red and superimposed on synaptic maps obtained with FM 4-64. (Bottom) FM 4-64 images after a 30-sec hyperkalemic challenge. Panels 4A and 4B were recorded before and panels 4C and 4D after treatment with BoNTs B and F. BoNTs were applied during a 5-min depolarization (to enhance toxin uptake into recycling synaptic vesicles) and then during a 3-h incubation in complete medium with 1 $\mu$M tetrodotoxin. Note the marked decrease in FM 4-64 fluorescence intensity in panel 4B as opposed to panel 4D. Scale bar, 20 $\mu$m.
Figure 4C:
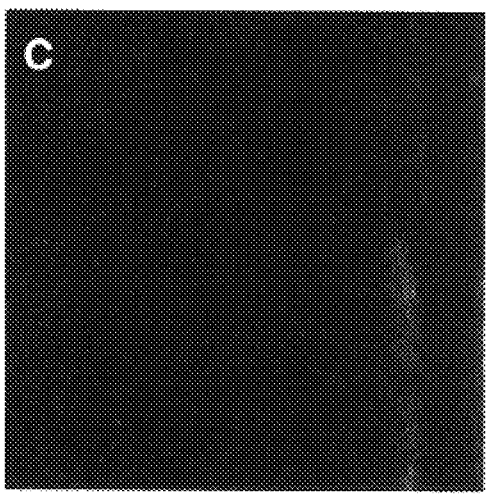
Figure 4B:
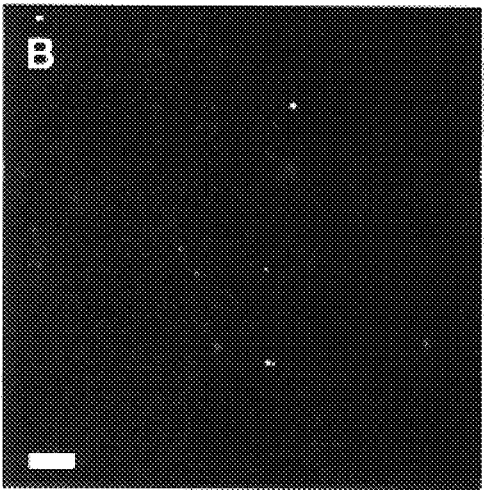
Figure 4D:
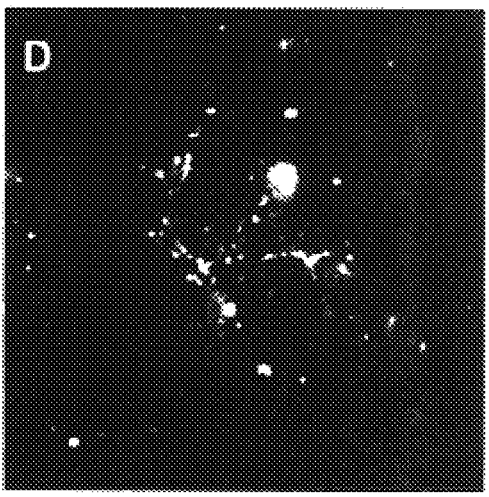

In addition to characteristic sensitivities to membrane potential and extracellular $Ca^{2+}$, an optical signal generated by synaptic vesicle exocytosis should be susceptible to clostridial neurotoxins that inactivate components of the machinery for transmitter release (39). FIG. 4 shows an experiment performed to address this point. An FM 4-64/ synaptolucin image pair was first acquired to locate synaptolucin-expressing synapses (FIG. 4A). Following a second round of FM 4-64 loading (to compensate for dye release during acquisition of the synaptolucin image, see FIG. 4B), the preparation was incubated on the microscope stage with 20 M each of botulinum neurotoxin (BOPM serotypes B and F (39) plus 1 $\mu$M tetrodotoxin to suppress action potentials (and hence, dye release) during the incubation. After 3 hours of toxin treatment a second pair of images was recorded, and noted to differ from the first in two respects: i) the dimming of FM 4-64 fluorescence that originally accompanied the hyperkalemic challenge now failed to occur, indicating that exocytosis was effectively blocked (compare FIG. 4B and 4D), and ii) photon emissions from synaptolucin disappeared concomitantly (compare FIGS. 4A and 4C). This ties the synaptolucin signal firmly to the process of neurotransmitter release.

Estimates for the number of quanta released under the experimental conditions described above and for the average observation time per synaptolucin can be derived by modelling vesicle release and recycling as Poisson processes (1,2,41,42). At a typical hippocampal synapse, the probability for exocytosis drops from an initial rate of about 20 quanta $sec^{-1}$ (the "readily releasable pool") to a basal rate of 2 quanta $sec^{-1}$ (43); the transition between initial and basal release rates occurs exponentially with a time constant of 1.2 sec (43). The probability of recycling is assumed constant throughout, with a $t_{1/2}$ of 20 sec (12,44). When such a synapse is observed for 30 sec under maintained hyperkalemic stimulation, an average of 67 quantal releases will take place, and the synaptolucins contained in one quantum (i.e., one vesicle) will emit for an average of 13 sec (see the legend to Table 1). Under the same conditions, an average of 12 photon registrations were counted per synapse (Table 1). Correcting for the detection efficiency (see Table 1), this translates into about 312 photon emissions for the entire synapse, 4.7 photon emissions for a single vesicle, and a photon emission rate of 0.38 $sec^{-1}$ per vesicle, equalling that generated by about three synaptolucin molecules in vitro at the same limiting luciferin concentration of 30 nM.

A fluctuation analysis (refs. 45, 46) of the photon counts in Table 1, obtained from the experiment shown in FIG. 2C, estimates the number of released quanta as 51 per synapse and the photon emission rate as 0.49 $sec^{-1}$ per vesicle, in rather close agreement with the values derived from kinetic arguments alone (Table 1).

TABLE 1

Photons and Vesicles

Photons

| | |
|---|---|
| Photon Counts per Field (Mean +/− SD) | 12 +/− 3.9 |
| Detection Efficiency | 0.13 |
| Collection Efficiency | 0.29 |
| Overall Efficiency | 0.04 |
| Photon Emissions per Field | 310 |

Vesicles

| Method of Estimation | Kinetics of Transmitter Release | Photon Count Fluctuations |
|---|---|---|
| Fusion Events | 67 | 51 |
| Photon Emissions per Vesicle | 4.7 | 6.1 |
| Photon Emission Rate per Vesicle ($sec^{-1}$) | 0.38 | 0.49 |

Photons.
The gray-level increment corresponding to a single photon count was determined from the histogram of FIG. 2C, and the number of photon registrations over a 30-sec period counted in 50 2 × 2-pixel fields, corresponding to 1.8 × 1.8 $\mu$m areas in the specimen plane.
These fields were selected by two criteria: i) FM 4–64 fluorescence in excess of the 97$^{th}$ percentile (see FIG. 2F), and ii) a >5-fold increase in synaptolucin activity upon depolarization.
To convert photon counts to photon emissions, two correction factors were used: the detection efficiency of the intensifier photocathode (C2400-30H; Hamamatsu Photonics) at 462 nm, and the collection efficiency of a 1.3 NA oil immersion objective, defined as the fraction of photon emissions from the focal plane that fall into the objective's acceptance cone.
Vesicles.
Synaptic vesicle exocytosis and recycling were modeled as Poisson processes (1,2,41,42), using kinetic parameters obtained in studies of transmitter or dye release from identified synapses of hippocampal neurons in culture (12,43,44). This stochastic model provided the basis for estimating the number of fusion events, either on the assumption of a fixed number of statistically independent release sites per synapse (41–43), or through an analysis of photon count fluctuations (45,46).

Comparing the number of photon registrations (about 12 per synapse) with the actual number of vesicle fusion events (about 60 per synapse) indicates that the majority of fusion events remained undetected with present technology. With a photon emission rate of 0.4–0.5 $sec^{-1}$ per vesicle and an overall photon detection efficiency of about 4% (Table 1), the time between two successive photon registrations from synaptolucins originating in the same vesicle (the waiting time for the stochastic process) would average about 50 sec. This is considerably longer than the average 13 sec for which a synaptolucin was observed. Hence under the conditions reported above, synaptolucins will often be re-internalized before a single photon emission can be detected, and those vesicle fusion events that do register cannot be precisely located on a temporal scale.

Example 2

SynaptopHluorins

To generate pH-sensitive GFP mutants, a combination of directed and random strategies was employed. In the folded conformation of GFP, the chromophore is located in the core of the protein, shielded from direct interactions with the environment by a tight beta-barrel structure. The remarkable stability of the fluorescent properties of wild-type protein under environmental perturbations, such as pH changes, is due to the protected position of the chromophore. To allow GFP to function as a pH sensor, a mechanism had therefore to be found by which changes in external proton concentration could be relayed to and affect the chromophore.

The exemplified approach to converting GFP to a pH sensor involves amino acid substitutions that couple changes in bulk pH to changes in the electrostatic environment of the chromophore. To obtain such substitutions, residues adjacent to 7 key positions were mutated. These key positions are known from X-ray crystallography (Ref. 48, 55, 58) to be part of the proton relay network of Tyr$^{66}$ (see FIG. 14A, 14B), and/or alter the excitation spectrum when mutated (Ref. 47, 48, 59, 60). Key residues fulfilling one or both of these criteria include Gln-69, Gln-94, Arg-96, Asn-121, His-148, Phe-165, Ile-167, Gln-183, Thr-203, Ser-205, and Glu-222.

In the examples below, reversible spectral changes that would be graded between pH 6 and 7 were sought (the pH in secretory vesicles (50, 51, 53) is in the range of 5–6, while the extracellular pH is generally 7.4), therefore the key residues themselves were not mutated, but rather the amino acids flanking them were altered. As in all beta-structures (GFP is an 11-stranded beta-barrel with a central alpha-helix carrying the chromophore (55, 48, 58), FIG. 14A), the side chains of adjacent residues alternate in orientation, such that those of amino acids flanking key positions (whose side chains point towards the chromophore, FIG. 14B) face the surface of the protein and should thus be likely to titrate with bulk pH. Because histidine possesses the desired $pK_a$ (ca. 6.4) for a sensor for exocytosis, histidine residues were introduced at positions 149, 151, 153, 164, 166, 168, 202, 204, and 206, singly or in combination. Changes in the charge of a critically located, outward-facing imidazole ring were expected to drive a spectral shift as a function of pH.

To this end, the coding region of GFP clone 10 (Ref. 47) was amplified by PCR, using the appropriate mutagenic oligonucleotides, ligated to the expression vector pGEMEX2, and transformed into *E.coli* strain BL-21. Visibly fluorescent colonies were selected, and high-level expression of GFP achieved by growing the clones to saturation in liquid culture, at 25° C. and without IPTG induction. To prepare soluble extracts, cells from 2-ml cultures were collected, washed, and resuspended in 50 mM Tris/HCl, pH 8.0, containing 2 mM EDTA, 0.2 mg/ml lysozyme, and 20 μg/ml DNase I. After 2 hours on ice, lysates were clarified by centrifugation at 14,000 rpm for 15 min. Excitation spectra of lysates, diluted tenfold into 50 mM sodium cacodylate buffer, adjusted to pH 7.4 or 5.5 and containing 100 mM KCl, 1 mM $MgCl_2$, and 1 mM $CaCl_2$, were recorded in a Perkin-Elmer LS 50B spectrofluorimeter at room temperature. The emission wavelength was set to 510 nm and the excitation wavelength scanned from 360 to 500 nm, using 7.5-nm bandwidths for excitation and emission.

Figure 8B:
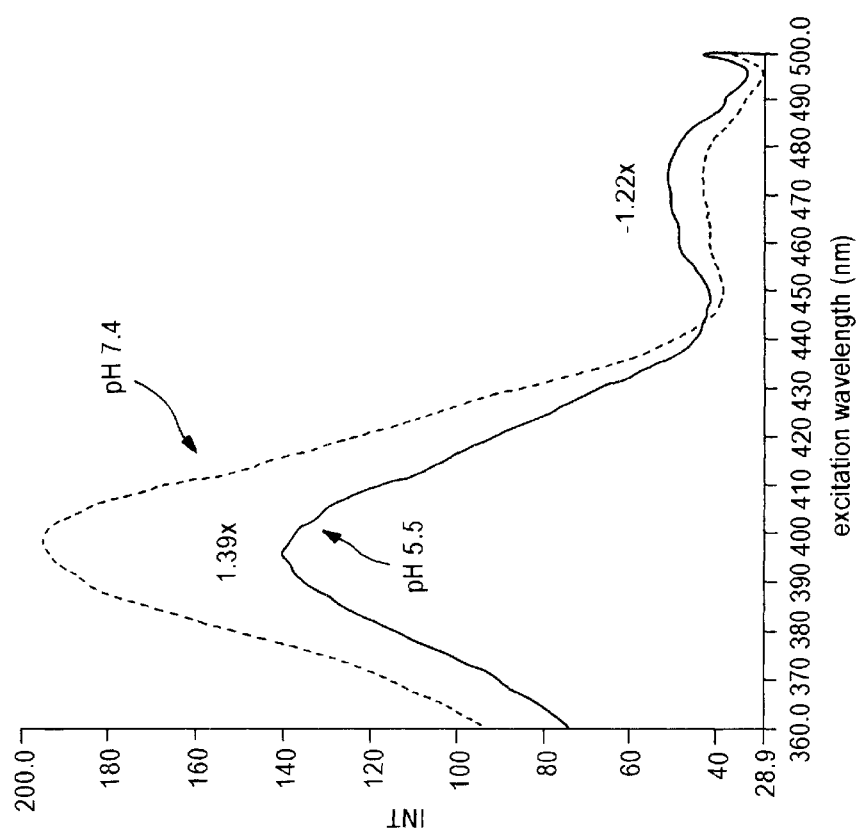
Figure 8A:
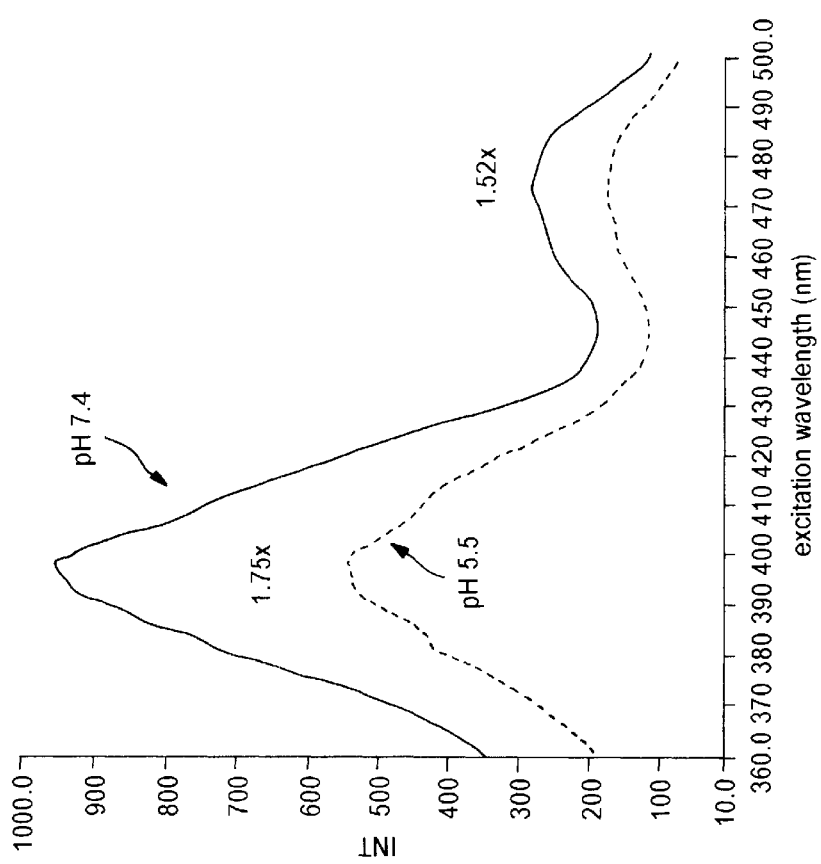
Figures 9A, 9B:
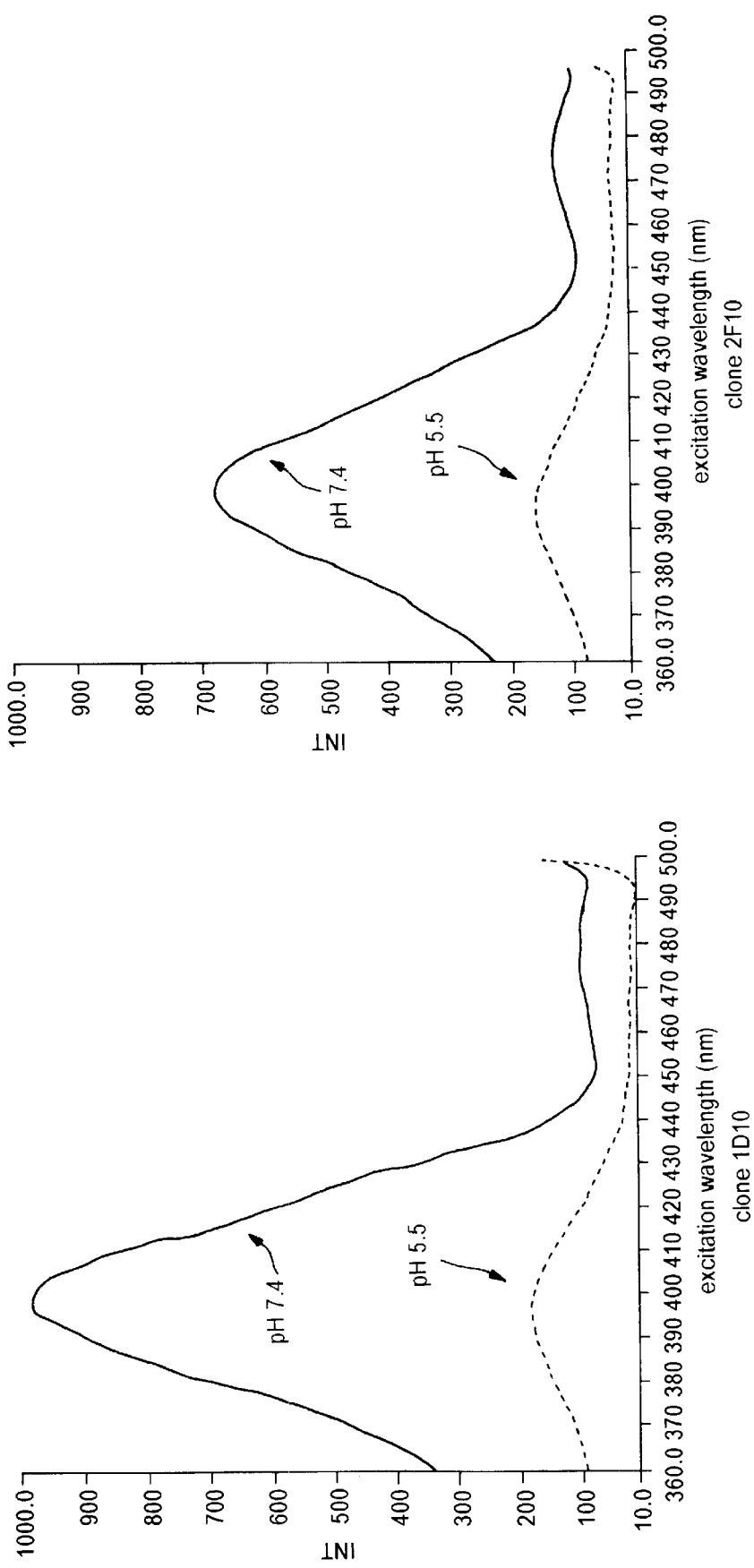
Figures 9E, 9F:
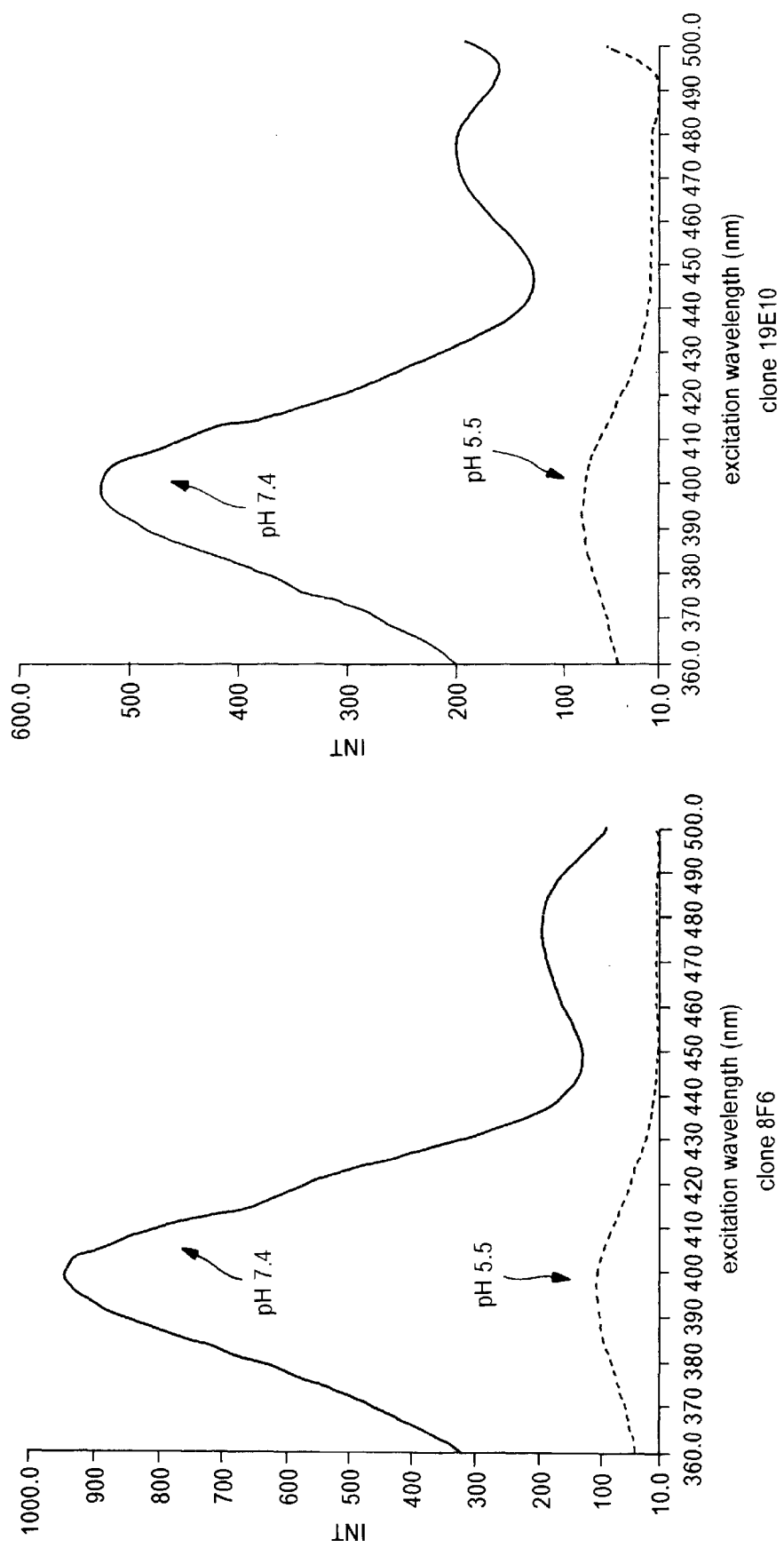
Figures 10C, 10D:
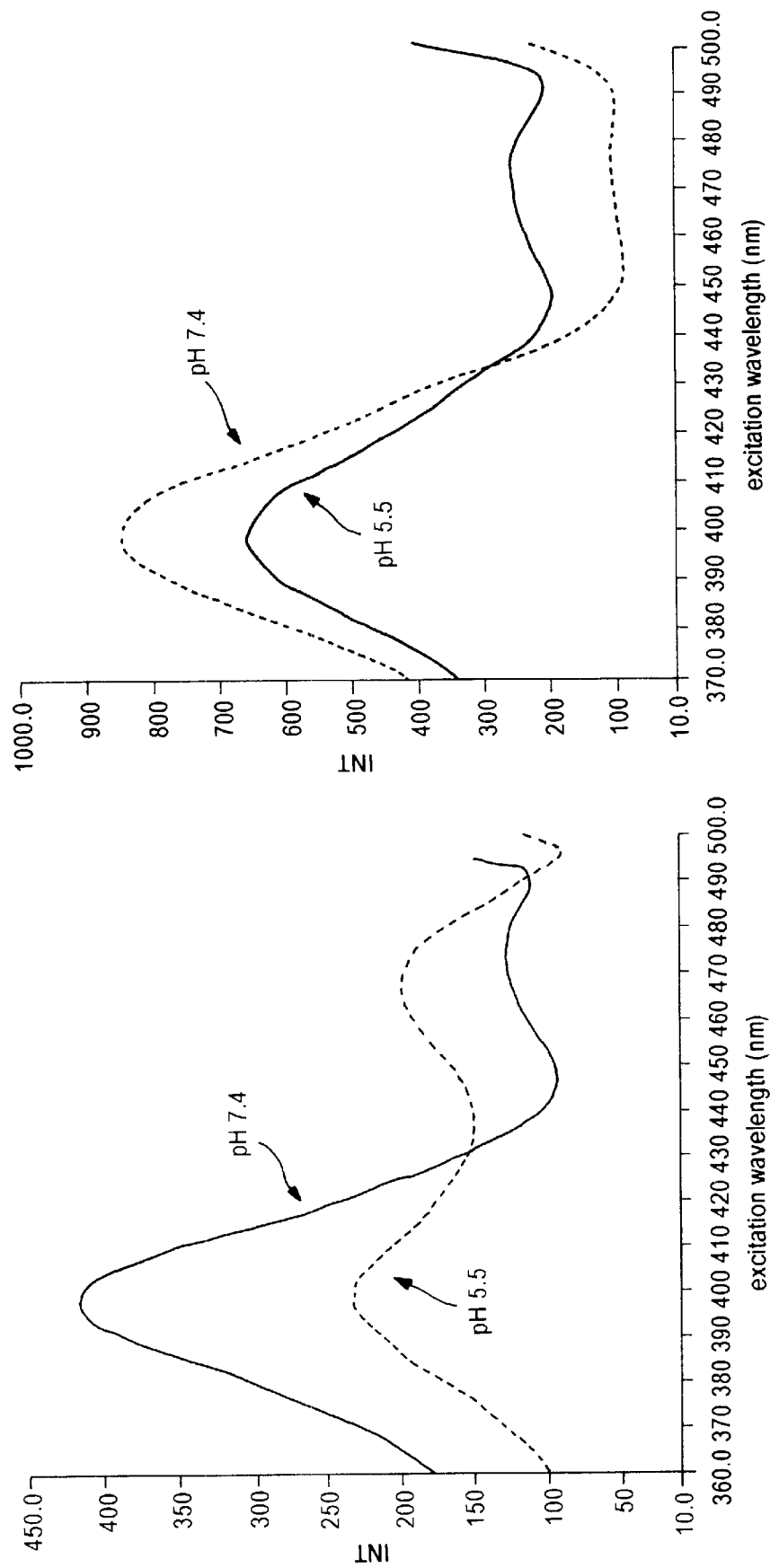
Figure 10G:
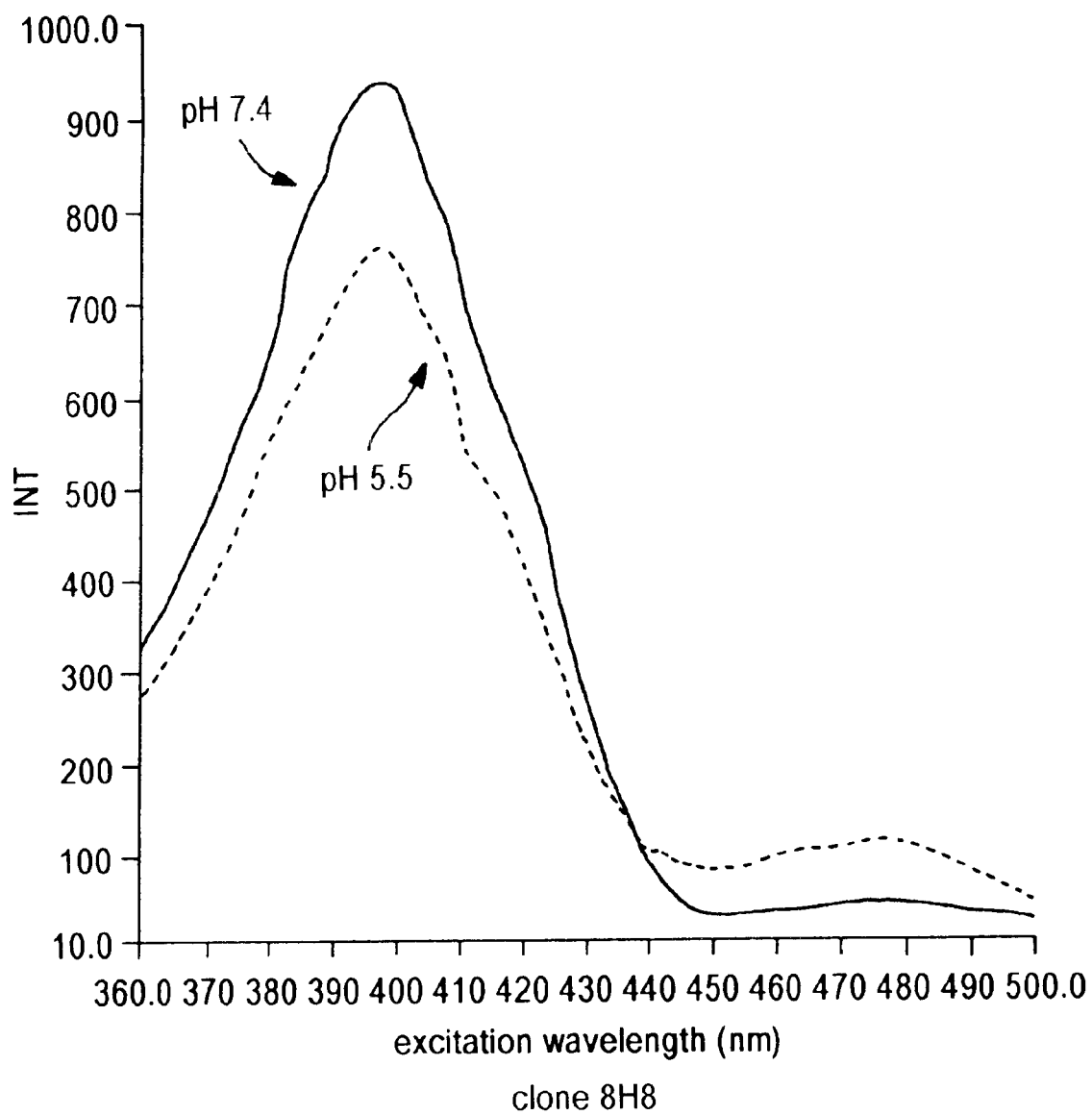

One of the candidate mutants generated in this first round of mutagenesis, S202H, showed a 16% reduction in 395-nm excitation and a 26% increase in 475-nm excitation, induced by a pH shift from 7.4 to 6.0 (compare FIG. 8A and 8B). Clone S202H was subjected to further rounds of mutagenesis in an effort to increase pH-responsiveness. Using degenerate oligonucleotides to incorporate more than one amino acid residue at each position, and to mutate more than one position simultaneously, cDNA regions including the key amino acid residues identified above, i.e., codons for amino acid positions 94–97, 147–150, 164–168, 202–204, and 221–223, were initially targeted for mutagenesis. In later mutagenesis experiments, codons for amino acid positions 94–97, 146–149, 164–168, 202–205, and 221–225, were mutated. The resulting libraries encompassed between 32 and 3,072 different nucleotide sequences in the initial experiments, and between 20 and 8,000 different sequences in the later experiments. The PCR libraries were ligated to pGEMEX2, transformed into strain BL-21, and visibly fluorescent colonies selected. For high-throughput screening, liquid cultures were grown and lysates prepared and analyzed in 96-well microtiter plates. For each well, fluorescence emitted at 510 nm after excitation at 400 and 460 nm was recorded at three pH values in a Labsystems Fluoroskan II fluorescent plate reader: first at pH 8.0 (lysis buffer), then after addition of 200 mM sodium cacodylate to reduce the pH to 5.5, and finally after addition of 200 mM NaOH to revert the pH to 7.4. Fluorescence data were digitized, corrected for volume changes due to buffer and NaOH additions, and analyzed for changes in excitation peak ratios. Promising candidates were re-analyzed in detail, to obtain full excitation spectra and complete DNA sequences.

Including the later experiments, approximately 19,000 colonies were screened altogether. After two rounds of mutagenesis, the process generated two distinct classes of pHluorins, which are referred to as "ratiometric" and "ecliptic" for the reasons discussed. These two classes were separately subjected to three and five additional combinatorial rounds, respectively, followed by one random round, of mutagenesis. Finally, the two amino acid changes (V163A, S175G) known to improve folding at 37° C. (ref.49) were introduced; these changes did not affect the pHluorins' spectral properties but did increase expression levels at 37° C. The sequences and spectra of two prototypes, termed 1B11t and 14E12t, are shown in FIG. 8C and 8D and 22–23. Clone 1B11t (See FIG. 22 for the amino acid sequence and 7A for the cDNA nucleic acid sequence) responded to a reduction in pH with a complete (and reversible) loss of fluorescence excitable at 475 nm, and an about 8-fold reduction in fluorescence intensity excitable at 395 nm (FIG. 8C). This type of mutant, which is referred to as an "ecliptic" pHluorin for reasons discussed below, provides a preferred light-generating module for the synaptopHluorins disclosed below. Clone 14E12t (see FIG. 23 for the amino acid sequence and FIG. 7B for the cDNA nucleic acid sequence) responded to a reduction in pH with decreased fluorescence excitable at 395 nm, and increased fluorescence excitable at 475 nm (FIG. 8D). The class of "ratiometric" pHluorins exemplified by clones 14E12 and 14E12t provides another preferred light-generating module for synaptopHluorins.

The amino acid substitutions of the other clones are identified in Table 2. Excitation spectra for the 1B11-like GFP mutants are shown in FIGS. 9A–9D. Excitation spectra for the 14E12-like mutants is shown in FIGS. 10A–10G. Corresponding cDNA nucleic acid sequences for these mutants are shown in FIGS. 11 and 12 respectively. The most preferred ecliptic pHluorin is 8F3, and the most preferred ratiometric pHluorin is C6.

Although a limited number of mutations, in a limited number of regions of the GFP protein are exemplified herein, it is anticipated that mutations to other portions of the GFP protein may be made by the methods disclosed herein.

TABLE 2

| Mutant | Amino Acid Substitutions | | | | | | | |
|---|---|---|---|---|---|---|---|---|
| Amino Acid Substitutions in Ecliptic pHluorins | | | | | | | | |
| 1D10 | S147D | | T161I | | | | S202H | |
| 2F10 | S147D | N149H | T161I | | | | S202H | |
| 2H2 | S147D | N149V | T161I | | | | S202H | |
| 1B11 | S147D | N149Q | T161I | | | | S202H | |
| 1B11t | S147D | N149Q | T161I | V163A | | S175G | S202H | |
| 8F3 | S147D | N149Q | T161I | V163A | | S175G | S202F | Q204T A206T |

TABLE 2-continued

| Mutant | Amino Acid Substitutions | | | | | | | | |
|---|---|---|---|---|---|---|---|---|---|
| 8F6 | S147D | N149T | T161I | | | | | | S202H |
| 19E10 | S147D | N149L | | | K166Q | I167V | R168H | | S202H |
| Amino Acid Substitutions in Ratiometric pHluorins | | | | | | | | | |
| 14E12 | S147D | N149D | | | K166Q | I167V | | | S202H |
| 14E12t | S147D | N149D | | V163A | K166Q | I167V | | S175G | S202H |
| 14C9 | S147D | N149L | | | K166Q | I167V | | | S202H |
| 14C8* | S147P | N149Y | | | K166Q | I167V | R168H | | S202H |
| 2G3 | S147E | N149L | | V163A | | | R168H | S175G | S202H |
| C6** | S147E | N149L | | V163A | K166Q | I167V | R168H | S175G | S202H |
| S202H | | | T161I | | | | | | S202H |
| 14D9 | S147P | N149W | | | K166Q | I167V | R168H | | S202H |
| 8H8 | S147P | N149W | T161I | | | I167C | | | S202H |

*Mutant 14C8 also incorporates G2S.
*Mutant C6 also incorporates E132D, N164I, R168H, and L236V mutations.

Ratiometric pHluorins display a continuous and reversible excitation ratio change between pH 7.5 and 5.5 (FIG. 14D), with a response time of <200 msec. Ecliptic pHluorins, by contrast, gradually lose fluorescence intensity as pH is lowered, until at pH values of 6.0 and, the excitation peak at 475 nm vanishes entirely (FIG. 14E). In an environment of pH<6.0, the protein is therefore invisible (eclipsed) under 475-nm excitation; however, it can still be seen (weakly) at 395 nm. These changes are entirely reversible within <200 msec after returning to neutral pH.

For initial imaging experiments, ratiometric pHluorins were either 1) glycosylphosphatidylinositol (GPI)-anchored (61) at the cell surface (FIG. 15B),
2) inserted into the lumenal domain of TGN38 (62), an integral membrane protein of the trans-Golgi network (TGN) (FIG. 15C), or
3) attached to the lumenally exposed C-terminus of cellubrevin (63), a membrane protein of the endosomal system (FIG. 15D).

Correct targeting of these constructs was confirmed
1) by the release of cell-bound fluorescence after GPI-anchor cleavage (61) with phosphatidylinositol-specific phospholipase C,
2) by co-localization with myc-tagged TGN38, or
3) by co-localization with internalized transferrin.

In all instances, the labelled subcellular compartment of transfected HeLa cells was readily seen by wide-field fluorescence microscopy and characterized by a distinct 410/470-nm excitation ratio, $R_{410/470}$ (FIG. 15). (The optimal excitation wavelengths for imaging were found to be 410 and 470 nm rather than 395 and 475 nm. This probably reflects the different optical trains of microscope and spectrofluorimeter as well as the different fluorescence backgrounds in vivo and in vitro. Exposure times ranged from 50 to 200 msec per excitation wavelength, and $R_{410/470}$ was sampled at up to 5 Hz.) The ratio remained stable within ±3% during 2 minutes of continuous image acquisition at 1 Hz, indicating that the pHluorin did not photoisomerize (55) detectably at the light intensities used.

To convert excitation ratios to pH values in this and other experiments, a standard curve was generated by imaging, in buffers of defined pH, cells expressing GPI-anchored pHluorin at their surface. Based on this standard curve (FIG. 15A), pH values (mean±SD) of 5.51±0.66 for endosomes (n=61) and 6.21±0.39 for the TGN (n=28) were determined, consistent with previous estimates of 5.0–5.5 and ca. 6.2, respectively.

Vacuolar $(H^+)$-ATPases maintain the interior of synaptic vesicles at higher proton electrochemical potential than the cytoplasm, establishing an electrochemical gradient across the vesicle membrane that is tapped to concentrate neurotransmitter (51–53, 65). Whether this gradient is mainly electrical or chemical (i.e., a pH gradient) is determined by the vesicle membrane's anion conductances. The magnitudes of these conductances, as well as the relative magnitudes of electrical and chemical potential in vivo, are unknown; reported estimates of intravesicular pH concern purified synaptic vesicles in vitro (51–53). To perform a measurement in vivo, hippocampal neurons in low-density culture (66) were infected with a herpes simplex virus (HSV) amplicon vector (67, 68) expressing a synaptopHluorin (69) in which the targeting module is the synaptic vesicle v-SNARE VAMP-2/synaptobrevin (65) and the light-emitting unit is the ratiometric pHluorin, joined to VAMP at its lumenally exposed C-terminus. SynaptopHluorin fluorescence appeared in the beads-on-a-string pattern typically seen when a single axon forms multiple synapses with a single dendrite (FIG. 15E) and reported an intravesicular pH (mean±SD) of 5.67±0.71 (n=84).

Fusion of an acidified synaptic vesicle with the presynaptic membrane will establish continuity of its interior with the extracellular fluid, causing an essentially instantaneous rise of pH from ca. 5.7 to ca. 7.4. A synaptopHluorin, attached to the inner surface of the vesicle membrane, will experience the change in pH and respond with a recordable change of its excitation spectrum, which thus can serve as an index of synaptic activity. FIG. 16 illustrates this principle. FIG. 16A shows a field of neurites forming abundant synaptic contacts, revealed by immunostaining for the synaptic vesicle protein synaptotagmin-I (65). Some of these contacts were made by neurons expressing the ratiometric synaptopHluorin; they were easily distinguished by their green fluorescence (compare the set of all synapses visible in FIG. 16A with the subset of genetically tagged synapses visible in FIG. 16B).

The application of depolarizing solution containing 90 mM KCl elicited a prompt increase in $R_{410/470}$ that could be recorded from many boutons in parallel (FIG. 16C). The response depended on external $Ca^{2+}$ and peaked at 8–20% of the signal that would have resulted from simultaneous fusion of all of the vesicles in the bouton. The latter was estimated by neutralizing the pH in all synaptic vesicles with 50 mM $NH_4Cl$, which releases $NH_3$ that diffuses across cellular membranes and quenches free protons in acidified organelles (FIG. 16C). Relative to the maximum possible response, the increase in $R_{410/470}$ due to $K^+$-depolarization thus reflects a rapid rise in pH experienced by 8–20% of the vesicles at a synapse—a number that closely matches the size of the "readily releasable" pool (65, 70). This pool encompasses one to two dozen (70) of the 100–200 synaptic vesicles at an active zone (65) (i.e., 6–24%) and is released within the first two seconds after the onset of a depolarizing stimulus (70).

$R_{410/470}$ remained elevated during continued depolarization, indicating that a steady state was attained in which continued exocytosis was balanced by vesicle recycling, leaving a constant fraction of vesicle membrane protein externally disposed (FIG. 16C). After the depolarizing stimulus was withdrawn, $R_{410/470}$ gradually returned to baseline (FIG. 16C). Vesicle membrane protein is known to be re-internalized by endocytosis to regenerate synaptic vesicles (with a $t_{1/2}$ of 10–20 seconds (71), in keeping with the time course observed in FIG. 16C), and synaptopHluorin is expected to return to its spectral baseline as the vesicle acidifies.

The $R_{410/470}$ value, whether it pertains to a single synapse or a population of many synapses in a region, therefore provides a running average of synaptic activity during the previous several seconds. Like all ratiometric indices, $R_{410/470}$ is insensitive to variations in optical path length, pHluorin concentration, and illumination intensity. These properties would make the ratiometric pHluorin an excellent probe for analyses of complex neural systems, when a large number of synapses has to be surveyed in three dimensions and sampled serially to achieve spatial resolution.

Ecliptic pHluorins, because they are non-fluorescent at pH<6 under 470-nm excitation (FIG. 14E), eliminate fluorescence due to the large excess of resting vesicles and are thus potentially suited for detecting single vesicle fusion events. To test this, the mast cell line RBL-2H3, which releases histamine, serotonin, and other mediators when exocytosis is triggered (72), was chosen. When expressed in RBL-2H3 cells, ecliptic synaptopHluorin (a fusion protein of VAMP and the ecliptic pHluorin) was localized to scattered fluorescent puncta which were assumed to be secretory vesicles, and which under resting conditions were seen only with 410-nm and not with 470-nm excitation (FIG. 17A, frame 1). The pH in these granules, measured with the ratiometric pHluorin, averaged (mean±SD) 5.20±0.55 (n=29), the threshold for 470-nm excitation of ecliptic pHluorin.

After initiating a secretory response by cross-linking surface-receptor-bound IgE with an anti-IgE antibody (72), granule content was released into the medium (FIG. 17B), and changes in fluorescence excited at 470 nm occurred in locations harboring granules (FIG. 17A, frames 1–7). Individual spots of variable integrated intensity (the product of spot size and fluorescence intensity, FIG. 17C) appeared suddenly, at various times after the stimulus to secrete (FIG. 17A, frames 2–7). The cumulative fluorescence of these individual events closely followed the appearance of granule content in the medium (FIG. 17B), as expected if each event were due to fusion of a single granule (73), or of multiple granules undergoing compound exocytosis (73,74). In that case, the more intense events in FIG. 17C would correspond to compound exocytoses.

Occasionally, fluorescent spots disappeared, indicating granule retrieval and re-acidification (follow the cluster marked by the arrow in frame 4 through frames 5 and 6). Within the time frame of these experiments (FIG. 17B), these "off" events (73) were less frequent than the "on" events of exocytosis, consistent with the slow resolution of the often tortuous membrane topology created at exocytosis sites (74). Rarely, a granule appeared, disappeared, and reappeared in what seemed to be the same location (arrows in frames 5–7). This could correspond to the phenomenon of "flicker" (73), in which transient opening and closing of a fusion pore would cause the vesicle's internal pH (and thus, the ecliptic pHluorin's emission intensity) to fluctuate.

Mutagenesis. Wild-type *A. victoria* gfp cDNA (pGFP-1; Clontech) was subjected to PCR mutagenesis. Directed codon changes were introduced with non-degenerate primers and Pwo polymerase; combinatorial steps employed primer libraries of 32- to 32,768-fold nucleotide degeneracy and Taq polymerase; random steps used low-fidelity amplification with Taq polymerase (7 mM $MgCl_2$, 0.5 mM $MnCl_2$, and a 5-fold excess of dCTP and dTTP over dGTP and dATP). PCR products were ligated to pGEMEX-2 (Promega), transformed into *E. coli*, and visibly fluorescent colonies were expanded for analysis. Clones were grown (at 25° C.; without IPTG induction), lysed (on ice; in 50 mM Tris, pH 8.0, 2 mM EDTA, 0.2 mg/ml lysozyme, 200 U/ml DNase I), and analyzed in 96-well plates. Three successive readings of fluorescence emitted at 510 nm were obtained in a Labsystems Fluoroskan II plate reader equipped with 400- and 460-nm excitation filters: the first at pH 8.0, the second after addition of acid to reduce the pH to 6.0, and the third after addition of base to revert to pH 7.4. The plasmid encoding the mutant with the largest reversible, pH-dependent change in $R_{410/460}$ served as the PCR template in the next round of mutagenesis.

cDNAs encoding ratiometric and ecliptic pHluorins were sequenced and expressed in pGEX-2T (Pharmacia). Fluorescence spectra were recorded on pure recombinant protein, obtained after thrombin cleavage of the respective GST fusion protein, in a Perkin-Elmer LS-50B spectrofluorimeter. Response times to pH changes were estimated in time drive mode, in a stirred cuvette that contained the pHluorin plus SNAFL-2 (Molecular Probes) as an internal standard.

Cells. GFP modules were linked to targeting modules via two -Ser-Gly-Gly-repeats and one -Thr-Gly-Gly- repeat; the latter contained a unique Age I site for insertion of GFP sequences. The insertion sites were placed between signals for ER translocation and GPI-anchor addition (derived from preprolactin and decay accelerating factor (61), respectively), at the mature N-terminus of TGN38 (ref. 15), and at the very C-termini of VAMP (65) and cellubrevin (63). All constructs carried a single, lumenally exposed GFP module.

The vector pCI (Promega) was used to drive transient expression in HeLa and RBL-2H3 cells. Hippocampal neurons were infected with purified virions of the quadruply deleted HSV strain (67) THZ.3 ($\alpha 4^-$, $\alpha 22^-$, $\alpha 27^-$, $U_L 41^-$). Amplicon plasmids based on the pα4"a" backbone (68) were packaged with the help of the complementing cell line (67) 7B, and the resulting mixture of vector and helper virions pelleted through 25% sucrose. Neural cultures were prepared as described (69), except that hippocampi were collected from embryonic (E19) rats, horse serum was used, and 10 mM cytosine arabinoside was added from day 3 after plating. Experiments were performed after 17–29 days in vitro.

Microscopy. Two days after transfection or viral infection, cells were transferred to imaging buffer (25 mM Na-Hepes, pH 7.4, 119 mM NaCl, 2.5 mM KCl, 2 mM $CaCl_2$, 2 mM $MgCl_2$, 30 mM glucose) and at 37° C. imaged on a Zeiss Axiovert microscope equipped with a 40×, 1.3 NA PLAN-NEOFLUAR objective and 1.6× and 2.5×OPTOVAR inserts. Experiments were controlled through METAFLUOR 3.0 (Universal Imaging), with off-line background subtraction and image analysis, using META-MORPH 3.0 (Universal Imaging) and MATHEMATICA 3.0 (Wolfram Research). To rapidly alternate between narrow excitation bands, a POLYCHROME II grating monochromator (Till Photonics; 75 W xenon lamp, 12-nm bandwidth) was coupled into the epi-illumination port of the microscope. Emitted light was passed through a dichromatic mirror (500DCXR) and a bandpass filter (HQ535/50, both from Chroma Technologies) and collected on a PENTAMAX-512EFT frame-transfer camera with fiber coupled GEN IV image intensifier (Princeton Instruments; cooled 12-bit EEV-37 CCD array).

While we have described herein a number of embodiments of the invention, it is apparent that the basic constructions can be altered to provide other embodiments which utilize the methods of this invention. Therefore, it will be appreciated that the scope of this invention is defined by the claims appended hereto rather than by the specific embodiments which have been presented hereinbefore by way of example.

REFERENCES

The following publications are incorporated herein by reference in their entirety:
1. Redman, S. (1990) *Physiol. Rev.* 70:165–198.
2. Stevens, C. F. & Wang, Y. (1995) *Neuron* 14:795–802.
3. Anderson, J. A. & Rosenfeld, E., eds. (1988) *Neurocomputing* (NUT Press, Cambridge).
4. Shepherd, G. M., ed. (1990) *The Synaptic Organization of the Brain* (Oxford University Press, Oxford), 3rd Ed.
5. McKenna, T., Davis, J. & Zornetzer, S. E., eds. (1992) *Single Neuron Computation* (Academic Press, Boston).
6. Meister, M., Pine, J. & Baylor D. A. (1994) *J. Neurosci. Meth.* 51:95–106.
7. Stenger, D. A. & McKenna, T. M., eds. (1994) *Enabling Technologies for Cultured Neural Networks* (Academic Press, San Diego).
8. Grinvald, A. (1985) *Annu. Rev. Neurosci.* 8:263–305.
9. Tsien, R. Y. (1989) *Annu. Rev. Neurosci.* 12:227–253.
10. Tsien, R. Y. & Waggoner, A. (1995) in *Handbook of Biological Confocal Microscopy*, ed. Pawley, J. B. (Plenum, New York), 2nd Ed., pp. 267–279.
11. Betz, W. J. & Bewick, G. S. (1992) *Science* 255:200–203.
12. Ryan, T. A., Reuter, H., Wendland, B., Schweizer, F., Tsien, R. W. & Smith, S. J. (1993) *Neuron* 11:713–724.
13. Meister, M. (1996) *Proc. Natl. Acad. Sci. USA* 93:609–614.
14. Katz, L. C. & Shatz, C. J. (1996) *Science* 274:1133–1138.
15. Kuypers, H. G. J. M. & Ugolini, G. (1990) *Trends Neurosci.* 13:71–75.
16. Thompson, E. M., Nagata, S. & Tsuji, F. I. (1989) *Proc. Natl. Acad. Sci. USA* 86:6567–6571.
17. Ho, D. Y. (1994) *Methods Cell Biol.* 43:191–210.
18. Lawrence, M. S., Ho, D. Y., Dash, R. & Sapolsky, R. M. (1995) *Proc. Natl. Acad. Sci. USA* 92:7247–7251.
19. Perin, M. S., Fried, V. A., Mignery, G. A., Jahn, R. & Suldhof, T. C. (1990) *Nature* 345:260–263.
20. Elferink, L. A., Trimble, W. S. & Scheller, R. H. (1989) *J. Biol. Chem.* 264:11061–11064.
21. Sudhof, T. C., Baumert, M., Perin, M. S. & Jahn, R. (1989) *Neuron* 2:1475–1481.
22. DeLuca, N. A., McCarthy, A. M. & Schaffer, P. A. (1984) *J. Virol.* 56:558–5570.
23. Matthew, W. D., Tsavaler, L. & Reichardt, L. F. (1981) *J. Cell Biol.* 91:257–269.
24. Edelmann, L., Hanson, P. I., Chapman, E. R. & Jahn, R. (1995) *EMBO J.* 14:224–231.
25. Clift-O'Grady, L., Linstedt, A. D., Lowe, A. W., Grote, E. & Kelly, R. B. (1990) *J. Cell Biol.* 110:1693–1703.
26. Hastings, J. W. & Weber, G. (1963) *J. Opt. Soc. Am.* 53:1410–1415.
27. Huettner, W. J. & Baughman, R. W. (1986) *J. Neurosci.* 6:3044–3060.
28. Geppert, M., Goda, Y., Hammer, R. E., Li, C., Rosahl, T. W., Stevens, C. F. & Sudhof, T. C. (1994) *Cell* 79:717–727.
29. Johnson, F. H. & Shimomura, O. (1978) *Methods Enzymol.* 57:331–364.
30. Shimomura, O., Johnson, F. H. & Saiga, Y. (1961) *J. Cell. Comp. Physiol.* 58:113–124.
31. Inouye, S., Ohmiya, Y., Toya, Y. & Tsuji, F. J. (1992) *Proc. Natl. Acad. Sci. USA* 89:9584–9587.
32. Kishi, Y., Goto, T., Hirata, Y., Shimomura, O. & Johnson, F. H. (1966) *Tetrahedron Lett.* 29:3427–3436.
33. Shimomura, O., Johnson, F. H. & Masugi, T. (1969) *Science* 164:1299–1300.
34. Shimomura, O. & Johnson, F. H. (1970) *Photochem. Photobiol.* 12:291–295.
35. Wulff, K. (1981) in *Bioluminescence and Chemiluminescence*, DeLuca, M. A. & McElroy, W. D., eds. (Academic Press, New York), p. 219.
36. Henkel, A. W. & Betz, W. J. (1995) *J. Neurosci.* 15:8246–8258.
37. Feany, M. B., Yee, A. G., Delvy M. L. & Buckley, K. M. (1993) *J. Cell Biol.* 123:575–584.
38. Duda, R. O. & Hart, P. E. (1973) *Pattern Classification and Scene Analysis* (John Wiley & Sons, New York).
39. Montecucco, C. & Schiavo, G. (1995) *Q. Rev. Biophys.* 28:423–472.
40. Bliss, T. V. P. & Collingridge, G. L. (1993) *Nature* 361:31–39.
41. Katz, B. (1969) *The Release of Neural Transmitter Substances* (Liverpool University Press, Liverpool).
42. Bekkers, J. M. & Stevens, C. F. (1995) *J. Neurophysiol.* 73:1145–1156.
43. Stevens, C. F. & Tsujimoto, T. (1995) *Proc. Natl. Acad. Sci. USA* 92:846–849.
44. Ryan, T. A., Smith, S. J. & Reuter, H. (1996) *Proc. Natl. Acad. Sci. USA* 93:5567–5571.
45. Katz, B. & Miledi, R. (1972) *J. Physiol.* 224:665–699.
46. Neher, E. & Stevens, C. F. (1977) *Annu. Rev. Biophys. Bioeng.* 6:345–381.
47. Heim, R., Prasher, D. C., Tsien, R. Y. (1994) *Proc. Natl. Acad. Sci. USA* 91:12501–12504.
48. Ormö, M., Cubitt, A. B., Kalio, K., Gross, L. A., Tsien, R. Y., Remington, S. J. (1996) Science 273: 1392–1395.
49. Siemering, K. R., Golbik, R., Sever, R., Haseloff, J. (1996) Curr. Biol. 6:1653–1663.
50. Anderson, R. G. & Orci, L. A view of acidic intracellular compartments. *J Cell Biol* 106, 539–43 (1988).
51. Füldner, H. H. & Stadler, H. $^{31}$P-NMR analysis of synaptic vesicles: status of ATP and internal pH. *Eur J Biochem* 121, 519–24 (1982).
52. Maycox, P. R., Hell, J. W. & Jahn, R. Amino acid neurotransmission: spotlight on synaptic vesicles. *Trends Neurosci* 13, 83–7 (1990).
53. Tabb, J. S., Kish, P. E., Van Dyke, R. & Ueda, T. Glutamate transport into synaptic vesicles. Roles of membrane potential, pH gradient, and intravesicular pH. *J Biol Chem* 267, 15412–8 (1992).
54. Ward, W. W. in *Bioluminescence and chemiluminescence*. (eds. DeLuca, M. A. & McElroy, W. D.) 235–42 (Academic Press, New York, 1981).

55. Brejc, K., et al. Structural basis for dual excitation and photoisomerization of the Aequorea victoria green fluorescent protein. *Proc Natl Acad Sci USA* 94, 2306–11 (1997).
56. Chattoraj, M., King, B. A., Bublitz, G. U. & Boxer, S. Ultra-fast excited state dynamics in green fluorescent protein: Multiple states and proton transfer. *Proc Natl Acad Sci USA* 93, 8362–8367 (1996).
57. Heim, R., Prasher, D. C. & Tsien, R. Y. Wavelength mutations and posttranslational autoxidation of green fluorescent protein. *Proc Natl Acad Sci USA* 91, 12501–4 (1994).
58. Yang, F., Moss, L. G. & Phillips, G. N., Jr. The molecular structure of green fluorescent protein. *Nature Biotech.* 14, 1246–1251 (1996).
59. Ehrig, T., O'Kane, D. J. & Prendergast, F. G. Green-fluorescent protein mutants with altered fluorescence excitation spectra. *FEBS Lett* 367, 163–6 (1995).
60. Heim, R. & Tsien, R. Y. Engineering green fluorescent protein for improved brightness, longer wavelengths and fluorescence resonance energy transfer. *Curr Biol* 6, 178–82 (1996).
61. Caras, I. W., Weddell, G. N., Davitz, M. A., Nussenzweig, V. & Martin, D. W., Jr. Signal for attachment of a phospholipid membrane anchor in decay accelerating factor. *Science* 238, 1280–3 (1987).
62. Luzio, J. P., et al. Identification, sequencing and expression of an integral membrane protein of the trans-Golgi network (TGN38). *Biochem J* 270, 97–102 (1990).
63. McMahon, H. T., et al. Cellubrevin is a ubiqitous tetanus-toxin substrate homologous to a putative synaptic vesicle fusion protein. *Nature* 364, 346–49 (1993).
64. Seksek, O., Biwersi, J. & Verkman, A. S. Direct measurement of trans-Golgi pH in living cells and regulation by second messengers. *J. Biol. Chem.* 270, 4967–70 (1995).
65. Sudhof, T. C. The synaptic vesicle cycle: a cascade of protein-protein interactions. *Nature* 375, 645–53 (1995).
66. Goslin, K. & Banker, G. in *Culturing nerve cells* (eds. Banker, G. & Goslin, K.) 251–81 (NET Press, Cambridge, 1991).
67. Marconi, P., et al. Replication-defective herpes simplex virus vectors for gene transfer in vivo. *Proc Natl Acad Sci USA* 93, 11319–20 (1996).
68. Lawrence, M. S., Ho, D. Y., Dash, R. & Sapolsky, R. M. Herpes simplex virus vectors overexpressing the glucose transporter gene protect against seizure-induced neuron loss. *Proc Natl Acad Sci USA* 92, 7247–51 (1995).
69. Miesenbock, G. & Rothman, J. E. Patterns of synaptic activity in neural networks recorded by light emission from synaptolucins. *Proc. Natl. Acad. Sci. USA* 94, 3402–3407 (1997).
70. Stevens, C. F. & Tsujimoto, T. Estimates for the pool size of releasable quanta at a single central synapse and for the time required to refill the pool. *Proc Natl Acad Sci USA* 92, 846–9 (1995).
71. Ryan, T. A. Endocytosis at nerve terminals: timing is everything. *Neuron* 17, 1035–7 (1996).
72. Roa, M., Paumet, F., Le Mao, J., David, B. & Blank, U. Involvement of the ras-like GTPase rab3d in RBL-2H3 mast cell exocytosis following stimulation via high affinity IgE receptors (FcERI). *J Immunol* 159, 2815–23 (1997).
73. Fernandez, J. M., Neher, E. & Gomperts, B. D. Capacitance measurements reveal stepwise fusion events in degranulating mast cells. *Nature* 312, 453–5 (1984).
74. Chandler, D. E. & Heuser, J. E. Arrest of membrane fusion events in mast cells by quick-freezing. *J Cell Biol* 86, 666–74 (1980).
75. Ullrich, A. & Schlessinger, J. Signal transduction by receptors with tyrosine kinase activity. *Cell* 61, 203–12 (1990).
76. Yu, S. S., Lefkowitz, R. J. & Hausdorff, W. P. β-adrenergic receptor sequestration: A potential mechanism of receptor resensitization. *J Biol Chem* 268, 337–41 (1993).
77. James, D. E. & Piper, R. C. Insulin resistance, diabetes, and the insulin-regulated trafficking of GLUT-4. *J Cell Biol* 126, 1123–6 (1994).

We claim:

1. A pH-sensitive mutant of the GFP of *Aequorea Victoria*, wherein a change in pH of 1.9 pH units within the range of pH 5.5 to pH 10 results in the attenuation or loss of a peak in the excitation spectrum of the mutant.

2. The pH-sensitive mutant protein of claim 1, wherein said attenuation of a peak in the excitation spectrum is at least 85%.

3. The pH-sensitive mutant protein of claim 1, wherein said attenuation of a peak in the excitation spectrum is at least 90%.

4. The pH-sensitive mutant protein of claim 1, wherein said attenuation of a peak in the excitation spectrum is at least 99%.

5. The pH-sensitive mutant GFP of claim 1, wherein a change in pH of 1.9 pH units within the range of pH 5.5 to pH 10 results in the loss of a peak in the excitation spectrum of the mutant.

6. A pH-sensitive mutant of the GFP of *Aequorea Victoria* wherein a change in pH of 1.9 pH units within the range of pH 5.5 to pH 10 results in a decrease in fluorescence at a first peak of the excitation spectrum and an increase in fluorescence at a second peak of the excitation spectrum.

7. The pH-sensitive mutant GFP of claim 6, wherein said decrease in fluorescence at a first peak in the excitation spectrum is about 28% or more.

8. The pH-sensitive mutant GFP of claim 6, wherein said decrease in fluorescence at a first peak in the excitation spectrum is about 37% or more.

9. The pH-sensitive mutant GFP of claim 6, wherein said decrease in fluorescence at a first peak in the excitation spectrum is about 46% or more.

10. The pH-sensitive mutant GFP of any one of claims 6–9, wherein said increase in fluorescence at a second peak in the excitation spectrum is about 22% or more.

11. The pH-sensitive mutant GFP of any one of claims 6–9, wherein said increase in fluorescence at a second peak in the excitation spectrum is about 68% or more.

12. The pH-sensitive mutant GFP of any one of claims 6–9, wherein said increase in fluorescence at a second peak in the excitation spectrum is about 158% or more.

13. A pH-sensitive mutant of the GFP of *Aequorea Victoria* wherein at least one substitution is made at an amino acid position adjacent to one or more amino acids selected from the group consisting of the amino acids at positions 94, 96, 148, 167, 203, 205 and 222.

14. A pH-sensitive GFP according to any one of claims 1, 5, or 6, wherein at least one substitution is made at an amino acid position selected from the group consisting of positions 147, 149, 161, 163, 166, 167, 168, 175 and 202.

15. A pH-sensitive mutant protein according to claim 1 or claim 5, wherein at least one of the mutations is selected from the group consisting of Ser147Glu, Ser147Pro, Asn149Val, Asn149Gln, Asn149Thr, Asn149Leu, Asn149Asp, Asn149Tyr, Asn149Trp, Lys166Gln, Ile167Val, Arg168His, and Ser202His.

16. A pH-sensitive mutant protein according to any one of claims 1, 5, or 6, wherein at least one of the mutations is selected from the group consisting of Ser147Asp, Asn149Gln, Asn149Asp, Lys166Gln, Ile167Val and Ser202His.

17. A pH-sensitive mutant protein according to claim 1 or claim 5, wherein the mutations comprise Ser147Asp and Asn149Gln.

18. A pH-sensitive mutant protein according to claim 17 wherein the mutations further comprise Val163Ala and Ser175Gly.

19. A pH-sensitive mutant protein according to claim 6 wherein the mutations comprise Ser147Asp, Asn149Asp, Lys166Gln, Ile167Val and Ser202His.

20. A pH-sensitive mutant protein according to claim 19 wherein the mutations further comprise Val163Ala and Ser175Gly.

21. A pH-sensitive GFP according to claim 1, wherein an attenuation of an excitation peak at 395 nm and a loss of an excitation peak at 475 nm occurs upon a decrease of pH.

22. A pH-sensitive GFP according to claim 21 selected from the group consisting of 1D10 (SEQ ID NO:25), 2F10 (SEQ ID NO:26), 2H2 (SEQ ID NO:27), 1B11 (SEQ ID NO:28), 1B11t (SEQ ID NO:23), 8F6 (SEQ ID NO:29), 8F3 (SEQ ID NO:22), and 19E10 (SEQ ID NO:30).

23. A pH-sensitive GFP according to claim 6 which, in response to a decrease in pH, exhibits decreased fluorescence due to excitation at 395 nm and increased fluorescence due to excitation at 475 nm.

24. A pH-sensitive GFP according to claim 23 selected from the group consisting of 14E12 (SEQ ID NO:31), 14E12t (SEQ ID NO:24), 14C9 (SEQ ID NO:32), 14C8 (SEQ NO:33), 2G3 (SEQ ID NO:34), S202H (SEQ ID NO:35), 14D9 (SEQ ID NO:37), C6 (SEQ ID NO:20) and 8H8 (SEQ ID NO:36).

25. A fusion protein comprising the pH-sensitive GFP according to any one of claims 1 and 5–9, and at least one other amino acid sequence.

26. The fusion protein according to claim 25 wherein said other amino acid sequence targets the fusion protein to a cell.

27. The fusion protein of claim 25 wherein said other amino acid sequence targets said fusion protein to synaptic vesicle membranes.

28. The fusion protein of claim 25 wherein said other amino acid sequence is a synaptic vesicle protein.

29. The fusion protein of claim 28 wherein said other amino acid sequence is chosen from the group consisting of synaptotagmin and VAMP/synaptobrevin.

30. A pH-sensitive mutant protein according to claim 22, wherein the protein is 8F3 (SEQ ID NO:22).

31. A pH-sensitive mutant protein according to claim 24, wherein the protein is C6 (SEQ ID NO:20).

32. A fusion protein comprising the pH-sensitive mutant protein according to claim 30 or claim 31, and at least one other amino acid sequence.

\* \* \* \* \*